US012775565B2

(12) United States Patent
Yoshida et al.

(10) Patent No.: US 12,775,565 B2
(45) Date of Patent: Oct. 27, 2026

(54) MAINTENANCE METHOD

(71) Applicant: SYSMEX CORPORATION, Kobe (JP)

(72) Inventors: Takashi Yoshida, Kobe (JP); Tomohiro Kuroiwa, Kobe (JP); Seiji Takemoto, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 18/745,639

(22) Filed: Jun. 17, 2024

(65) Prior Publication Data

US 2024/0427720 A1 Dec. 26, 2024

(30) Foreign Application Priority Data

Jun. 21, 2023 (JP) ................................ 2023-102028
Jun. 21, 2023 (JP) ................................ 2023-102029

(51) Int. Cl.

*G06F 13/38* (2006.01)
*G01N 33/48* (2006.01)
*G16H 40/60* (2018.01)

(52) U.S. Cl.

CPC ........... *G06F 13/382* (2013.01); *G01N 33/48* (2013.01); *G16H 40/60* (2018.01)

(58) Field of Classification Search

CPC ........................................................ G16H 40/67
See application file for complete search history.

(56) References Cited

U.S. PATENT DOCUMENTS

2011/0295502 A1* 12/2011 Faenger ............. H04N 1/32106 235/375
2013/0056535 A1* 3/2013 Rowlandson .......... G16H 40/63 235/380
2013/0219479 A1* 8/2013 DeSoto ................... H04L 63/10 726/6
2015/0304478 A1 10/2015 Kim et al.
2022/0223283 A1* 7/2022 Biasi ....................... H04L 45/02

FOREIGN PATENT DOCUMENTS

EP 2 186 471 A1 5/2010
JP 2001229291 A 8/2001
JP 2002326566 A 11/2002

(Continued)

OTHER PUBLICATIONS

Extended European Search Report dated Oct. 29, 2024, issued by the European Patent Office in corresponding European Application No. 24182744.3-1218, (9 pages).

(Continued)

*Primary Examiner* — Henry Tsai
*Assistant Examiner* — Juanito C Borromeo
(74) *Attorney, Agent, or Firm* — BUCHANAN INGERSOLL & ROONEY PC

(57) ABSTRACT

Disclosed is a maintenance method for an analyzer that is not communicably connected to a network outside of a facility, the maintenance method comprising: presenting, by a terminal that is communicably connected to the network outside of the facility, information about a process to be executed by the analyzer; reading, by the analyzer, the information having been presented by the terminal; and executing, by the analyzer, the process indicated by the information having been read.

20 Claims, 57 Drawing Sheets

(56) References Cited

FOREIGN PATENT DOCUMENTS

| | | | | | |
|---|---|---|---|---|---|
| JP | 2007271334 | A | | 10/2007 | |
| JP | 2008003838 | A | | 1/2008 | |
| JP | 2009301481 | A | | 12/2009 | |
| JP | 4814787 | B2 | | 9/2011 | |
| JP | 2017187473 | A | | 10/2017 | |
| JP | 2019018004 | A | | 2/2019 | |
| WO | WO-2024168167 | A1 | * | 8/2024 | ........... G01N 33/569 |

OTHER PUBLICATIONS

Extended European Search Report dated Oct. 31, 2024, issued by the European Patent Office in corresponding European Application No. 24182748.4-1218, (7 pages).

* cited by examiner

FIG. 6

| MEASUREMENT ID | MEASUREMENT ITEM | QUALITY CONTROL SPECIMEN TYPE | LOT | EXPIRATION OF VALIDITY PERIOD | MEASUREMENT DATE | MEASUREMENT TIME | WBC | RBC | HGB | HCT | MCV | MCH | MCHC | PLT | FLAG |
|---|---|---|---|---|---|---|---|---|---|---|---|---|---|---|---|
| 001 | CBC | Control L1 | S3422 | 2023/05/09 | 2023/4/11 | 07:53:28 | 55.9 | 391 | 10.9 | 32.3 | 82.5 | 27.9 | 33.7 | 19.4 | YET TO BE EXTRACTED |
| 002 | CBC | Control L1 | S3422 | 2023/05/09 | 2023/4/11 | 19:05:36 | 55.9 | 391 | 10.9 | 32.3 | 82.5 | 27.9 | 33.7 | 19.4 | YET TO BE EXTRACTED |
| 003 | CBC | Control L2 | M5652 | 2023/05/10 | 2023/4/11 | 07:59:22 | 55.9 | 391 | 10.9 | 32.3 | 82.5 | 27.9 | 33.7 | 19.4 | YET TO BE EXTRACTED |
| 004 | CBC | Control L2 | M5652 | 2023/05/10 | 2023/4/11 | 19:07:39 | 55.9 | 391 | 10.9 | 32.3 | 82.5 | 27.9 | 33.7 | 19.4 | YET TO BE EXTRACTED |

QC, Intraday, 2023/04/11 17:59:22, XQ-320, F5659,
CBC, Control L1, S3422, 2023/05/09,
2023/4/11, 07:53:28, 55.9, 391, 10.9, 32.3, 82.5, 27.9, 33.7, 19.4,
2023/4/11, 19:05:36, 55.9, 391, 10.9, 32.3, 82.5, 27.9, 33.7, 19.4,
CBC, Control L2, M5652, 2023/05/10,
2023/4/11, 07:59:22, 55.9, 391, 10.9, 32.3, 82.5, 27.9, 33.7, 19.4,
2023/4/11, 19:07:39, 55.9, 391, 10.9, 32.3, 82.5, 27.9, 33.7, 19.4

FIG. 35

| MEASUREMENT ID | MEASUREMENT ITEM NAME | QUALITY CONTROL SPECIMEN TYPE | LOT | EXPIRATION OF VALIDITY PERIOD | MEASUREMENT DATE | MEASUREMENT TIME | CONCENTRATION | COUNT | CURVE ID | REAGENT 1 | REAGENT 2 | FLAG |
|---|---|---|---|---|---|---|---|---|---|---|---|---|
| 011 | FLUA | FLU-L1 | J337 | 2023/4/17 | 2023/4/11 | 07:53:28 | 1.0 | 1173 | 15 | ZS1234 | ZS9002 | YET TO BE EXTRACTED |
| 012 | FLUA | FLU-L1 | J337 | 2023/4/17 | 2023/4/11 | 19:43:06 | 1.0 | 1199 | 15 | ZS1234 | ZS9002 | YET TO BE EXTRACTED |
| 013 | FLUA | FLU-L2 | J882 | 2023/4/17 | 2023/4/11 | 07:54:33 | 2.8 | 2557 | 15 | ZS1234 | ZS9002 | YET TO BE EXTRACTED |
| 014 | FLUA | FLU-L2 | J882 | 2023/4/17 | 2023/4/11 | 19:44:22 | 2.7 | 2344 | 15 | ZS1234 | ZS9002 | YET TO BE EXTRACTED |

FIG. 40

| DEVICE ID | INSTRUCTION ID | INSTRUCTION CONTENT |
|---|---|---|
| F5659 | B1002 | CLOGGING ELIMINATION |
| F5659 | B1003 | CONSECUTIVE BLANK CHECK |
| F5659 | F2030 | SHUTDOWN |
| F5659 | F2031 | RESTART AFTER SHUTDOWN |
| F5659 | S4099 | TURN OFF BLOOD SUCTION SENSOR |
| F5659 | R3477 | RESET SERVICE SETTING |
| F5659 | S1180 | ENABLE SCREEN LOCKING |
| F5659 | S1181 | DISABLE SCREEN LOCKING |
| F5659 | X882 | READ OUT ERROR HISTORY |
| F5659 | X887 | READ OUT SERVICE DATA (RBC) |
| F5659 | X888 | READ OUT SERVICE DATA (HARDWARE) |
| F5659 | Q188 | READ OUT QUALITY CONTROL HISTORY |
| F5659 | Q220 | PERFORM QUALITY CONTROL MEASUREMENT |

| COMMAND ID | PROCESS |
|---|---|
| B1002 | CLOGGING ELIMINATION |
| B1003 | CONSECUTIVE BLANK CHECK |
| F2030 | SHUTDOWN |
| F2031 | RESTART AFTER SHUTDOWN |
| S4099 | TURN OFF BLOOD SUCTION SENSOR |
| R3477 | RESET SERVICE SETTING |
| S1180 | ENABLE SCREEN LOCKING |
| S1181 | DISABLE SCREEN LOCKING |
| X882 | READ OUT ERROR HISTORY |
| X887 | READ OUT SERVICE DATA (RBC) |
| X888 | READ OUT SERVICE DATA (HARDWARE) |
| Q188 | READ OUT QUALITY CONTROL HISTORY |

| ERROR ID | DATE AND TIME OF OCCURRENCE | ERROR CODE | ERROR MESSAGE |
|---|---|---|---|
| E1001 | 2023/3/30 16:28 | 311240 | CLOGGING IN RBC DETECTOR |
| E1002 | 2023/3/29 12:49 | 119010 | ABNORMAL DECREASE IN PRESSURE |

FIG. 59

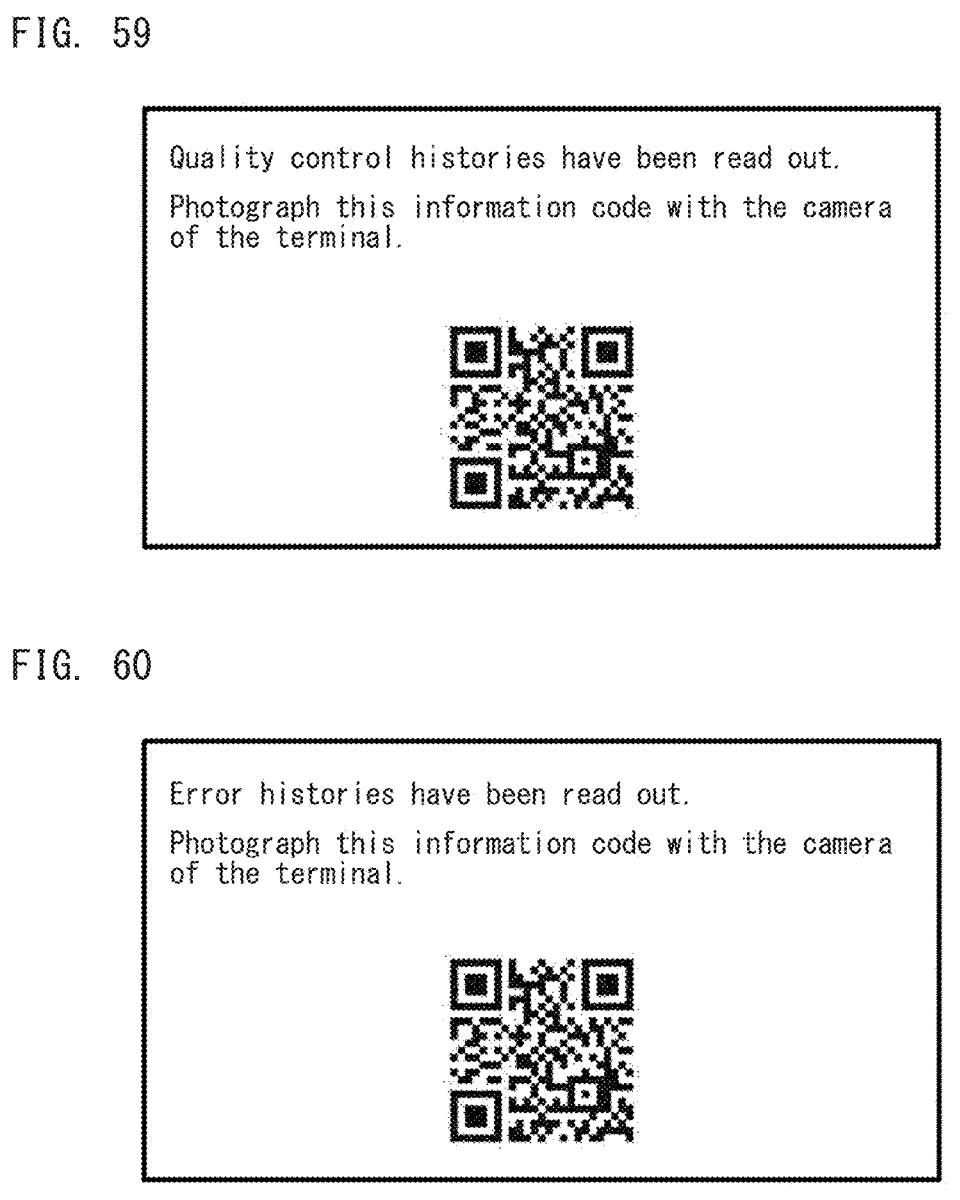

Quality control histories have been read out.

Photograph this information code with the camera of the terminal.

FIG. 60

Error histories have been read out.

Photograph this information code with the camera of the terminal.

MAINTENANCE METHOD

CROSS REFERENCE TO RELATED APPLICATIONS

This application claims priority from prior Japanese Patent Application No. 2023-102028, filed on Jun. 21, 2023, entitled “MAINTENANCE METHOD” and prior Japanese Patent Application No. 2023-102029, filed on Jun. 21, 2023, entitled “MANAGEMENT METHOD”, the entire contents of which are incorporated herein by reference.

FIELD OF THE INVENTION

The present invention relates to a maintenance method for an analyzer that is not communicably connected to a network outside of a facility.

BACKGROUND OF THE INVENTION

An analyzer is mainly installed in a laboratory of a hospital. A member of staff responsible for conducting services (hereinafter, referred to as “service staff member”) periodically visits the laboratory and performs maintenance of the analyzer, whereby the state of the analyzer is maintained such that tests can be performed at a fixed accuracy. Meanwhile, various technologies have been proposed, the technologies making it possible to, when an abnormality occurs in an analyzer, start restoration from the abnormality without calling a service staff member so as to finish the restoration as soon as possible.

For example, Japanese Laid-Open Patent Publication No. 2007-271334 discloses an information processing system including: an information server 30 which is communicably connected via a network 4 to an analyzer 20 and which stores therein pieces of countermeasure information corresponding to device abnormalities regarding the analyzer 20; and a countermeasure information display unit which obtains, from the information server 30, any of the pieces of countermeasure information corresponding to a device abnormality having occurred in the analyzer 20 and which displays the piece of countermeasure information with respect to an operator of this analyzer 20. This system makes it possible to swiftly transmit information about a device abnormality having occurred in the analyzer to the information server and enables the user to: obtain any of the pieces of countermeasure information corresponding to the abnormality; and perform restoration from the abnormality.

Analyzers handle information about the health of patients, and thus, are required to ensure a high level of security. To this end, analyzers in some facilities are not connected to the Internet. Meanwhile, some facilities are in an environment that is not regulated for the Internet. In such facilities, unlike in Japanese Laid-Open Patent Publication No. 2007-271334, a piece of countermeasure information corresponding to an abnormality cannot be obtained. Thus, it might be necessary to: inquire, by telephone, of a service staff member about how to take a countermeasure; or wait for arrival of the service staff member at the site. In a case where an operator is inexperienced, even when a piece of countermeasure information has been obtained, it might be difficult for the operator to understand the piece of countermeasure information and achieve restoration from the abnormality having occurred in the analyzer.

SUMMARY OF THE INVENTION

The scope of the present invention is defined solely by the appended claims, and is not affected to any degree by the statements within this summary.

To solve the above problem, the present invention provides a maintenance method for an analyzer (2) that is not communicably connected to a network outside of a facility, the maintenance method including: presenting, by a terminal (3) that is communicably connected to the network outside of the facility, information about a process to be executed by the analyzer (2); reading, by the analyzer (2), the information presented by the terminal (3); and executing, by the analyzer (2), the process indicated by the information.

BRIEF DESCRIPTION OF THE DRAWINGS

FIG. 6 shows a specific example of records in the quality control database;

FIG. 27 shows an example of a menu screen displayed on the terminal after logging in;

FIG. 35 shows a specific example of records in the quality control database in the case where the analyzer is an immunoassay device;

FIG. 40 shows a specific example of records in the instruction information database;

FIG. 59 shows an example of a screen, of the analyzer, in which an information code regarding quality control histories is displayed;

FIG. 60 shows an example of a screen, of the analyzer, in which an information code regarding error histories is displayed;

DETAILED DESCRIPTION

[Overview of Management Assistance System 1]

Figure 1:
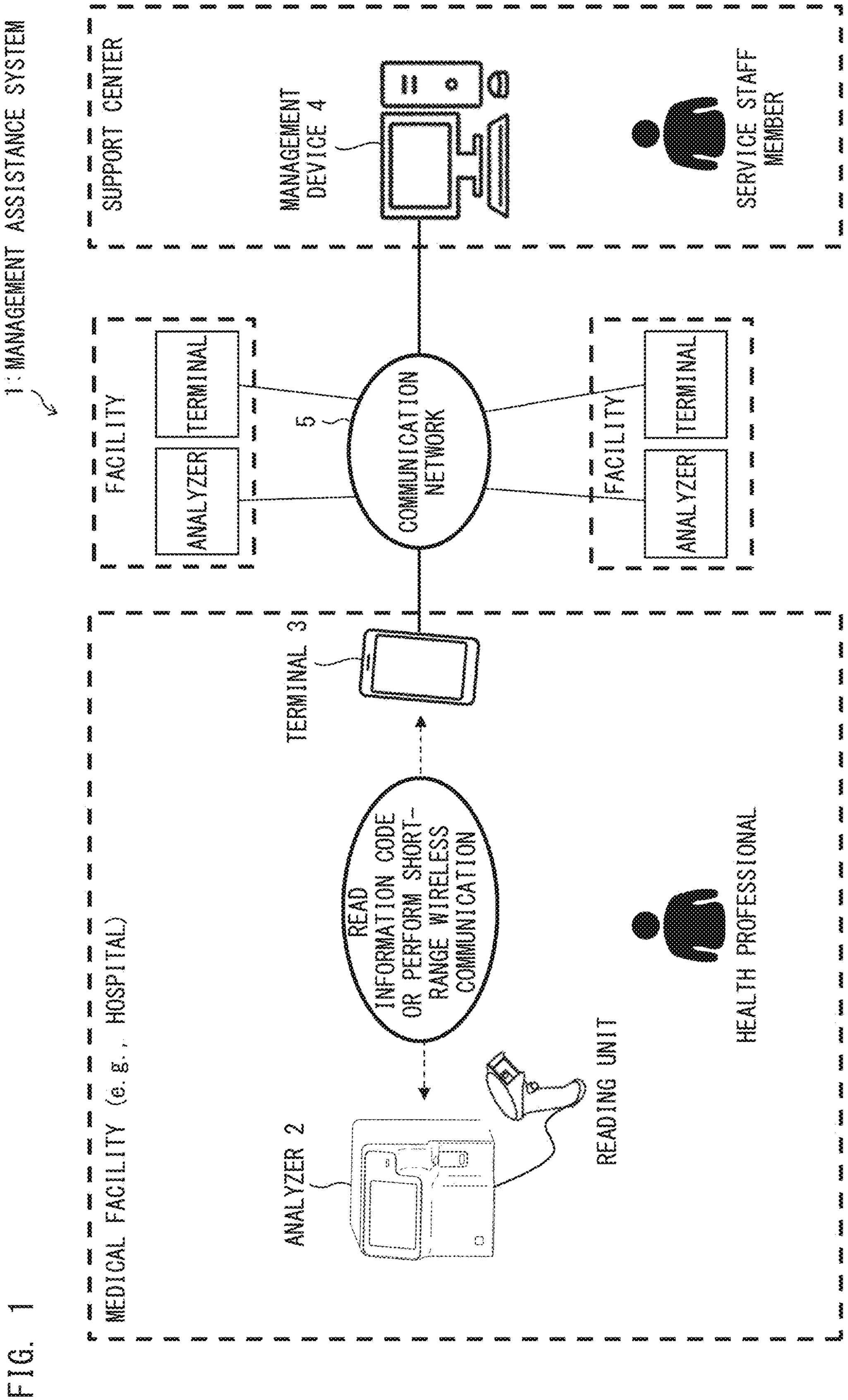
FIG. 1 is a schematic diagram showing an overview of a management assistance system.

An overview of a management assistance system 1 according to the present disclosure will be described with reference to FIG. 1. The management assistance system 1 includes an analyzer 2, a terminal 3, and a management device 4.

[Overview of Analyzer 2]

The analyzer 2 is installed in a medical facility (e.g., a hospital or a clinic) and is used by a health professional in the medical facility. The analyzer 2 is operated in an offline environment (i.e., operated in a standalone manner) or is connected only to a local area network (LAN) established inside the medical facility. That is, the analyzer 2 is not connected to a communication network 5 such as the Internet, which is established outside the medical facility. Thus, the analyzer 2 is run in an environment in which the analyzer 2 is not communicably connected to any device outside the medical facility. This manner of running is, in many cases, employed in medical facilities in which information about patients is handled, and thus, security measures of a high level are required. Also, the above manner of running is, in many cases, employed in: countries or areas in which it is not common to connect such analyzers 2 to the Internet; or countries or areas in which no communication network environment has been regulated.

The analyzer 2 analyzes a specimen. Examples of the specimen to be analyzed by the analyzer 2 include: biological specimens such as blood and urine; the bodies of humans and animals; food products and beverages; and the like. However, the specimen is not limited thereto. A typical example of the analyzer 2 is a clinical laboratory test device. A typical example of the clinical laboratory test device is a blood cell counter. Instead of the blood cell counter, the analyzer 2 may be, for example, an immunoassay device, a blood coagulation measurement device, a biochemical analyzer, or a urine analyzer.

The blood cell counter counts blood cell components such as red blood cells, white blood cells, and platelets contained in a blood specimen through an electrical-resistance-type detection method, for example. The electrical-resistance-type detection method includes: causing a blood specimen to flow between a pair of electrodes; and measuring the number of blood cells and the volume of the blood cells on the basis of a change, in the electrical resistance, that occurs when blood cells pass between the electrodes. In addition, the blood cell counter can measure the amount of hemoglobin in the blood through a non-cyanide hemoglobin method. Examples of such a blood cell counter include XQ-320 (manufactured by Sysmex Corporation). The blood cell counter may count the blood cell components through flow cytometry instead of the electrical-resistance-type detection method.

The blood cell counter performs measurement regarding specimens (hereinafter, referred to as "specimen measurement") several tens of times to several hundreds of times per day, for example. The blood cell counter is required to exhibit reproducibility for measurement results obtained at the time of measuring a same specimen, and thus, needs to be subjected to quality control (QC) for measurement. In the quality control, the blood cell counter performs measurement regarding a quality control specimen (hereinafter, referred to as "quality control measurement"). The blood cell counter performs quality control measurement several times per day, for example. Typical examples of the timing of performing quality control measurement are: a timing preceding execution of the first time of specimen measurement in one day (e.g., early in the morning); and a timing subsequent to execution of the last time of specimen measurement in one day (e.g., in the evening). Another example of the above timing is a timing that is subsequent to execution of the first time of specimen measurement in one day and that precedes execution of the last time of specimen measurement in the day (i.e., a timing within the period of execution of specimen measurement). The reason for performing quality control measurement at this timing is, for example, because quality control measurement might be performed in a case where a reagent is changed or restoration from an error occurs during one day.

In quality control measurement, analysis is performed as to whether or not a measurement value regarding the quality control specimen falls within a predetermined normal range (whether or not the amount of deviation from a reference value is equal to or smaller than a predetermined value). Specifically, the measurement value regarding the quality control specimen is a red blood cell count (RBC), a white blood cell count (WBC), a platelet count (PLT), a hemoglobin concentration (HGB), a hematocrit value (HCT), a mean corpuscular volume (MCV), a mean corpuscular hemoglobin amount (MCH), a mean corpuscular hemoglobin concentration (MCHC), or the like. Hereinafter, the measurement value regarding the quality control specimen is also referred to as a quality control result. Any measurement value within the normal range is a normal quality control result. Meanwhile, any measurement value outside the normal range is an abnormal quality control result.

The quality control is roughly classified into internal quality control and external quality control. The internal quality control is for decreasing a variation in measurement results that occurs when the same quality control specimen is measured in the same facility. Quality control specimens of the same lot are repeatedly measured by the same analyzer, and it is confirmed that an intraday variation and a day-to-day variation fall within allowable ranges. Consequently, the quality of the analyzer is maintained and controlled. In general, whether an analyzer is normal or abnormal is determined on the basis of whether or not a measurement value obtained by measuring a quality control specimen by the analyzer falls within a normal range predetermined for each quality control specimen lot. For example, in a case where the normal range of the HGB is predetermined to be from 9.6 to 11.4, a measurement value of the HGB that is, for example, 10.9 is a normal quality control result.

The external quality control is for decreasing a variation in measurement results that occurs when the same quality control specimen among a plurality of facilities is measured. Measurement results regarding quality control specimens of the same lot are aggregated from the plurality of facilities, and it is confirmed that the difference, of a measurement result in the own facility, from statistical data (e.g., an average value or a median value) of a parent population falls within an allowable range. Consequently, the quality of the corresponding analyzer is maintained and controlled. In the present embodiments, the management device 4 receives and aggregates quality control results from a plurality of facilities. Then, the management device 4 performs calculation of statistical data and performs, for each of analyzers, determination based on the calculated statistical data as to whether or not the analyzer is normal or abnormal. The type of the external quality control differs according to the manner of the external quality control in which the facilities participate. Examples of the type of the external quality control include: intraday quality control for controlling an intraday variation in quality control results; daily quality control for controlling a daily variation in quality control results; monthly quality control for controlling a monthly variation in quality control results; and the like. In the intraday quality control, each of quality control results obtained in a target day (e.g., the present day) is transmitted to the management device 4 so as to be used in the quality control. In the daily quality control, a statistical value obtained by performing, for each quality control specimen lot, statistical processing on quality control results obtained in a target day (e.g., the present day) is transmitted to the management device 4 so as to be used in the quality control. Typical examples of the statistical value are an average value, a median value, a standard deviation, a deviation, and the like. The daily quality control is ordinarily performed once per day. In the monthly quality control, a statistical value obtained by performing, for each quality control specimen lot, statistical processing on quality control results obtained in a target month (e.g., the present month) is transmitted to the management device 4 so as to be used in the quality control. Typical examples of the statistical value are an average value, a median value, a standard deviation, a deviation, and the like. The monthly quality control is ordinarily performed once per month.

The quality control specimens are also called quality control substances or control specimens. The quality control specimens each contain, for example, a whole blood component adjusted to have a known concentration. Examples of such quality control specimens include XN-CHECK (registered trademark), e-CHECK (registered trademark), and EIGHTCHECK (registered trademark) (manufactured by Sysmex Corporation). The quality control specimens may include three types of quality control specimens adjusted to be of three concentration levels which are a low concentration, a standard concentration, and a high concentration. Hereinafter, the quality control specimen of the low concentration is referred to as level 1, the quality control specimen of the standard concentration is referred to as level 2, and the quality control specimen of the high concentration is referred to as level 3 so as to be distinguished from one another. Level 1, level 2, and level 3 are respectively abbreviated as L1, L2, and L3.

[Overview of Terminal 3]

The terminal 3 is a computer used by the health professional in the medical facility and is, for example, a smartphone, a tablet terminal, or a personal computer. The terminal 3 plays an intermediary role to relay information between the analyzer 2 and the management device 4.

For relaying information between the terminal 3 and the analyzer 2, an information code that allows the information to be optically read is typically used. One of the terminal 3 and the analyzer 2 creates and displays the information code, and the other of the terminal 3 and the analyzer 2 reads the information code, to perform the relaying. A typical example of the information code is a two-dimensional code. The two-dimensional code is excellent in terms of information density, readability, information capacity, and the like and allows complicated information to be accurately conveyed with a small area. A specific example of the two-dimensional code is a QR code (registered trademark), but the two-dimensional code is not limited thereto. The relaying of the information between the analyzer 2 and the terminal 3 may be performed by utilizing short-range wireless communication instead of the information code. Typical examples of the short-range wireless communication are Bluetooth (registered trademark) and Wi-Fi (registered trademark), but the short-range wireless communication is not limited thereto.

The terminal 3 is connected to the communication network 5 via a mobile communication network or directly and can perform bidirectional communication with the management device 4 via the communication network 5. The terminal 3 may be authenticated before performing communication with the management device 4. The communication network 5 includes a closed network (a VPN network or the like) and an open network (the Internet or the like).

[Overview of Management Device 4]

The management device 4 is a computer installed in a facility different from the medical facility in which the analyzer 2 is installed (a facility positioned at a location remote from said medical facility). The management device 4 may be implemented by one computer or may be implemented by dispersing the function among a plurality of computers. The management device 4 is communicably connected to the communication network 5 and can perform bidirectional communication with the terminal 3 via the communication network 5. The management device 4 transmits, to the terminal 3, information to be transmitted to the analyzer 2 and receives, from the terminal 3, information stored in the analyzer 2. As shown in FIG. 1, the management device 4 is connected via the communication network 5 also to: analyzers in other facilities different from the medical facility in which the analyzer 2 is installed; and terminals in the other facilities. In this manner, the management device 4 can collect data from the analyzers or the terminals in the plurality of facilities and can perform, for example, large-scale data aggregation which is necessary for the external quality control.

A typical example of the facility in which the management device 4 is installed is a support center. In a case where the management device 4 is installed in a support center, the management device 4 is used by a service staff member in the support center. Hereinafter, description will be given on the assumption that a user of the management device 4 is the service staff member. The service staff member uses the management device 4 to perform, for example, (1) the external quality control, (2) assistance in maintenance and running of the analyzer 2 (hereinafter, abbreviated as "maintenance/running"), and the like.

The external quality control is quality control in which statistical analysis is performed regarding, for example, whether or not the measurement value regarding the quality control specimen falls within a predetermined allowable range in comparison with a statistical value (e.g., an average value) of an aggregation parent population composed of the plurality of medical facilities. The external quality control is performed through execution of an external quality control program by the management device 4. The result of the external quality control is provided from the management device 4 to the medical facility. The provision may be performed in the following manner, for example. That is, the result may be presented on a web page accessible to the terminal 3 used by the health professional in the medical facility or may be reported to the terminal 3 by using e-mail or a dedicated application.

In the maintenance/running, the service staff member deals with, for example, an abnormality that has occurred in the analyzer 2. Specifically, the service staff member collects and analyzes, for example, information (e.g., error histories, service data, or the like) about the status of the analyzer 2 and performs, for example, work of selecting a command to be executed by the analyzer 2.

[Example of Format of Information Code]

Information recorded in the information code used for relaying the information between the terminal 3 and the analyzer 2 includes, for example, the following pieces of information (D01) to (D06). A typical example of the data format of the recorded information is a comma separated values (CSV) format, but the data format is not limited thereto.

(D01) First code type: This is a main type for identifying the information recorded in the information code.

(D02) Second code type: This is a sub-type for identifying the information recorded in the information code. The second code type does not have to be used in a case where the first code type suffices alone.

(D03) Date-and-time information: This is, in a case where the analyzer 2 has created the information code, the date and the time of creation of the information code and/or an expiration of validity period of the information code. Meanwhile, this is, in a case where the terminal 3 has created the information code, the date and the time of issuance of instruction data (described later) issued from the management device 4 and/or an expiration of validity period of the instruction data.

(D04) Model name: This is the model name of the analyzer 2 to which the information is to be relayed.

(D05) Device ID: This is an identifier of the analyzer 2 to which the information is to be relayed.

(D06) Data body: This is the body of the information to be relayed. This is, in a case where the analyzer 2 has created the information code, one or more pieces of information read out from the analyzer 2. Meanwhile, this is, in a case where the terminal 3 has created the information code, identifiers of one or more instructions included in the instruction data.

In a case where the analyzer 2 has created the information code, information indicating a transmission destination from the terminal 3 may be recorded in the information code in addition to the above pieces of information (D01) to (D06). The information indicating the transmission destination is, for example, a uniform resource locator (URL), an e-mail address, a communication address, or the like.

Embodiment 1

The present embodiment is an embodiment in which information stored in the analyzer 2 is transmitted via the terminal 3 to the management device 4. Description will be given with quality control results being taken as an example of the information stored in the analyzer 2. According to the present embodiment, quality control results stored in the analyzer 2 being operated in an environment that does not allow communication with any devices outside the medical facility can be transmitted to the management device 4. Moreover, this transmission can be performed without any erroneous operation through only a simple operation of reading an information code, whereby even a health professional who is not proficient in handling of the analyzer 2 can easily perform the transmission.

[Configuration Example of Analyzer 2]

Figure 2:
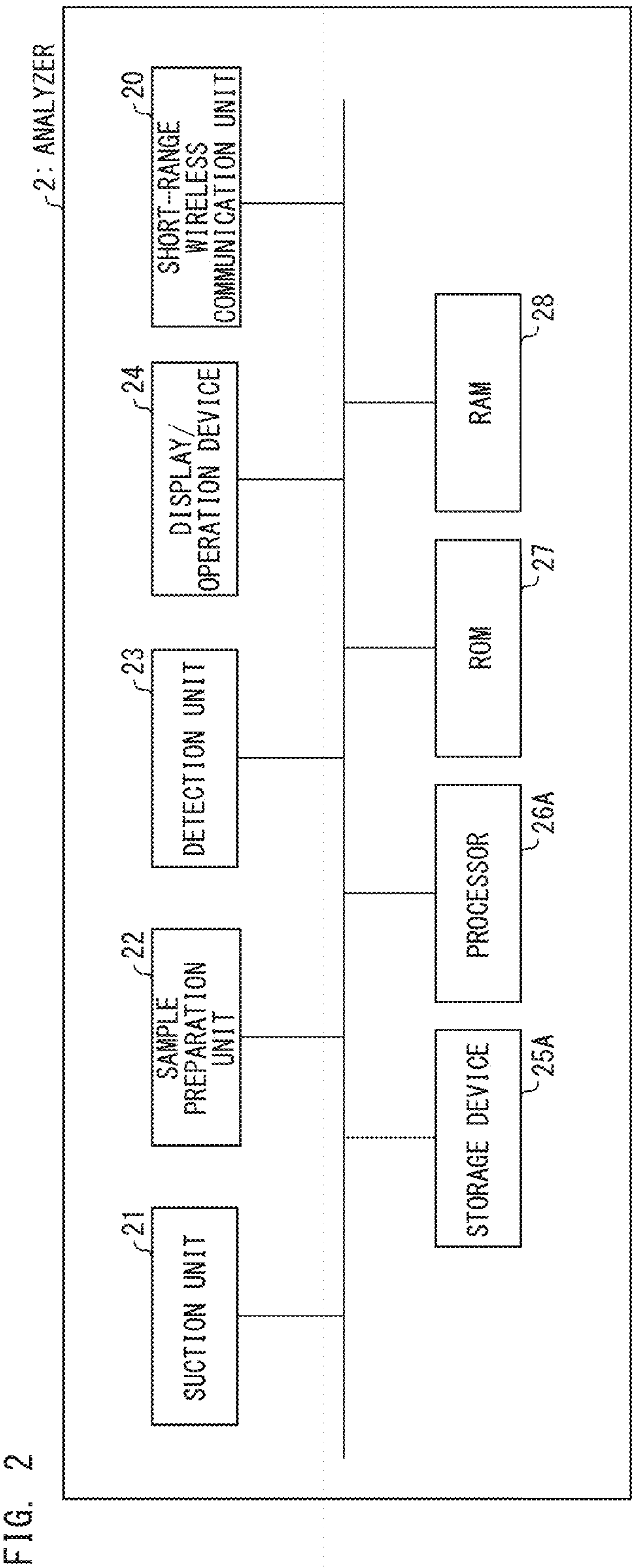
FIG. 2 shows a configuration example of an analyzer.

As shown in FIG. 2, the analyzer 2 according to the present embodiment includes, for example, a suction unit 21, a sample preparation unit 22, a detection unit 23, a display/operation device 24 (display unit), a storage device 25A (storage unit), a processor 26A, a random access memory (RAM) 27, and a read only memory (ROM) 28. In a case where short-range wireless communication is utilized for relaying the information between the analyzer 2 and the terminal 3, the analyzer 2 further includes a short-range wireless communication unit 20. The short-range wireless communication unit 20 performs short-range wireless communication with a short-range wireless communication unit 30 (described later) of the terminal 3.

The suction unit 21 includes a suction pipette, a sampling valve, and the like. The suction pipette suctions a specimen from a specimen container and sends out the specimen to the sampling valve. The sampling valve measures out a predetermined amount of the introduced specimen and causes the predetermined amount of specimen to flow to the sample preparation unit 22.

The sample preparation unit 22 includes a fluid circuit composed of a chamber, a valve, and the like for preparing a measurement sample by diluting the specimen caused to flow in from the suction unit 21.

The detection unit 23 includes an electrical-resistance-type detector for measuring red blood cells, white blood cells, platelets, and the like in the measurement sample prepared by the sample preparation unit 22. The detection unit 23 detects, as specimen data, electrical information measured by the electrical-resistance-type detector.

The display/operation device 24 is, for example, a touch-panel-type display. The display/operation device 24 displays quality control results, specimen measurement results, various menus, and the like. In addition, the display/operation device 24 receives an operation for inputting a specimen number, an operation for selection from various menus, and the like. The display/operation device 24 may include a mouse and a keyboard as devices for receiving the operations from a user.

Figure 3:
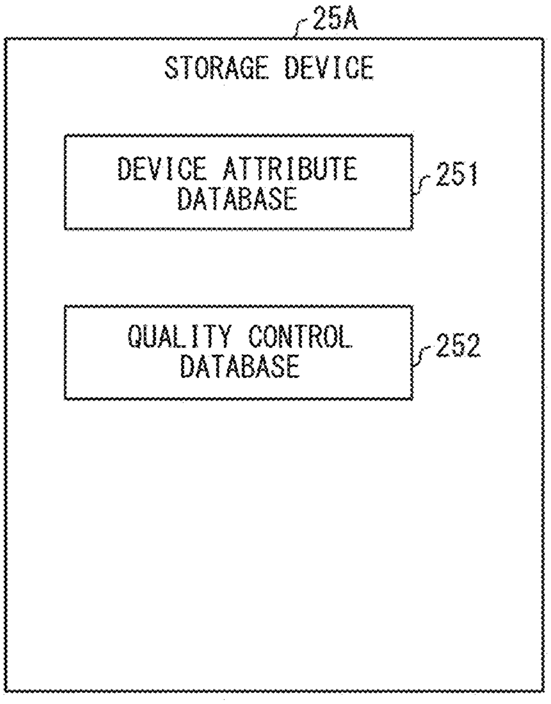
FIG. 3 shows a configuration example of a storage device of the analyzer.

The storage device 25A is for storing therein various data and various programs to be used by the analyzer 2 and is, for example, a semiconductor drive such as a solid-state drive or a magnetic disk such as a hard disk. As shown in FIG. 3, the storage device 25A stores therein, for example, a device attribute database 251 and a quality control database 252.

Figure 4:
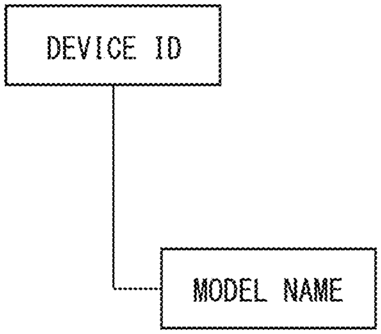
FIG. 4 shows an example of the data structure of a device attribute database.

The device attribute database 251 is a database for storing therein attribute information about the analyzer 2 and is, for example, a relational database (RDB). FIG. 4 shows an example of a data structure in a case where the device attribute database 251 is an RDB. As shown in the drawing, the device attribute database 251 stores therein, for example, the following pieces of information (D11) and (D12) such that these pieces of information are associated with each other.

(D11) Device ID: This is the identifier of the analyzer 2.

(D12) Model name: This is the model name of the analyzer 2. An example of the model name is "XQ-320".

Figure 5:
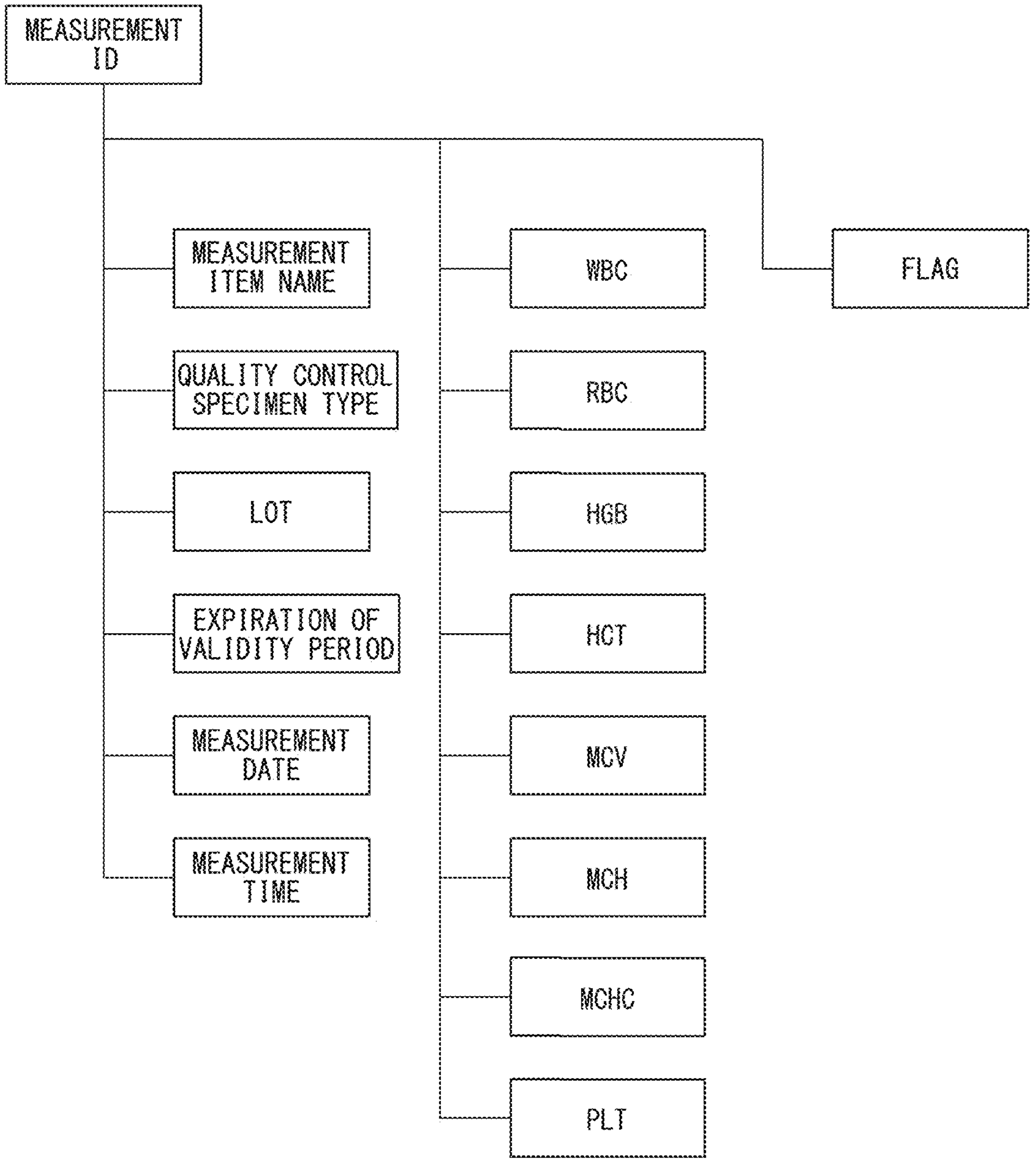
FIG. 5 shows an example of the data structure of a quality control database.

The quality control database 252 is a database for storing therein information about quality control measurement and is, for example, an RDB. FIG. 5 shows an example of a data structure in a case where the quality control database 252 is an RDB. As shown in the drawing, the quality control database 252 stores therein, for example, the following pieces of information (D21) to (D36) such that these pieces of information are associated with one another.

(D21) Measurement ID: This is an identifier of quality control measurement.

(D22) Measurement item name: This is the name of the quality control measurement. An example of the measurement item name is "CBC" (complete blood count).

(D23) Quality control specimen type: This is the concentration level of a quality control specimen used for the quality control measurement. Examples of the quality control specimen type are "Control L1" (level 1), "Control L2" (level 2), and "Control L3" (level 3).

(D24) Lot: This is the lot number of the quality control specimen used for the quality control measurement.

(D25) Expiration of validity period: This is the expiration of validity period of the quality control specimen used for the quality control measurement.

(D26) Measurement date: This is the date of execution of the quality control measurement.

(D27) Measurement time: This is the time of execution of the quality control measurement. The measurement date and the measurement time may be combined.

(D28) WBC: This is the measurement value of the white blood cell count which is one of quality control results.

(D29) RBC: This is the measurement value of the red blood cell count which is one of the quality control results.

(D30) HGB: This is the measurement value of the hemoglobin concentration which is one of the quality control results.

(D31) HCT: This is the measurement value of the hematocrit value which is one of the quality control results.

(D32) MCV: This is the measurement value of the mean corpuscular volume which is one of the quality control results.

(D33) MCH: This is the measurement value of the mean corpuscular hemoglobin amount which is one of the quality control results.

(D34) MCHC: This is the measurement value of the mean corpuscular hemoglobin concentration which is one of the quality control results.

(D35) PLT: This is the measurement value of the platelet count which is one of the quality control results.

(D36) Flag: This is a flag indicating whether or not the quality control results have been extracted.

FIG. 6 shows a specific example of records in the quality control database 252. The drawing shows four records. The two records on the upper side indicate quality control results of quality control specimens with the quality control specimen type being Control L1, with the lot being S3422, and with the expiration of validity period being May 9, 2023. The dates and the times of execution of the quality control measurements are, in order from the upper record, 07:53:28 on Apr. 11, 2023 and 19:05:36 on the same date. The two records on the lower side indicate quality control results of quality control specimens with the quality control specimen type being Control L2, with the lot being M5652, and with the expiration of validity period being May 10, 2023. The dates and the times of execution of the quality control measurements are, in order from the upper record, 07:59:22 on Apr. 11, 2023 and 19:07:39 on the same date.

With reference back to FIG. 2, the processor 26A is a controller that comprehensively controls the functions of the analyzer 2. The processor 26A is, for example, a central processing unit (CPU). The processor 26A may be implemented by, for example, a logic circuit. The processor 26A reads out an application 261A from the storage device 25A, loads the application 261A to the RAM 27, and executes the application 261A. The application 261A is stored in, for example, the storage device 25A as a program for causing a computer to function as a controller for executing various processes.

[Configuration Example of Application 261A]

Figures 7, 8:
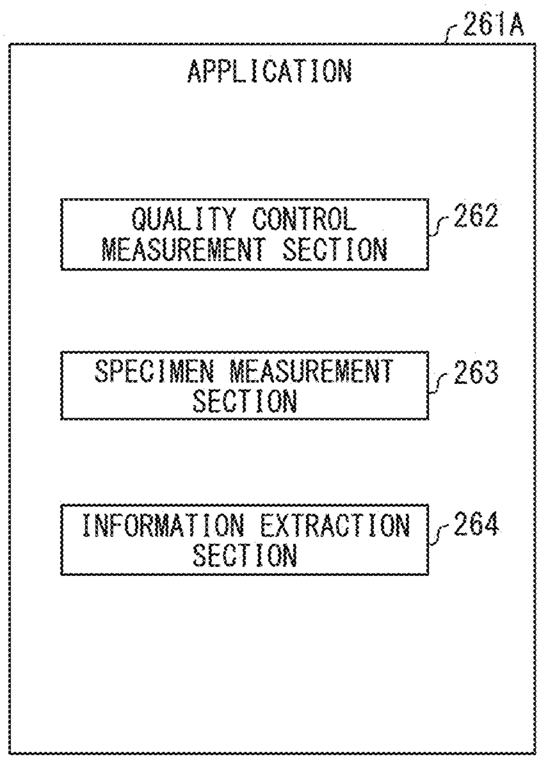
FIG. 7 shows a configuration example of an application that is operated in the analyzer.
FIG. 8 shows a specific example of data recorded in an information code created through a quality control information extraction process.

FIG. 7 shows a configuration example of the application 261A. The application 261A includes, for example, a quality control measurement section 262, a specimen measurement section 263, and an information extraction section 264.

When the display/operation device 24 receives an input operation for starting quality control measurement, the processor 26A executes a quality control measurement process according to an instruction from the quality control measurement section 262. In the quality control measurement process, for example, units including the suction unit 21, the sample preparation unit 22, and the detection unit 23 are operated to perform measurement regarding a quality control specimen, and a quality control result is displayed on the display/operation device 24 and stored in the quality control database 252.

When the display/operation device 24 receives an input operation for starting specimen measurement, the processor 26A executes a specimen measurement process according to an instruction from the specimen measurement section 263. In the specimen measurement process, for example, the units including the suction unit 21, the sample preparation unit 22, and the detection unit 23 are operated to perform measurement regarding a specimen, and a measurement result is displayed on the display/operation device 24 and stored in the storage device 25A.

In addition, the processor 26A executes a quality control information extraction process according to an instruction from the information extraction section 264. The trigger for execution of the quality control information extraction process may be reception, by the display/operation device 24, of an input operation for extracting quality control information or may be arrival of the date and the time having been scheduled. In the quality control information extraction process, quality control results satisfying an extraction condition are obtained from the quality control database 252, an information code that allows reading of each of the obtained quality control results or a value (a statistical value or the like) calculated on the basis of these quality control results is created, and the display/operation device 24 is caused to display the created information code. Consequently, the quality control results to be used in external quality control to be performed by the management device 4 can be extracted alone. The quality control results to be used in external quality control to be performed by the management device 4 are one kind of management information to be obtained by the management device 4. In the quality control database 252, an extracted record has a flag 274 indicating that this record has been extracted. In the present specification, "extracting" information from the storage unit is also expressed as "reading out" information from the storage unit.

In a first typical example of the extraction condition, only quality control results obtained within a specified time range are set as extraction targets. In a case where a plurality of times of quality control measurement have been performed within the specified time range, each of the obtained quality control results is set as an extraction target. Specific examples of the time range are the present day, the present month, and the like. Specific times at the start and the end of the present day are, for example, 23:00 of the previous day and 09:00 of the next day, respectively. The dates and the times at the start and the end of the time range may be set as appropriate.

In the first typical example, the quality control results to be set as extraction targets may be "all" of the quality control results obtained within the specified time range or may be "only quality control results that have not been previously extracted (i.e., have yet to be extracted)" among the quality control results obtained within the specified time range. In the latter case, the volume of the information recorded in the information code can be decreased.

In a second typical example of the extraction condition, quality control results based on a quality control rule laid down in the medical facility are set as extraction targets. In a case where the rule stipulates execution of intraday quality control, each of quality control results obtained in a target day is set to be used in quality control. The quality control results to be set as extraction targets may be all of the quality control results obtained in the target day, may be only quality control results having yet to be set as extraction targets among the quality control results obtained in the target day, or may be individually selected from among the quality control results obtained in the target day.

In a case where the rule stipulates execution of daily quality control, each of quality control results obtained in a target day is set as an extraction target. In a case where the rule stipulates execution of monthly quality control, each of quality control results obtained in a target month is set as an extraction target.

In a case where the rule stipulates, for example, the following timings (T1) to (T3) as the timings of execution of quality control in one day, each of quality control results obtained at the predetermined timings may be set to be used in quality control:

(T1) a timing preceding execution of the first time of specimen measurement in one day;

(T2) a timing that is subsequent to execution of the first time of specimen measurement in one day and that precedes execution of the last time of specimen measurement in the day; and (T3) a timing subsequent to execution of the last time of specimen measurement in one day.

In many cases, the above timing (T2) is, for example, an irregular timing due to reagent replacement, restoration from an error, or the like. Thus, in a medical facility in which external quality control is basically performed only at the above timings (T1) and (T3), the above timing (T2) is not selected, whereby quality control results obtained at the above timing (T2) can be set not to be used in external quality control.

In a third typical example of the extraction condition, only quality control results that conform to an internal quality control standard in the medical facility are set as extraction targets. The quality control results that conform to the internal quality control standard refer to normal quality control results. In the third typical example, only normal quality control results are set as extraction targets, and abnormal quality control results are not set as extraction targets. Consequently, the reliability of data of the parent population in external quality control can be guaranteed, and the reliability of data of a daily average and a monthly average can be guaranteed.

In a fourth typical example of the extraction condition, only quality control results regarding a quality control specimen of a specified concentration level are set as extraction targets. As specific examples, the only quality control results to be set as extraction targets may be quality control results of L1 and L2 or quality control results of L1.

Among these extraction conditions, a plurality of different conditions may be combined. For example, at least any ones of the first typical example, the second typical example, the third typical example, and the fourth typical example described above may be combined. For example, the only quality control results to be set as extraction targets may be quality control results obtained in the present day, the quality control results being normal and having concentration levels of L1 and L2.

The extraction condition may be capable of being preset by using a setting menu or the like or may be capable of being set at the time of execution of the quality control information extraction process.

[Information Recorded in Information Code]

Information recorded in an information code created through the quality control information extraction process is, for example, as indicated by the following pieces of information (D41) to (D46).

(D41) First code type: An example thereof is "QC".

(D42) Second code type: An example thereof in the case of intraday quality control is "Intraday". An example thereof in the case of daily quality control is "Daily". An example thereof in the case of monthly quality control is "Monthly".

(D43) Date-and-time information: This is the date and the time of creation of the information code by the analyzer 2.

(D44) Model name: This is the model name of the analyzer 2 having created the information code. The model name is obtained from the device attribute database 251.

(D45) Device ID: This is the identifier of the analyzer 2 having created the information code. The device ID is obtained from the device attribute database 251.

(D46) Data body: This is composed of the above pieces of quality control information (D22) to (D35). These are obtained from the quality control database 252. The values of the above pieces of quality control information (D28) to (D35) in the case of intraday quality control are the measurement values themselves which have been obtained from the quality control database 252. Meanwhile, the values of the above pieces of quality control information (D28) to (D35) in the case of each of daily quality control and monthly quality control are statistical values (e.g., average values) obtained by performing statistical processing on the measurement values obtained from the quality control database 252.

FIG. 8 shows a specific example of the data recorded in the information code created through the quality control information extraction process. In the drawing, information about a first code type "QC", a second code type "Intraday", date-and-time information "17:59:22 on Apr. 11, 2023", a model name "XQ-320", a device ID "F5659", and four records shown in FIG. 6 as quality control results of intraday quality control is written in a CSV format. The information shown in FIG. 8 contains a total of 340 characters, and this amount of data can be recorded in one information code. As an information code in this case, a QR code of version 10 with the error correction level being L (with the restoration capability being 7%) may be used, for example. The maximum number of characters that can be recorded in this QR code is 395 alphanumeric characters, and thus all the information shown in FIG. 8 can be recorded in this QR code. As exemplified in FIG. 8, in the present embodiment, a plurality of (in the example in FIG. 8, four) quality control results are included in one QR code, and thus the user only has to photograph the QR code once. Therefore, convenience to the user is higher than in the case where the quality control results are converted into QR codes one by one. Regarding quality control measurement, quality control specimens of different concentration levels are measured a plurality of times in one day, in many cases. Thus, when the quality control results are converted into QR codes one by one, the number of times of photographing increases, and it is also likely that the user forgets to photograph a QR code in some cases. In this respect, the analyzer 2 automatically extracts quality control results having yet to be transmitted and converts the quality control results into one QR code, whereby the user can be prevented from forgetting to photograph the QR code.

The processor 26A may be capable of changing the version (the size of the QR code) according to the data amount of the information code to be created through the quality control information extraction process. For example, when the data amount is smaller than that of the information shown in FIG. 8, a QR code of version 9 or a lower level may be generated. Meanwhile, when the data amount is larger than that of the information shown in FIG. 8, a QR code of version 11 or a higher level may be generated. However, a display region of the display/operation device 24 of the analyzer 2 is limited. Thus, in a case where the amount of data included in the information code exceeds a predetermined data amount, it is also possible to, instead of increasing the version, divide the QR code into two or more information codes and sequentially display the information codes. In the case of performing the division into two or more information codes, for example, the first information code is displayed, and, when inputting is performed so as to indicate that photographing of the information code has been completed by the user, the next information code is displayed. In this case, each of the information codes may include information indicating that the information code has resulted from division. For example, in a case where the information code is divided into three information codes, the information codes include respective character strings such as "⅓", "⅔", and "3/3 (END)". In a case where an information code having been read by the terminal 3 includes information indicating that the information code has resulted from division, the terminal 3 may display a screen prompting the user to cause reading of all of the information codes resulting from division. By thus dividing the information code, large data can be converted into information codes and can be relayed to the terminal 3 even though the display region is limited. In addition, in the case of dividing the information code as well, data can be prevented from failing to be transmitted because the user forgets to perform photographing.

The information code exemplified in FIG. 8 has a data structure in which pieces of information that are common to the plurality of quality control results, i.e., the first code type (D41), the second code type (D42), the date-and-time information (D43), the model name (D44), and the device ID (D45), are written as common items. Furthermore, the information code exemplified in FIG. 8 includes pieces of information that are common to two records regarding a measurement ID of 001 and a measurement ID of 002 among the four records shown in FIG. 6. That is, the pieces of information that are common to the two records are the measurement item, the quality control specimen type, the lot, and the expiration of validity period. These pieces of information are written only once. With such a data structure, the information amount of the data contained in the information code can be decreased.

[Example of Screen of Analyzer 2]

Figure 9:
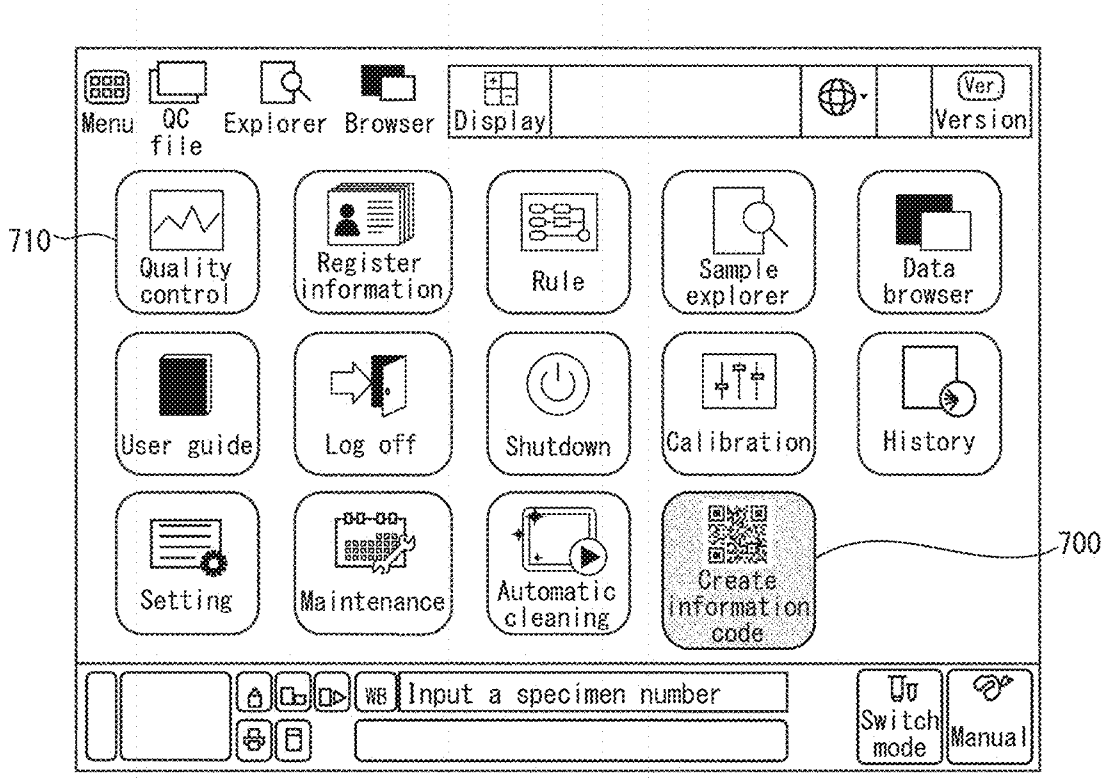
FIG. 9 shows an example of a menu screen displayed on the analyzer.
Figure 10:
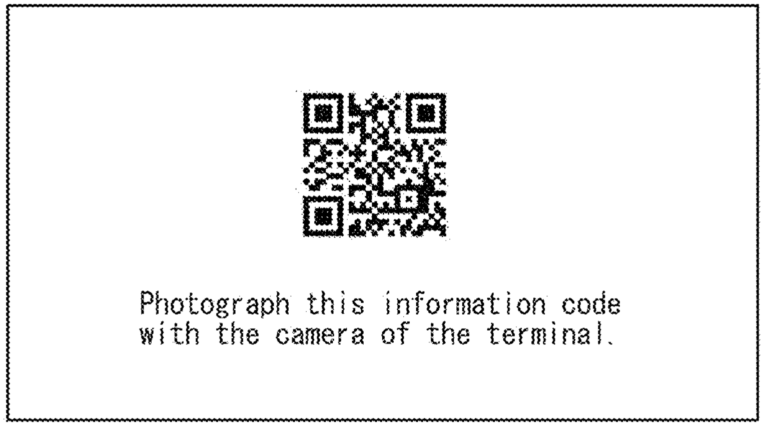
FIG. 10 shows an example of a screen, of the analyzer, in which the information code is displayed.

An example of a screen displayed on the display/operation device 24 will be described. FIG. 9 shows an example of a menu screen. The menu screen is a screen in which various processes capable of being executed by the analyzer 2 are listed in a selectable manner. In the example shown in the drawing, an icon 700 is provided as one of menu items in the menu screen. When the user touches the icon 700, the processor 26A executes the quality control information extraction process according to an instruction from the information extraction section 264 and causes the display/operation device 24 to display a created information code. FIG. 10 shows an example of a screen in which the created information code is displayed. As shown in FIG. 10, a message prompting photographing of the created information code such as the message "Photograph this information code with the camera of the terminal." is displayed in the screen together with the information code.

Figure 11:
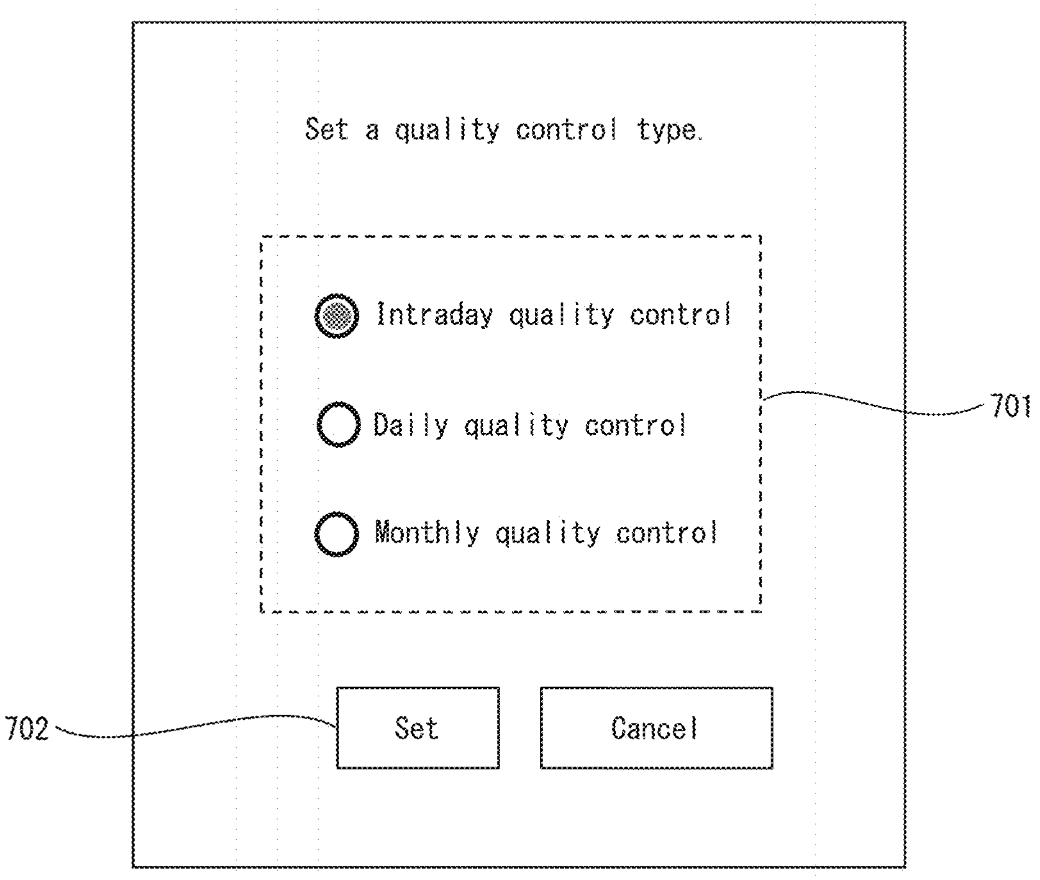
FIG. 11 shows an example of a screen, of the analyzer, for setting a quality control type.

FIG. 11 shows an example of a screen for setting a quality control type. This screen may be capable of being displayed as a result of transition from the menu screen. In the example shown in the drawing, a field 701 is provided with radio buttons for selecting any of "Intraday quality control", "Daily quality control", and "Monthly quality control". When the user selects any of the radio buttons and touches a button 702, the processor 26A causes, according to an instruction from the information extraction section 264, the storage device 25A to store therein the quality control type selected in the field 701.

Figure 12:
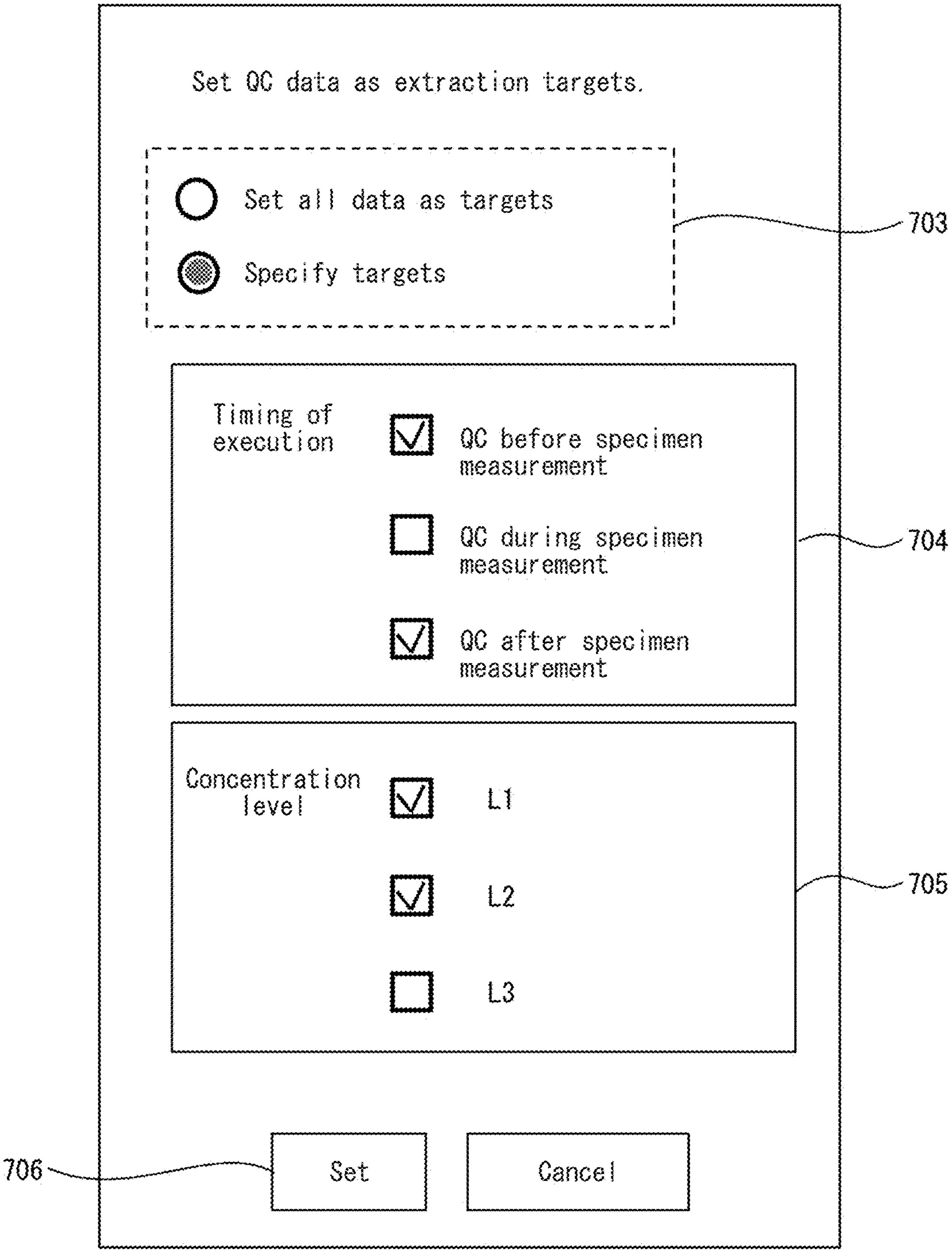
FIG. 12 shows an example of a screen for setting extraction conditions according to which quality control information is to be automatically extracted by the analyzer.

FIG. 12 shows an example of a screen for setting extraction conditions according to which quality control information is to be automatically extracted by the analyzer 2. This screen may be capable of being displayed as a result of transition from the menu screen or may be displayed at the time of execution of the quality control information extraction process.

A field 703 is provided with radio buttons for selecting either of "Set all data as targets" and "Specify targets". When the user touches the radio button corresponding to "Set all data as targets" on the touch panel, all of quality control results obtained in a target day or a target month are set to be used in quality control. In this case, checkboxes in a field 704 and a field 705 are locked so as to become inoperable. When the user selects the radio button corresponding to "Specify targets", the checkboxes in the field 704 and the field 705 become selectable.

The field 704 is provided with checkboxes for selecting a timing of performing quality control measurement. "QC before specimen measurement" corresponds to a quality control result obtained before the first time of specimen measurement in the target day is performed. "QC during specimen measurement" corresponds to a quality control result obtained after the first time of specimen measurement in the target day is performed but before the last time of specimen measurement in the target day is performed. "QC after specimen measurement" corresponds to a quality control result obtained after the last time of specimen measurement in the target day is performed.

The field 705 is provided with checkboxes for selecting any of the concentration levels (L1, L2, and L3) of a quality control specimen.

When the user sets extraction conditions in fields 703, 704, and 705 and touches a button 706, the processor 26A causes, according to an instruction from the information extraction section 264, the storage device 25A or the RAM 27 to store therein the extraction conditions selected in the fields 703 to 705. Here, the extraction conditions stored in the storage device 25A or the RAM 27 are used for a quality control information extraction process (FIG. 17) described later. Therefore, the user can preset extraction conditions via the screen in FIG. 11 or FIG. 12 and does not need to set, every time, quality control information that is to be transmitted to the management device 4 for external quality control.

Figure 13:
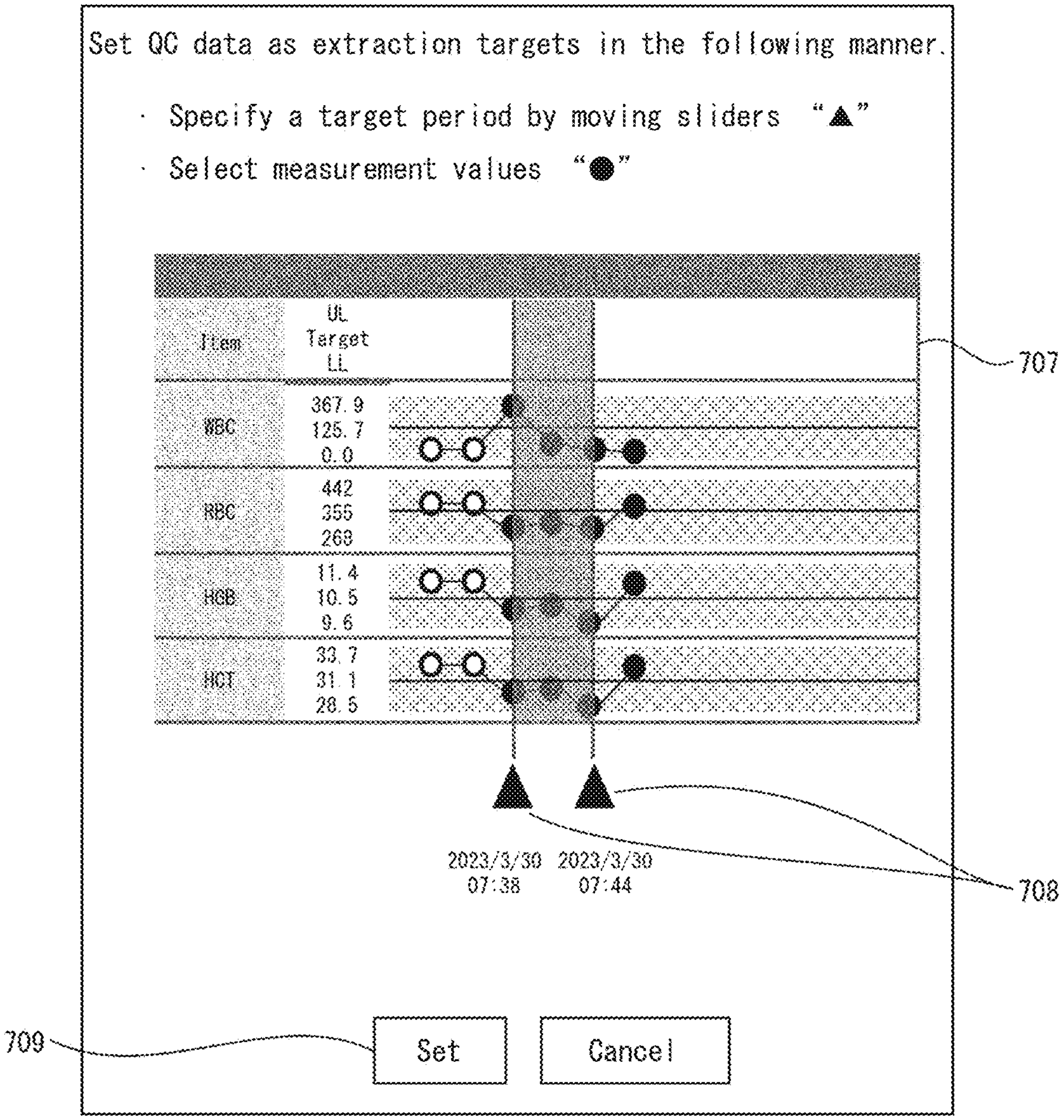
FIG. 13 shows another example of the screen, of the analyzer, for setting extraction conditions.

FIG. 13 shows another example of the screen for setting extraction conditions. This screen may be capable of being displayed as a result of transition from a confirmation screen, for quality control results, that is displayed by selecting a quality control icon 710 in FIG. 9 or may be displayed at the time of execution of the quality control information extraction process, for example. In the case of enabling transition from the confirmation screen for quality control results, the confirmation screen for quality control results may be provided with a button having the text "Create an information code", for example. When the user selects this button, the screen in FIG. 13 is displayed. The screen in FIG. 13 is suitable for, instead of presetting an extraction condition by the user as exemplified in FIG. 11 and FIG. 12, individually specifying quality control results that are desired to be externally transmitted.

A field 707 is a field for: displaying, as a time series graph, measurement values which are quality control results; and selecting measurement values. Measurement values indicated by black circles plotted on the time series graph can be selected. Meanwhile, measurement values indicated by white circles plotted on the time series graph cannot be selected since an aggregation period has elapsed. On the time series graph in FIG. 13, measurement values of the plurality of measurement items (WBC, RBC, HGB, HCT ···) are displayed so as to be arrayed in the vertical direction. The measurement values compose one quality control result, i.e., correspond to one time of quality control measurement.

Sliders 708 are for specifying a period for extraction targets. The sliders 708 can be moved to the left and right by being dragged in a state of being touched by the user. In the example shown in the drawing, the starting time and the ending time of the period for extraction targets can be set by moving the respective sliders 708 to the left and right. Although three quality control results are specified in the example of the screen in FIG. 13, it is also possible to specify only one quality control result as an extraction target. The means for specifying the period for extraction targets is not limited to movement of the sliders 708 and may be touching, by the user, of black circles plotted on the time series graph, for example.

When the user operates a button 709, the processor 26A causes, according to an instruction from the information extraction section 264, the storage device 25A or the RAM 27 to store therein the extraction condition selected in the field 707 by means of the sliders 708.

[Example of Flow of Processing To Be Executed by Analyzer 2]

Figure 14:
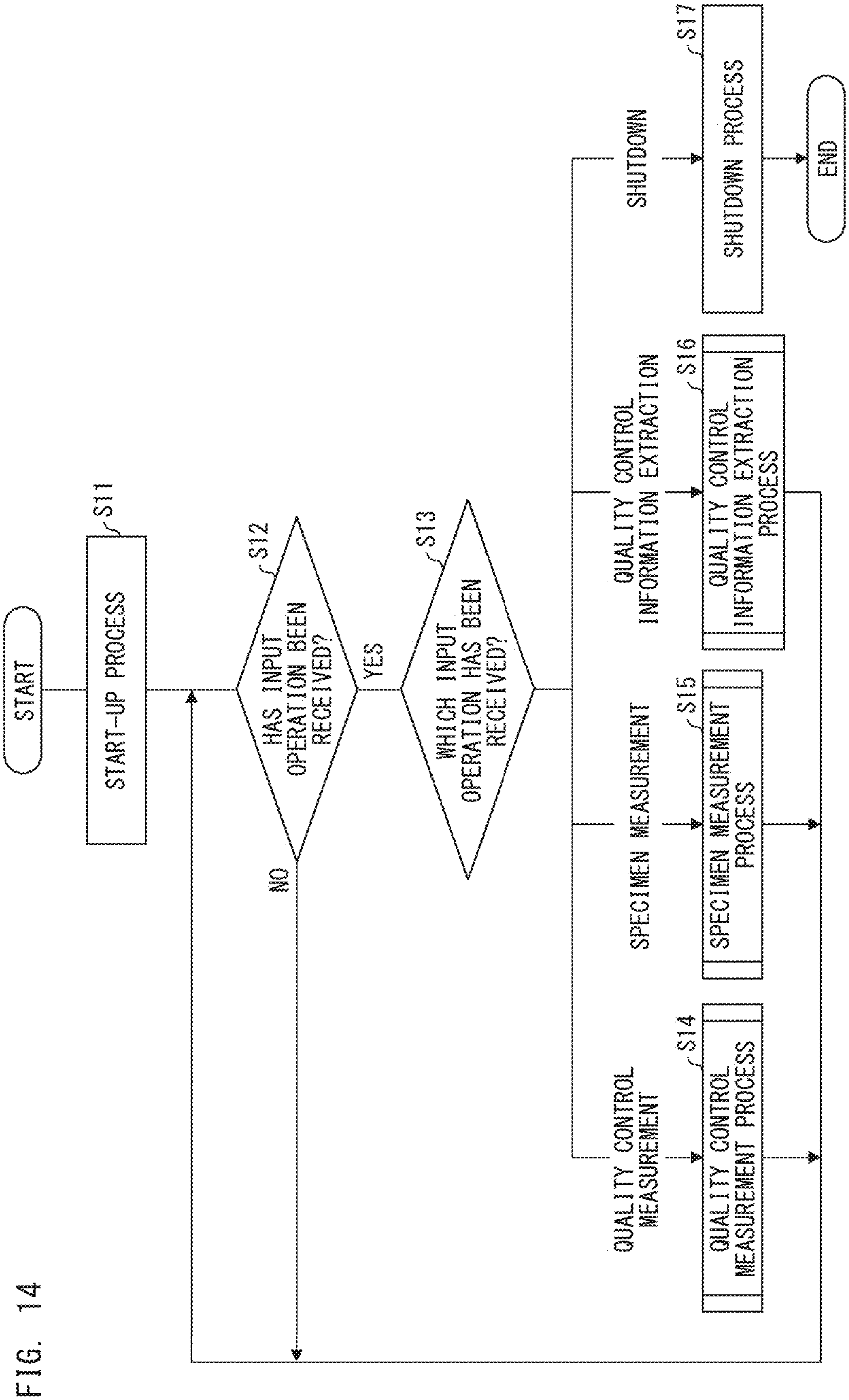
FIG. 14 is a flowchart showing an example of the flow of processing to be executed by the analyzer.

FIG. 14 is a flowchart showing an example of the flow of processing to be executed by the processor 26A of the analyzer 2. First, when a power supply of the analyzer 2 is turned on, the processor 26A executes a start-up process (S11). The start-up process includes, for example: initializing a mechanism unit and a fluid unit of the analyzer 2; cleaning the fluid unit; standing by until the temperature of a measurement module is stabilized; and performing background check.

Figure 15:
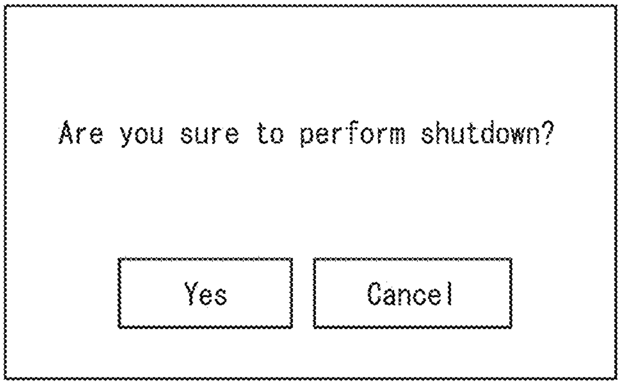
FIG. 15 shows an example of a confirmation screen, of the analyzer, displayed at the time of starting shutdown.

After the start-up process is ended, when the processor 26A receives an input operation (YES in S12), the processor 26A executes a process based on the input operation (S13 to S17). In a case where the input operation is an operation for starting "quality control measurement", the processor 26A executes a quality control measurement process (S14). In a case where the input operation is an operation for starting "specimen measurement", the processor 26A executes a specimen measurement process (S15). In a case where the input operation is an operation for starting "quality control information extraction", the processor 26A executes a quality control information extraction process (S16, extraction step). In a case where the input operation is an operation for starting "shutdown", the processor 26A causes the display/operation device 24 to display, for example, a confirmation screen shown in FIG. 15 and then executes a shutdown process (S17) so as to turn off the power supply. The shutdown process includes, for example: discharging a waste liquid; cleaning a flow path and the like; and the like.

Step S16 (extraction step) is a part of a step (preparation step) of preparing management information that is to be obtained by the management device 4 and that is included in information stored in the analyzer 2. The preparation step includes: converting the management information into an information code optically readable by the terminal 3, and displaying the information code on the display/operation device 24; or creating transmission data for transmitting the management information from the analyzer 2 to the terminal 3 through short-range wireless communication.

Figure 16:
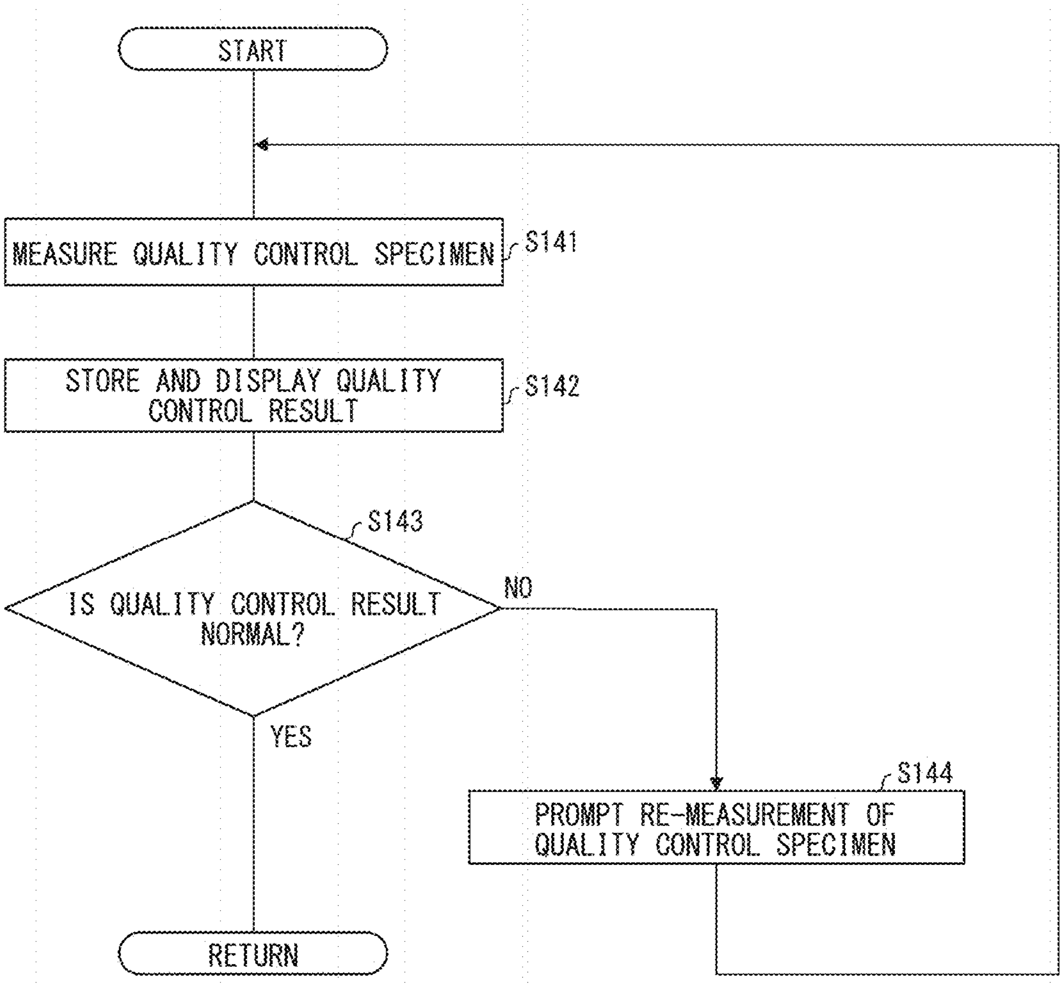
FIG. 16 is a flowchart showing an example of the flow of a quality control measurement process.

FIG. 16 is a flowchart showing an example of the flow of the quality control measurement process. The processor 26A causes the units including the suction unit 21, the sample preparation unit 22, and the detection unit 23 to operate so as to perform measurement regarding a quality control specimen (S141). Then, the processor 26A causes the quality control database 252 to store therein a quality control result and causes the display/operation device 24 to display the quality control result (S142). In a case where the quality control result is abnormal (NO in S143), the processor 26A may output, to the display/operation device 24, information prompting re-measurement (S144). Meanwhile, in a case where the quality control result is normal (YES in S143), the processor 26A ends the quality control measurement process.

Figure 17:
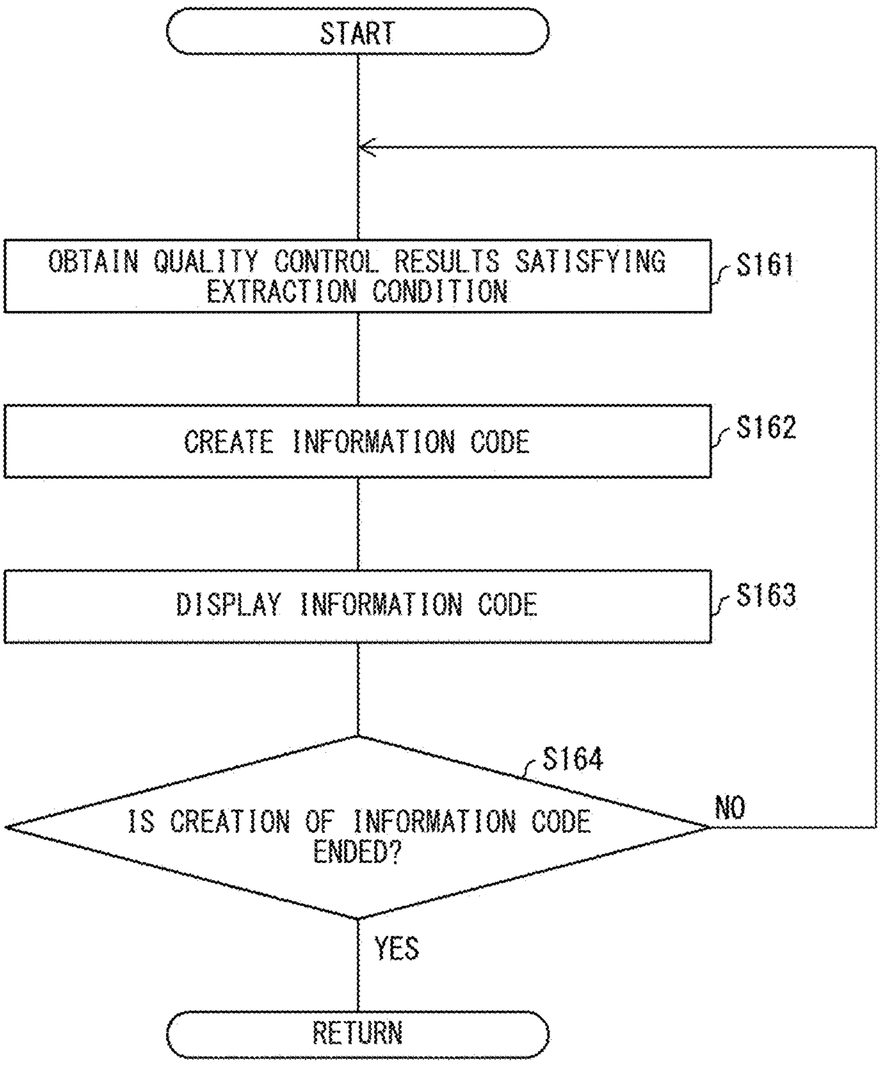
FIG. 17 is a flowchart showing an example of the flow of the quality control information extraction process.

FIG. 17 is a flowchart showing an example of the flow of the quality control information extraction process. The processor 26A obtains, from the quality control database 252, quality control results satisfying an extraction condition (S161). The processor 26A creates an information code that allows reading of each of the obtained quality control results or a value calculated on the basis of these quality control results (S162). The processor 26A causes the display/operation device 24 to display the created information code (S163). When an input operation for ending the quality control information extraction process is received (YES in S164), the processor 26A ends the quality control information extraction process.

Figure 18:
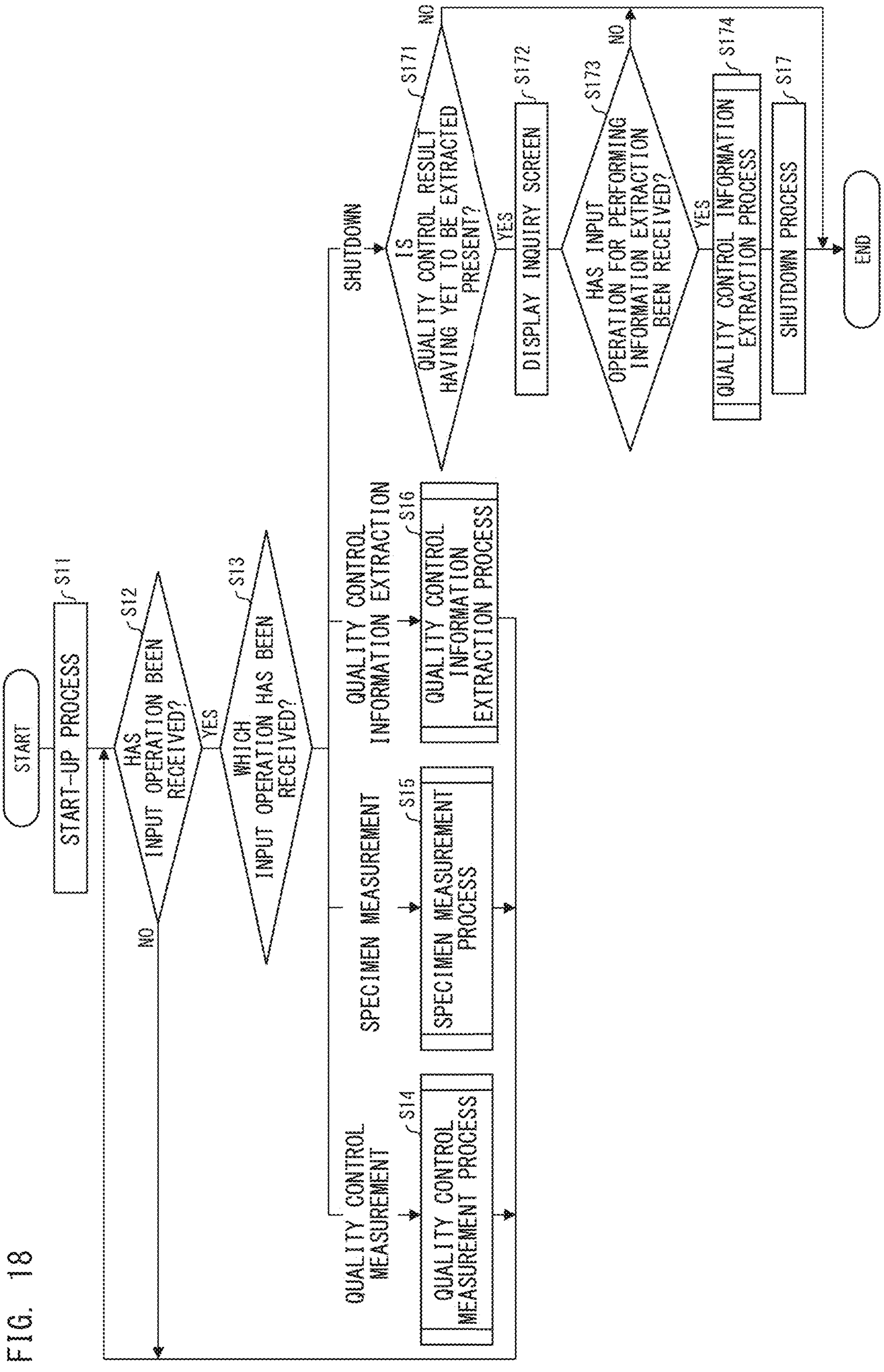
FIG. 18 is a flowchart showing a modification of the flowchart shown in FIG. 14.
Figure 19:
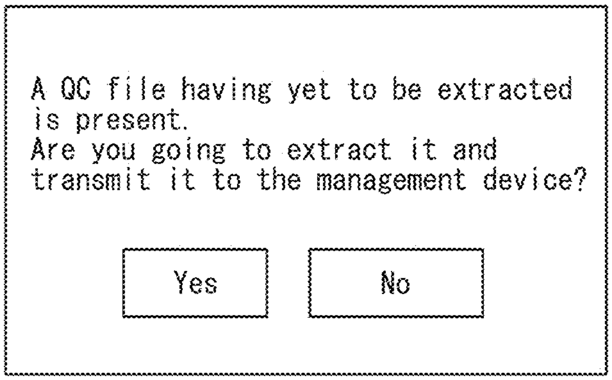
FIG. 19 shows an example of a screen for reporting that a quality control result having yet to be extracted is present.

FIG. 18 is a flowchart showing a modification of the flowchart shown in FIG. 14. The present modification further includes steps S171 to S174 in addition to the steps of the flowchart shown in FIG. 14. In a case where the input operation received in step S12 is an operation for starting "shutdown", the processor 26A executes the following steps before the shutdown process is performed. First, the processor 26A determines whether or not a quality control result having yet to be extracted is present in the quality control database 252 (S171). In a case where a quality control result having yet to be extracted is present (YES in S171), the processor 26A outputs, to the display/operation device 24, a screen for inquiring whether or not to extract the quality control result having yet to be extracted (S172). An example of this screen is shown in FIG. 19. In FIG. 19, "Yes" and "No" buttons are displayed together with a message that reports the presence of a quality control result (QC file) having yet to be extracted and that inquires of the user whether or not to transmit the quality control result to the management device. When an input operation for performing information extraction on the quality control result having yet to be extracted is received, i.e., when "Yes" is selected in the screen in FIG. 19 (YES in S173), the processor 26A executes the quality control information extraction process (S174) and then executes the shutdown process (S17). Steps S171 to S174 and step S17 may be executed concurrently. Through the concurrent execution, the processing time period can be made shorter than in a case where these steps are successively executed.

The analyzer 2 is inevitably shut down at the end of specimen measurement work every day. Therefore, when presence/absence of a quality control result having yet to be extracted is automatically checked with the trigger for the checking being shutdown as in the present modification, the quality control result can be prevented from being forgotten to be transmitted to the management device 4.

Figure 20:
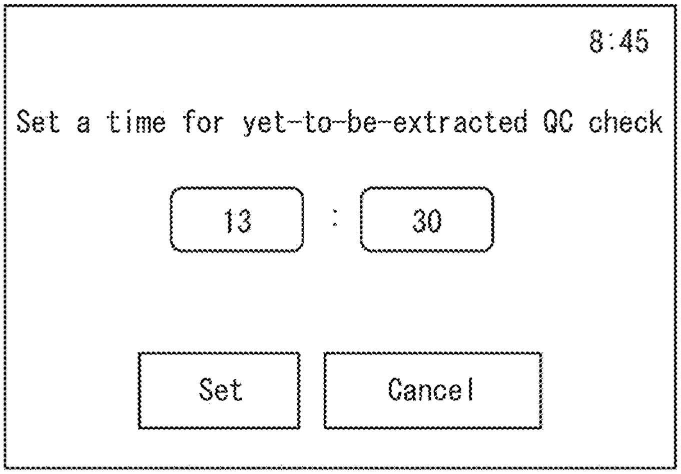
FIG. 20 shows an example of a screen for setting an automatic check time of automatically checking presence/absence of a quality control result having yet to be extracted.
Figure 21:
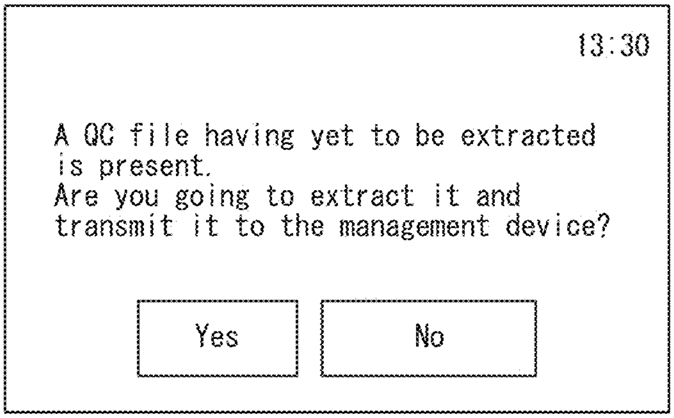
FIG. 21 shows an example of a confirmation screen outputted to the analyzer at the automatic check time having been set.

The trigger for the automatic check of presence/absence of a quality control result having yet to be extracted is not limited to shutdown. For example, an automatic check time may be capable of being arbitrarily set. FIG. 20 shows an example of a screen for setting an automatic check time. In the example shown in the drawing, the automatic check time is set to 13:30. FIG. 21 shows an example of a confirmation screen outputted to the display/operation device 24 at the automatic check time having been set. In the example shown in the drawing, the confirmation screen is outputted at 13:30 which is the automatic check time having been set in the screen shown in FIG. 20.

[Configuration Example of Terminal 3]

Figure 22:
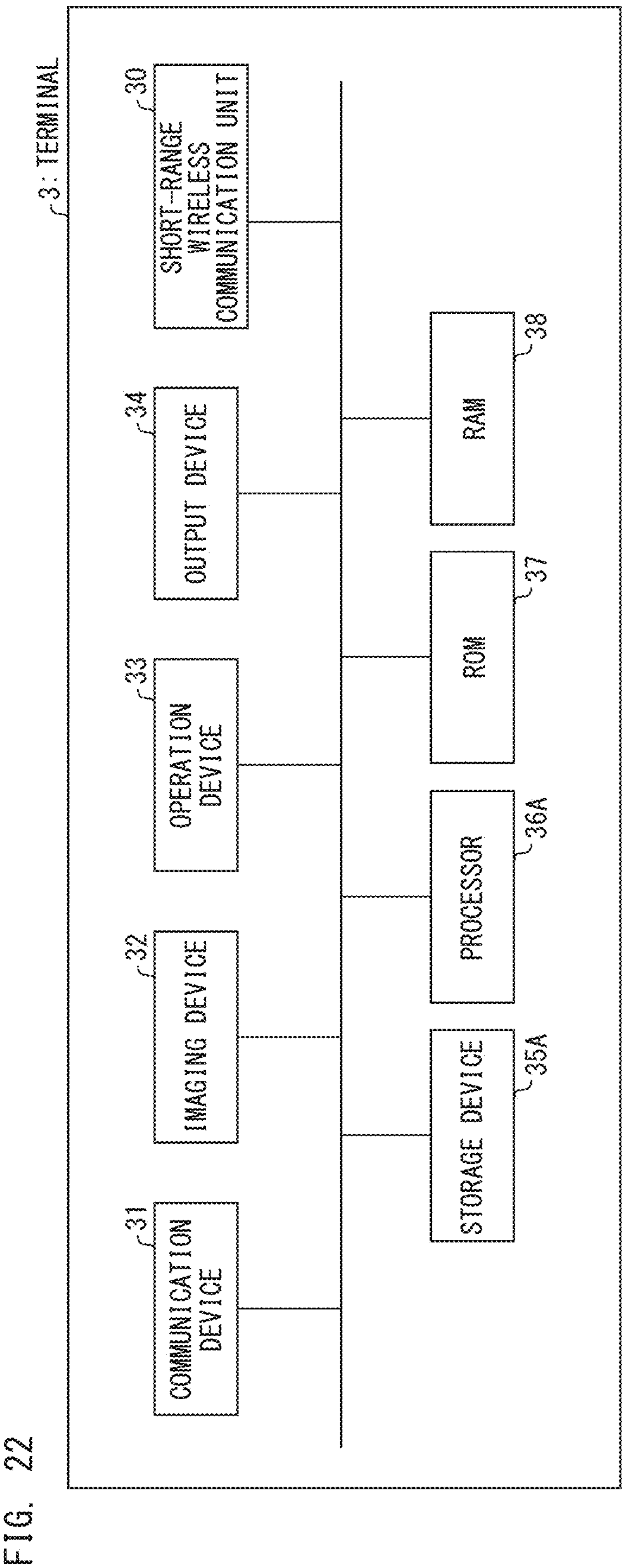
FIG. 22 shows a configuration example of a terminal.

As shown in FIG. 22, the terminal 3 according to the present embodiment includes, for example, a communication device 31, an imaging device 32, an operation device 33, an output device 34, a storage device 35A, a processor 36A, a RAM 37, a ROM 38, and the short-range wireless communication unit 30.

The communication device 31 is an interface for performing communication with the management device 4 via the communication network 5 according to control performed by the processor 36A. The imaging device 32 is, for example, a camera including an image sensor such as a charge coupled device (CCD). The imaging device 32 is mainly intended to image information codes. The operation device 33 receives operations, for various data, performed with respect to the terminal 3. The operation device 33 is, for example, a touch panel or a microphone. The output device 34 outputs various data processed by the terminal 3. The output device 34 is, for example, a touch panel. The short-range wireless communication unit 30 performs short-range wireless communication with the short-range wireless communication unit 20 of the analyzer 2.

Figure 23:
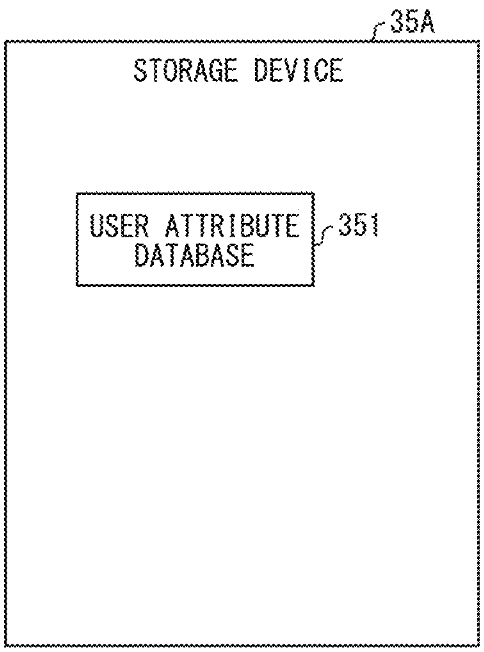
FIG. 23 shows a configuration example of a storage device of the terminal.

The storage device 35A is for storing therein various data and various programs to be used by the terminal 3 and is, for example, a semiconductor drive such as a solid-state drive or a magnetic disk such as a hard disk. The storage device 35A stores therein, for example, a user attribute database 351 as shown in FIG. 23.

Figure 24:
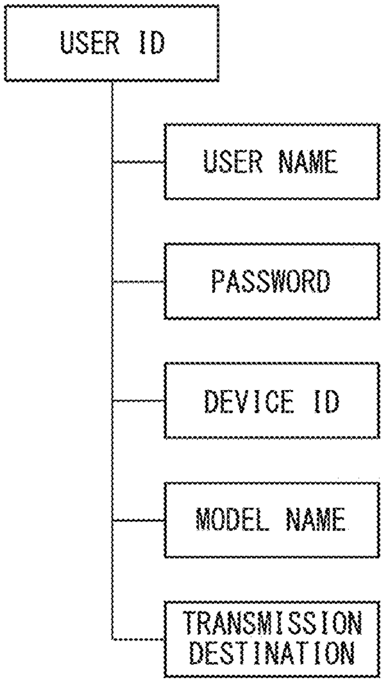
FIG. 24 shows an example of the data structure of a user attribute database.

The user attribute database 351 is a database for storing therein information about the health professional who is a user of the terminal 3 and is, for example, an RDB. FIG. 24 shows an example of a data structure in a case where the user attribute database 351 is an RDB. As shown in the drawing, the user attribute database 351 stores therein, for example, the following pieces of information (D51) to (D56) such that these pieces of information are associated with one another.

(D51) User ID: This is an identifier of the health professional.

(D52) User name: This is the name of the health professional.

(D53) Password: This is a password for the health professional to log in to the terminal 3.

(D54) Device ID: This is the identifier of the analyzer 2 associated with the health professional.

(D55) Model name: This is the model name of the analyzer 2 associated with the health professional.

(D56) Transmission destination: This is a transmission destination associated with the health professional. The transmission destination is, for example, a URL, an e-mail address, a communication address, or the like.

The processor 36A is a controller that comprehensively controls the functions of the terminal 3. The processor 36A is, for example, a CPU. The processor 36A may be implemented by, for example, a logic circuit. The processor 36A reads out an application 361A from the storage device 35A, loads the application 361A to the RAM 37, and executes the application 361A. The application 361A is stored in, for example, the storage device 35A as a program for causing a computer to function as a controller for executing various processes.

[Configuration Example of Application 361A]

Figure 25:
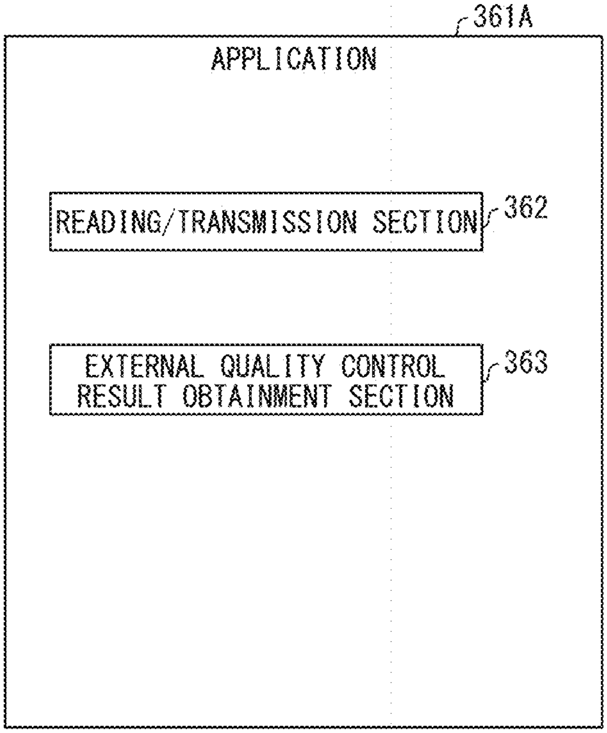
FIG. 25 shows a configuration example of an application that is operated in the terminal.

FIG. 25 shows a configuration example of the application 361A. The application 361A includes, for example, a reading/transmission section 362 and an external quality control result obtainment section 363.

When the operation device 33 receives an input operation for starting reading of an information code, the processor 36A executes an information code reading process according to an instruction from the reading/transmission section 362. In the information code reading process, the information code is imaged by the imaging device 32, and information is read from the imaged information code.

After the reading is completed, the processor 36A may cause the output device 34 to display the read information such that the health professional can check the information. In addition, after the reading is completed, the processor 36A may perform determination as to matchability of the read information according to an instruction from the reading/transmission section 362. Specifically, the processor 36A determines whether or not each of a model name and a device ID included in the read information matches the corresponding one of the model name and the device ID stored in the user attribute database 351. In the case of matching therebetween, the processor 36A transmits the read information to the management device 4. Thus, quality control results are transmitted to the management device 4. The destination for the transmission may be included in the read information or may be preset in the terminal 3. Regarding the timing for the transmission, the transmission may be performed automatically or may be performed at a timing of receiving an input operation. Meanwhile, in a case where at least one of the model name and the device ID does not match the corresponding one thereof, the processor 36A may cause the output device 34 to display a screen prompting the health professional to perform checking. Consequently, failure to select the appropriate analyzer 2, reading of a fake code, spoofing, and the like can be prevented.

In addition, the processor 36A obtains an external quality control result from the management device 4 according to an instruction from the external quality control result obtainment section 363. The processor 36A may obtain an external quality control result for the analyzer 2 identified with the device ID stored in the user attribute database 351 so as to be associated with the user ID of the health professional who has logged in to the terminal 3. The source from which an external quality control result is obtained may be a web page provided by the management device 4 or may be an e-mail transmitted from the management device 4, for example. The trigger for obtainment of an external quality control result may be reception, of an input operation, by the operation device 33 or may be arrival of a predetermined timing at which the external quality control result is automatically obtained.

[Example of Screen of Terminal 3]

Figure 26:
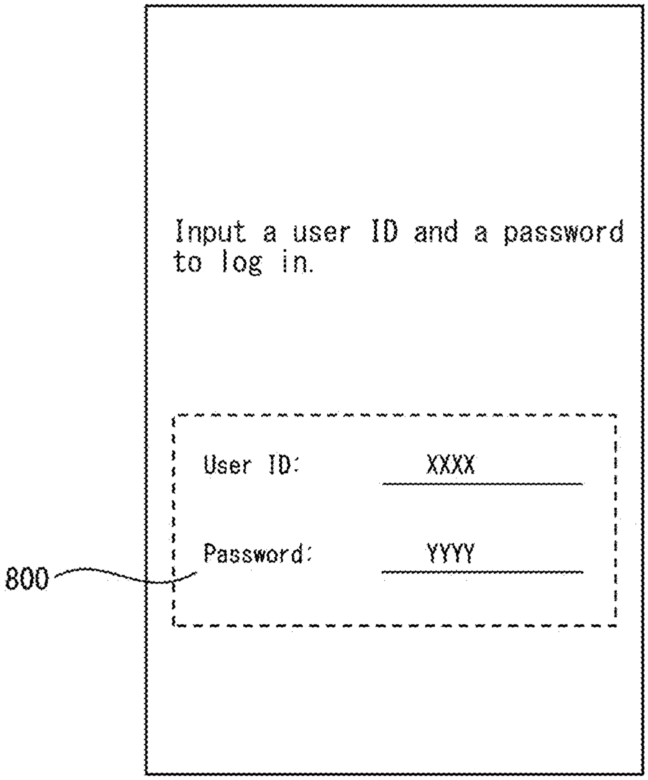
FIG. 26 shows an example of a login screen displayed on the terminal.

FIG. 26 shows an example of a login screen displayed on the output device 34. In a field 800, a user ID and a password are inputted.

Figure 27:
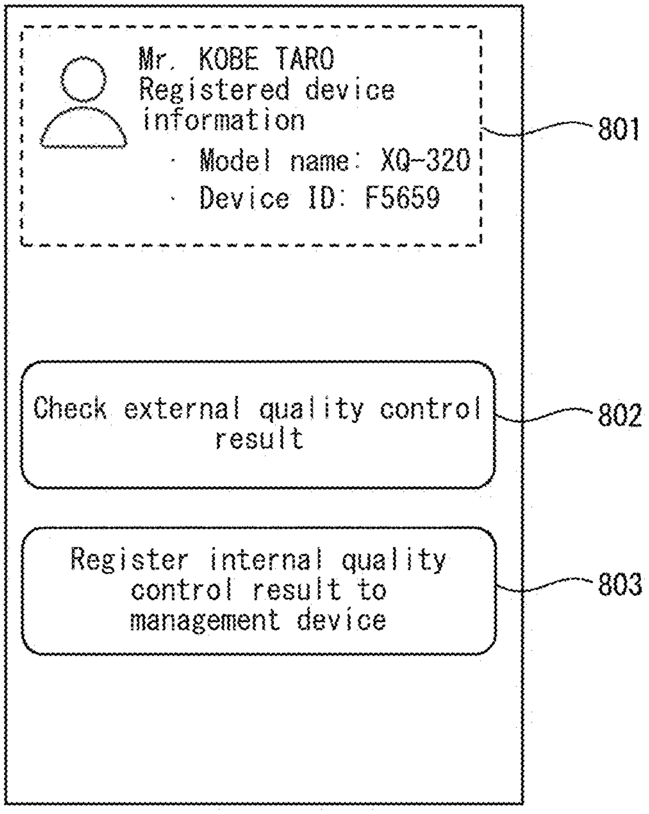

FIG. 27 shows an example of a menu screen displayed on the output device 34 after logging in. In a field 801, information about the user is displayed, for example. For example, the user name, the model name, and the device ID stored in the user attribute database 351 so as to be associated with the user ID of the health professional who has logged in, are displayed.

When an operation is received through a button 802, the processor 36A obtains an external quality control result according to an instruction from the external quality control result obtainment section 363.

Figure 28:
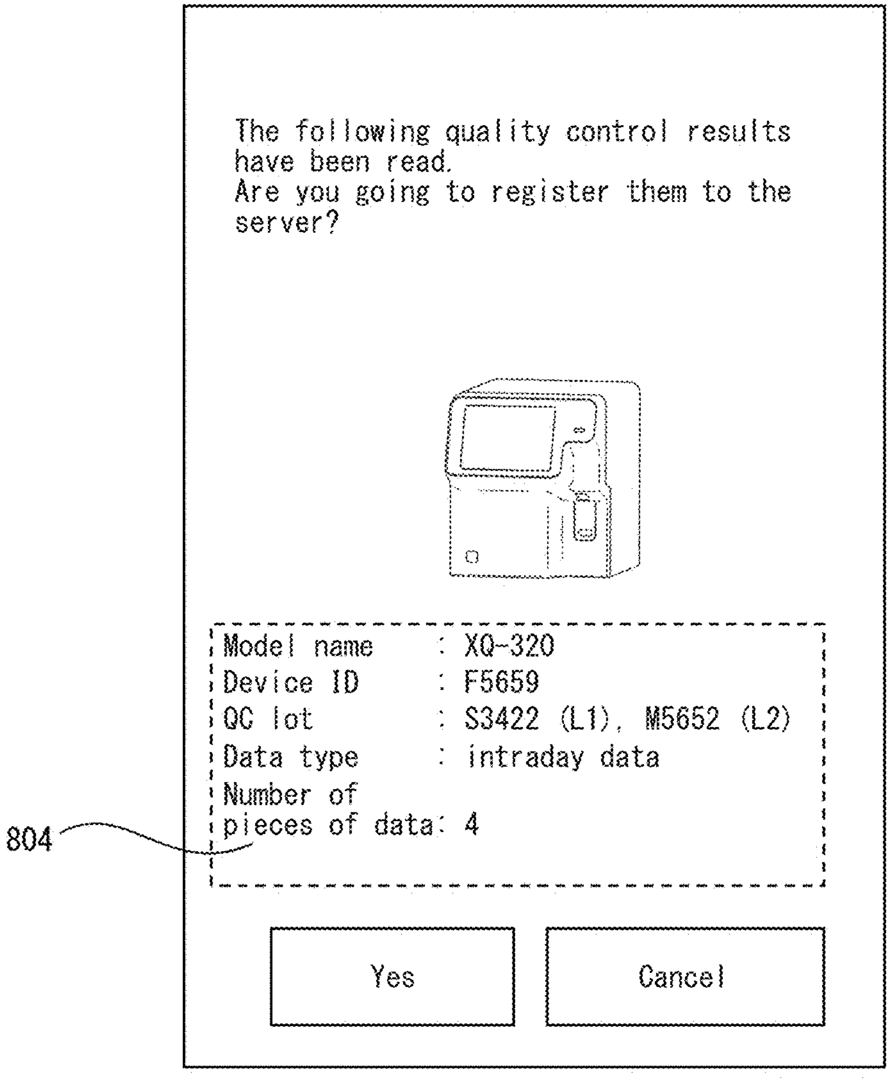
FIG. 28 shows an example of a screen displayed on the terminal after reading of the information code is completed.
Figure 29:
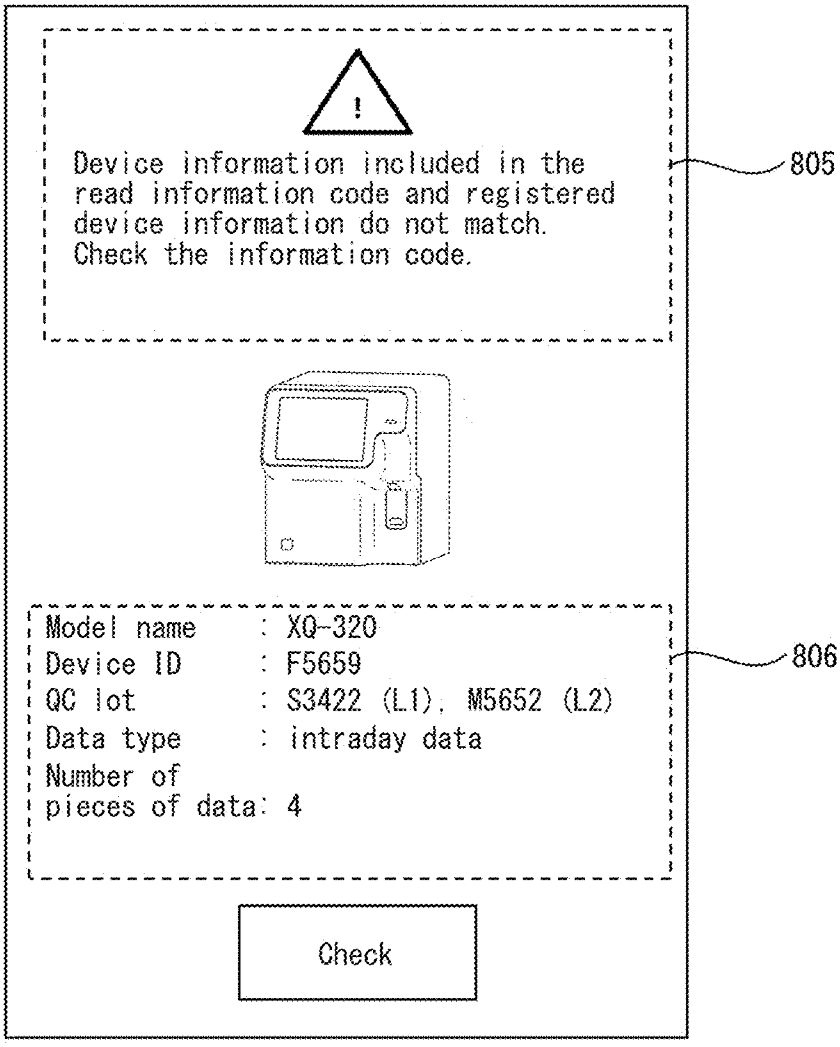
FIG. 29 shows another example of the screen displayed on the terminal after reading of the information code is completed.

When an operation is received through a button 803, the processor 36A executes the information code reading process according to an instruction from the reading/transmission section 362. FIG. 28 and FIG. 29 each show an example of a screen displayed on the output device 34 after the reading is completed. The example shown in FIG. 28 is an example of a screen in a case where the model name and the device ID match the corresponding ones thereof. In a field 804, the read information is displayed. Consequently, the health professional can check whether there is no insufficiency in the information to be transmitted. The example shown in FIG. 29 is an example of a screen in a case where the model name and the device ID do not match the corresponding ones thereof. In a field 805, a message prompting the health professional to perform checking is displayed. In a field 806, the read information is displayed.

[Configuration Example of Management Device 4]

Figure 30:
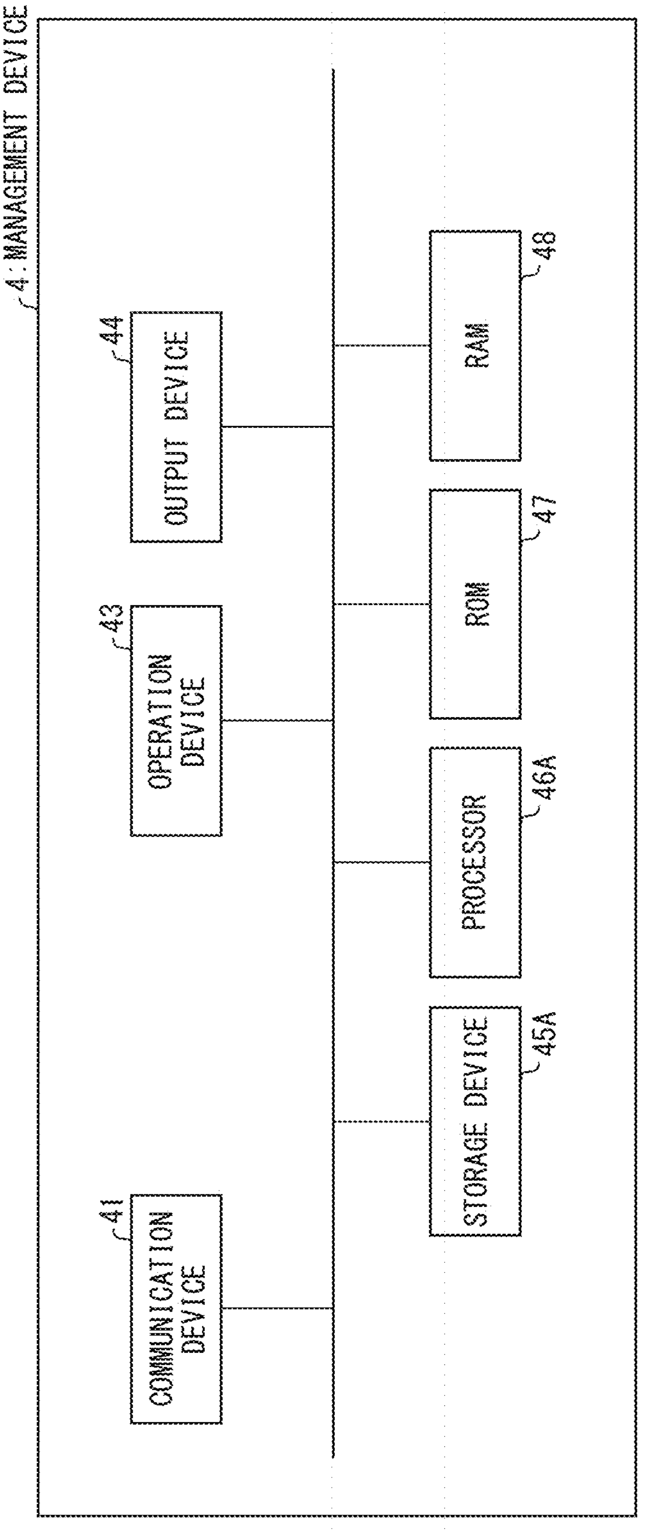
FIG. 30 shows a configuration example of a management device.
Figure 31:
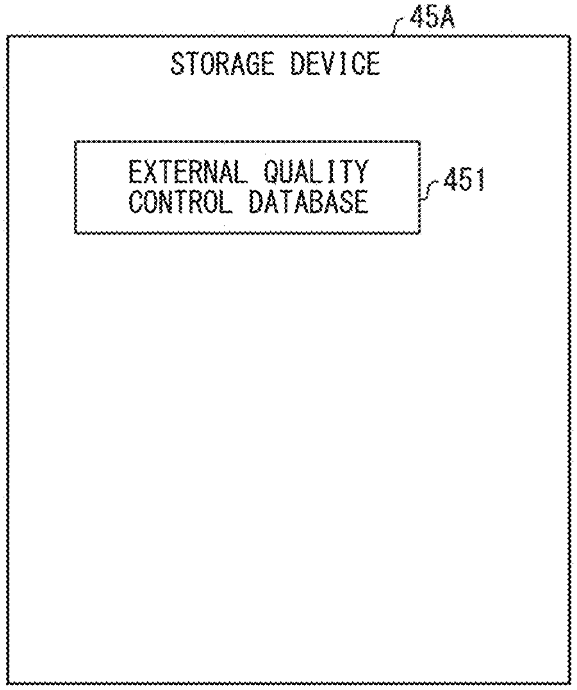
FIG. 31 shows a configuration example of a storage device of the management device.

As shown in FIG. 30, the management device 4 according to the present embodiment includes, for example, a communication device 41, an operation device 43, an output device 44, a storage device 45A, a processor 46A, a RAM 47, and a ROM 48. The communication device 41 is an interface for performing communication with the terminal 3 via the communication network 5 according to control performed by the processor 46A. The operation device 43 receives operations, for various data, performed with respect to the management device 4. The operation device 43 is, for example, a touch panel or a microphone. The output device 44 outputs various data processed by the management device 4. The output device 44 is, for example, a touch panel, a speaker, or a printer. The storage device 45A is for storing therein various data and various programs to be used by the management device 4 and is, for example, a semiconductor drive such as a solid-state drive or a magnetic disk such as a hard disk. As shown in FIG. 31, the storage device 45A stores therein, for example, an external quality control database 451. The external quality control database 451 manages, for each model of analyzer 2 and for each type of quality control specimen, information necessary for external quality control and external quality control results.

The processor 46A is a controller that comprehensively controls the functions of the management device 4. The processor 46A is, for example, a CPU. The processor 46A may be implemented by, for example, a logic circuit. The processor 46A reads out an application 461A from the storage device 45A, loads the application 461A to the RAM 47, and executes the application 461A. The application 461A is stored in, for example, the storage device 45A as a program for causing a computer to function as a controller for executing various processes.

[Configuration Example of Application 461A]

Figure 32:
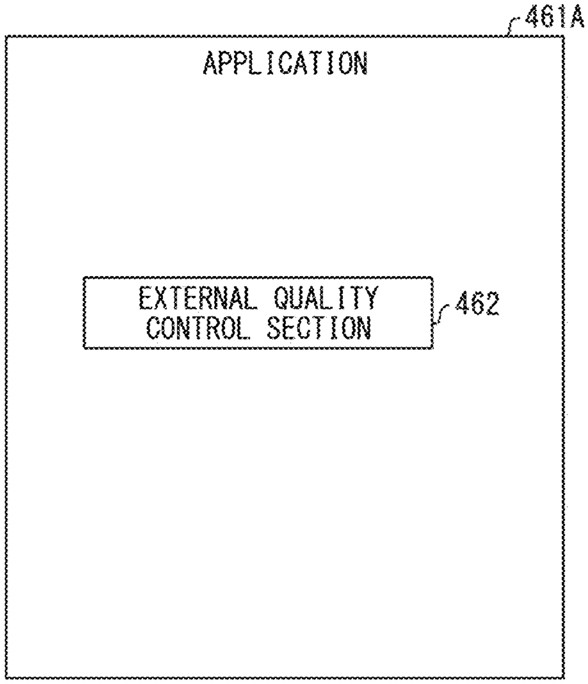
FIG. 32 shows a configuration example of an application that is operated in the management device.

FIG. 32 shows a configuration example of the application 461A. The application 461A includes, for example, an external quality control section 462. The processor 46A executes an external quality control process according to an instruction from the external quality control section 462. In the external quality control process, information transmitted from the terminal 3 is received and stored in the external quality control database 451, external quality control is performed upon arrival of a predetermined setting time or according to an input operation, and the result of the external quality control is provided to the medical facility.

[Example of Flow of Processing To Be Executed by Terminal 3 and Management Device 4]

Figure 33:
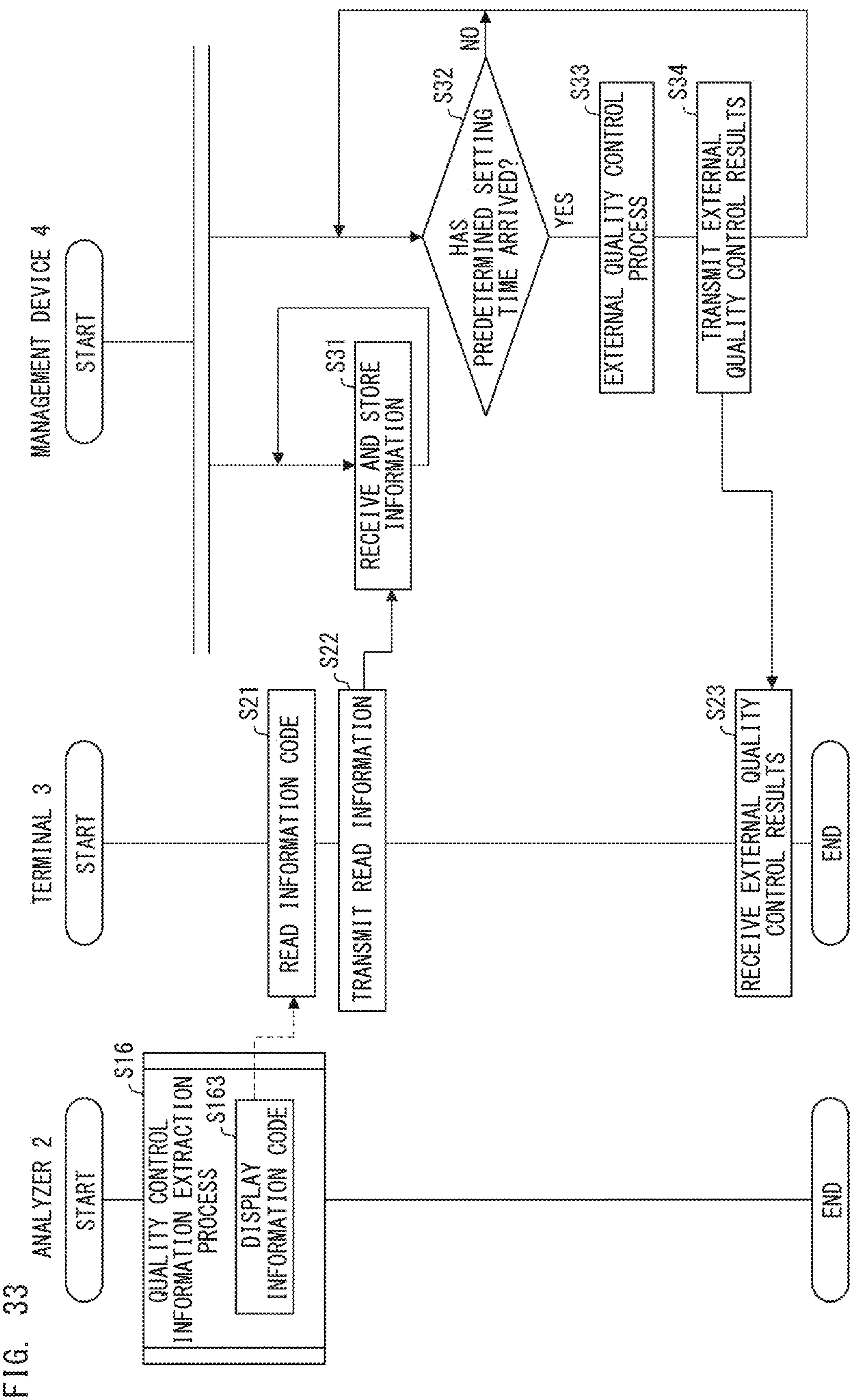
FIG. 33 is a flowchart showing an example of the flow of processing to be executed by the terminal and the management device.

FIG. 33 is a flowchart showing an example of the flow of processing to be executed by the terminal 3 and the management device 4. In a state where an information code is displayed on the analyzer 2 in step S163 described with reference to FIG. 17, the processor 36A of the terminal 3 executes the information code reading process such that the imaging device 32 of the terminal 3 reads the information code (S21, obtainment step). Then, the read information is transmitted to the management device 4 (S22, transmission step). The processor 46A of the management device 4 receives the information transmitted from the terminal 3 and stores the information in the external quality control database 451 (S31). When, for example, a predetermined setting time arrives (YES in S32), the processor 46A of the management device 4 performs aggregation of data regarding external quality control and determination (S33). The aggregation of data regarding external quality control is performed by, for example, calculating a statistical value (e.g., an average value or a median value) with measurement results regarding quality control specimens of the same lot being defined as a parent population, on the basis of external quality control data transmitted from a plurality of facilities to the management device 4 within an aggregation period. The processor 46A of the management device 4 determines, on the basis of the calculated statistical value, whether the external quality control results regarding the respective analyzers are normal or abnormal. For example, in a case where an individual quality control result falls within a range of 2SD about the overall average value, the processor 46A determines that the quality control result is normal. Meanwhile, in a case where an individual quality control result is outside the range of 2SD, the processor 46A determines that the quality control result is abnormal. The processor 46A of the management device 4 transmits the result of the aggregation and the result of the determination which have been thus obtained, to the terminal 3 as external quality control results (S34). The processor 36A of the terminal 3 receives the external quality control results (S23) and causes the output device 34 to display the external quality control results, for example.

[In Case of Immunoassay Device]

An immunoassay device will be described as another example of the analyzer 2. Examples of the immunoassay device include HISCL-5000 (manufactured by Sysmex Corporation). In immunoassay, the data amount of quality control results is larger than that in the case of a blood cell counter, and thus the quality control results might not be able to be completely recorded in an information code. In view of this drawback, relaying of information between the analyzer 2 and the terminal 3 is desirably performed by utilizing, instead of an information code, short-range wireless communication such as Bluetooth between the short-range wireless communication unit 20 and the short-range wireless communication 30. When short-range wireless communication is utilized, the volume and the number of types of data to be transmitted can be made larger than those in a case where an information code is utilized. Thus, for example, various pieces of information stored in the analyzer 2 such as data of calibration curves, various logs, error information, and status information stored in the analyzer 2 can be set as data to be transmitted.

Figure 34:
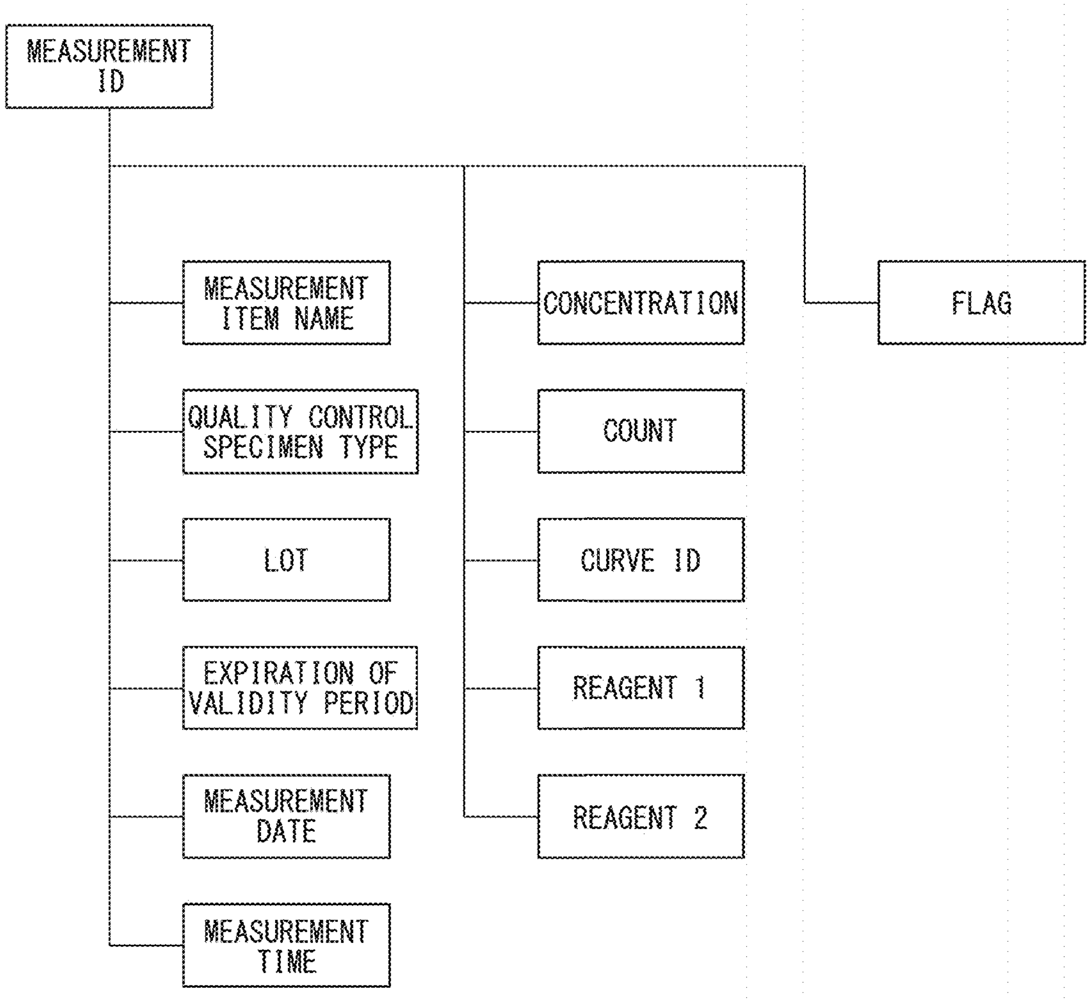
FIG. 34 shows an example of the data structure of a quality control database in a case where the analyzer is an immunoassay device.

FIG. 34 shows an example of the data structure of the quality control database 252 in a case where the analyzer 2 is an immunoassay device. The quality control database 252 shown in the drawing stores therein, for example, the following pieces of information (D61) to (D73) such that these pieces of information are associated with one another. The maximum number of the types of measurement items indicated in the following piece of information (D62) is, for example, 24. Thus, the data amount of quality control results is larger than that in the case of blood cell counting. For example, in a case where the number of the types of the measurement items is the maximum number (i.e., 24), the number of the types of the concentration levels of quality control specimens is two, and quality control measurement is performed twice per day, 96 (=24×2×2) records are stored in the quality control database 252 as quality control results for one day.

(D61) Measurement ID: This is an identifier of quality control measurement.

(D62) Measurement item: This is the item name of the quality control measurement. Examples of the measurement item are "FLUA" (influenza A) and "FLUB" (influenza B).

(D63) Quality control specimen type: This is a type indicating the concentration level of a quality control specimen used for the quality control measurement. Examples of the quality control specimen type are "FLU-L1" (level 1), "FLU-L2" (level 2), and "FLU-L3" (level 3).

(D64) Lot: This is the lot number of the quality control specimen used for the quality control measurement.

(D65) Expiration of validity period: This is the expiration of validity period of the quality control specimen used for the quality control measurement.

(D66) Measurement date: This is the date of execution of the quality control measurement.

(D67) Measurement time: This is the time of execution of the quality control measurement. The measurement date and the measurement time may be combined as one item.

(D68) Concentration: This is the concentration of the quality control specimen, which is one of quality control results. Conversion into this concentration is performed by applying a count value (described later) to a calibration curve.

(D69) Count: This is a count value which is one of the quality control results. The count value is an optical feature value detected by an optical detector (e.g., a photomultiplier tube) provided in the immunoassay device and is proportional to the amount of an analyte contained in the quality control specimen. In the case of a photomultiplier tube, the count value is the number of detected photons.

(D70) Curve ID: This is an identifier indicating a calibration curve.

(D71) Reagent 1: This is the type of a reagent having been used.

(D72) Reagent 2: This is the type of a reagent having been used.

(D73) Flag: This is a flag indicating whether or not the quality control results have been extracted.

FIG. 35 shows a specific example of records in the quality control database 252 in the case where the analyzer 2 is an immunoassay device. The drawing shows four records. The two records on the upper side indicate quality control results obtained by using quality control specimens with the quality control specimen type being FLU-L1, with the lot being J337, and with the expiration of validity period being Apr. 17, 2023. The dates and the times of execution of the quality control measurements are, in order from the upper record, 07:53:28 on Apr. 11, 2023 and 19:43:36 on the same date. The two records on the lower side indicate quality control results obtained by using quality control specimens with the quality control specimen type being FLU-L2, with the lot being J882, and with the expiration of validity period being Apr. 17, 2023. The dates and the times of execution of the quality control measurements are, in order from the upper record, 07:54:33 on Apr. 11, 2023 and 19:44:22 on the same date.

In the quality control information extraction process executed by the processor 26A, quality control results satisfying an extraction condition are obtained from the quality control database 252, and one or more pieces of transmission data including each of the obtained quality control results or a value (a statistical value or the like) calculated on the basis of these quality control results are created (preparation step). Then, the created pieces of transmission data are transmitted to the terminal 3 via the short-range wireless communication unit 20. The processor 36A of the terminal 3 receives these pieces of transmission data via the short-range wireless communication unit 30 (obtainment step).

Figure 36:
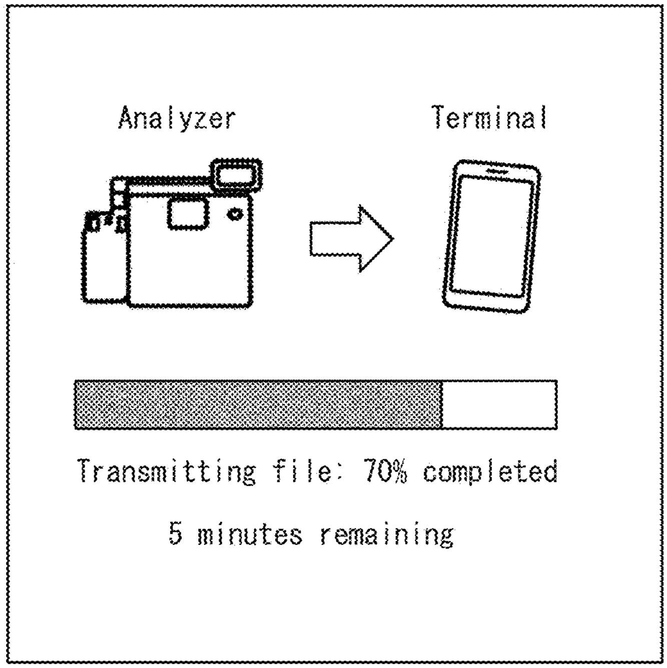
FIG. 36 shows an example of a screen showing the extent of progress in transmission of a quality control result through short-range wireless communication.

During the period of transmission of the quality control results through short-range wireless communication, a screen showing the extent of progress in the transmission is desirably displayed on the display/operation device 24. An example of the screen showing the extent of progress is shown in FIG. 36. In the drawing, the extent of progress is displayed in the form of a progress bar, and the proportion of progress and the time period required for completing the transmission are displayed. When the extent of progress is displayed in this manner, the health professional can perform other work while checking the extent of progress.

Embodiment 2

The same constituents and steps as those described in embodiment 1 are denoted by the same reference characters, and descriptions thereof are omitted.

The present embodiment will be described as an embodiment in which an instruction inputted with use of a management device 4 by the service staff member is transmitted via a terminal 3 to an analyzer 2. In the present embodiment, the service staff member allows the analyzer 2 to execute a process without performing communication with the health professional by telephone or the like and without visiting the medical facility. Consequently, the service staff member can efficiently and swiftly perform maintenance/running and the like. In addition, the health professional who relays the instruction can cause the analyzer 2 to execute a process without any erroneous operation through only a simple operation of getting an information code to be read. That is, even though the service staff member does not visit the medical facility and even though the health professional is not proficient in handling of the analyzer 2, actions (e.g., restoration from an error, various settings, and the like) for the analyzer 2 can be easily taken.

[Configuration Example of Management Device 4]

Figure 37:
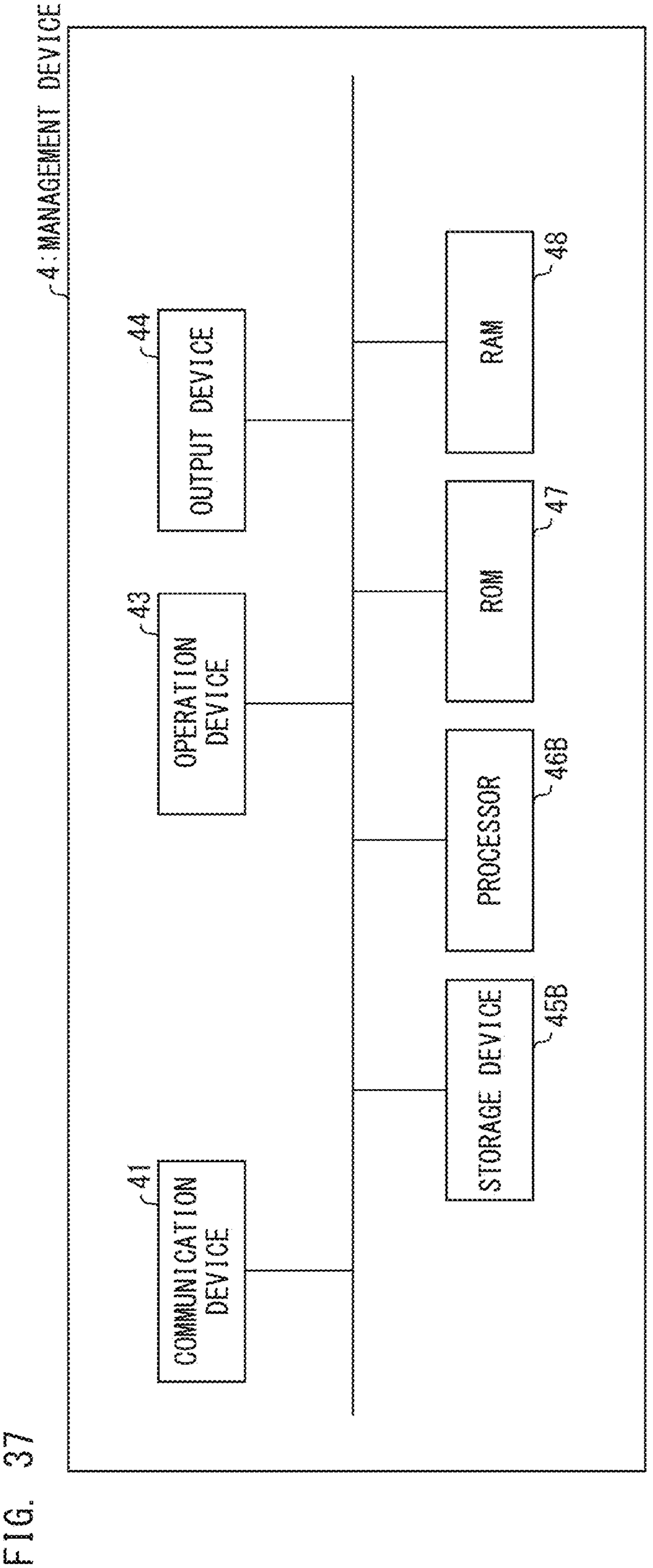
FIG. 37 shows a configuration example of a management device.

As shown in FIG. 37, the management device 4 according to the present embodiment has the same configuration as that of the management device 4 in embodiment 1, except that a storage device 45B and a processor 46B are provided instead of the storage device 45A and the processor 46A.

Figure 38:
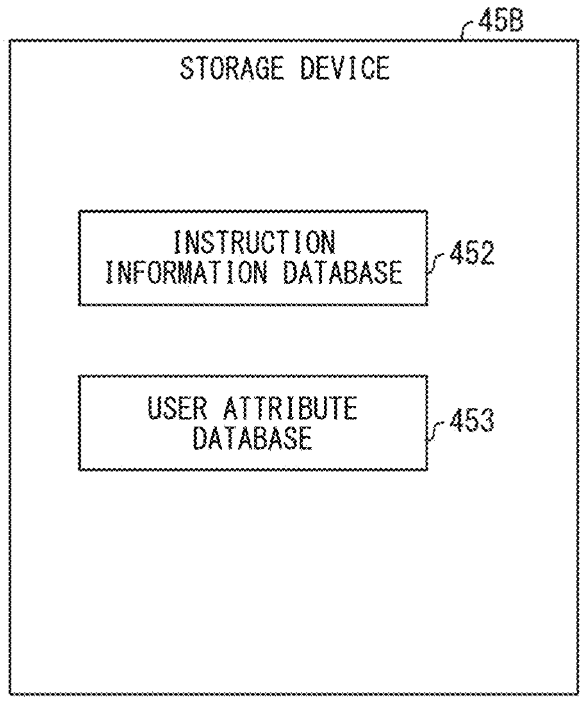
FIG. 38 shows a configuration example of a storage device of the management device.

The storage device 45B is for storing therein various data and various programs to be used by the management device 4 and is, for example, a semiconductor drive such as a solid-state drive or a magnetic disk such as a hard disk. As shown in FIG. 38, the storage device 45B stores therein, for example, an instruction information database 452 and a user attribute database 453.

The instruction information database 452 is a database for storing therein information about instructions directed to the analyzer 2 and the health professional who handles the analyzer 2. The instruction information database 452 is, for example, an RDB. The instructions are the following items (IN1) and (IN2).

(IN1) Command Directed to Analyzer 2

Commands to be stored in the instruction information database 452 are all of commands capable of being executed in each of a user mode and a service mode (a mode in which only the service staff member can log in) in the analyzer 2. When the analyzer 2 is caused, via the terminal 3, to execute a command capable of being executed in the service mode, actions for the analyzer 2 can be taken without the service staff member visiting the medical facility. Examples of the commands are commands to: perform clogging elimination; perform consecutive blank check; turn off a blood suction sensor; perform shutdown; perform shutdown and restart; read out error histories; read out quality control histories; read out service data; set service data (e.g., enable or disable screen locking, enable or disable a reporting function (e.g., a function of reporting the amount of a remaining reagent), set automatic wake-up, set automatic shutdown, and perform another kind of setting); and reset service setting. The command capable of being executed only in the service mode is, for example, a command to perform consecutive blank check. The commands to perform clogging elimination and consecutive blank check are for dealing with clogging in an RBC detector, and the command to turn off the blood suction sensor is for dealing with sample shortage (insufficiency in the amount of blood). The consecutive blank check is a function of repeating blank check until a blank value becomes smaller than a threshold value. The screen locking is a function of, in cases such as a case where an operator stays away from the analyzer 2, preventing another operator from performing any operation on the analyzer 2.

(IN2) Instruction Directed to Health Professional

This is an instruction regarding work or the like desired to be performed by the health professional. An example of the instruction is an instruction to perform quality control measurement.

Figure 39:
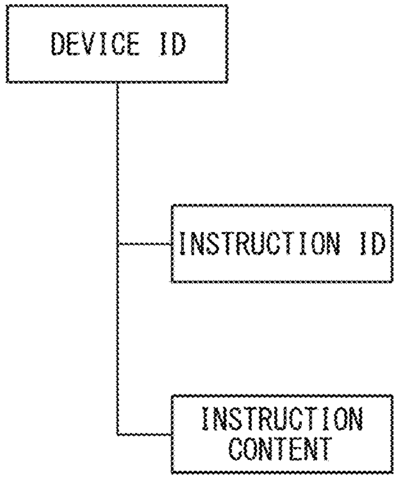
FIG. 39 shows an example of the data structure of an instruction information database.

FIG. 39 shows an example of a data structure in a case where the instruction information database 452 is an RDB. As shown in the drawing, the instruction information database 452 stores therein, for example, the following pieces of information (D81) to (D83) such that these pieces of information are associated with one another.

- (D81) Device ID: This is the identifier of the analyzer 2.
- (D82) Instruction ID: This is an identifier of an instruction. Specifically, the instruction ID is either of an identifier of a command and an identifier of an instruction directed to the health professional. The instruction ID is desirably an ID system that enables identification of both the command and the instruction. The instruction ID is composed of a combination of characters or numerals, and the number of the digits thereof is desirably small.
- (D83) Instruction content: This is content of the instruction.

FIG. 40 shows a specific example of records in the instruction information database 452. In the drawing, instructions regarding an analyzer 2 having a device ID of "F5659" are presented as examples.

Figure 41:
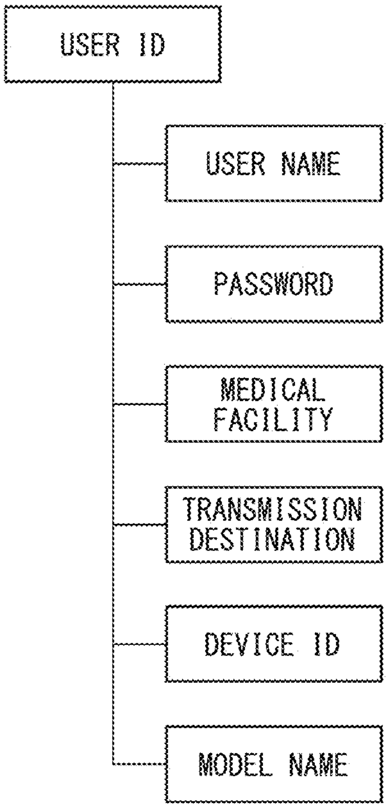
FIG. 41 shows an example of the data structure of a user attribute database.

The user attribute database 453 is a database for storing therein information about the service staff member who is a user of the management device 4. The user attribute database 453 is, for example, an RDB. FIG. 41 shows an example of a data structure in a case where the user attribute database 453 is an RDB. As shown in the drawing, the user attribute database 453 stores therein, for example, the following pieces of information (D91) to (D97) such that these pieces of information are associated with one another.

- (D91) User ID: This is an identifier of the service staff member.
- (D92) User name: This is the name of the service staff member.
- (D93) Password: This is a password for the service staff member to log in to the management device 4.
- (D94) Medical facility: This is the name of the medical facility in which the analyzer 2 associated with the service staff member is installed.
- (D95) Transmission destination: This is information indicating the transmission destination of data to be transmitted from the service staff member to the health professional. This information is, for example, a communication address of the terminal 3.
- (D96) Device ID: This is the identifier of the analyzer 2 associated with the service staff member.
- (D97) Model name: This is the model name of the analyzer 2 associated with the service staff member.

With reference back to FIG. 37, the processor 46B is a controller that comprehensively controls the functions of the management device 4. The processor 46B is, for example, a CPU. The processor 46B may be implemented by, for example, a logic circuit. The processor 46B reads out an application 461B from the storage device 45B, loads the application 461B to the RAM 47, and executes the application 461B. The application 461B is stored in, for example, the storage device 45B as a program for causing a computer to function as a controller for executing various processes.

[Configuration Example of Application 461B]

Figure 42:
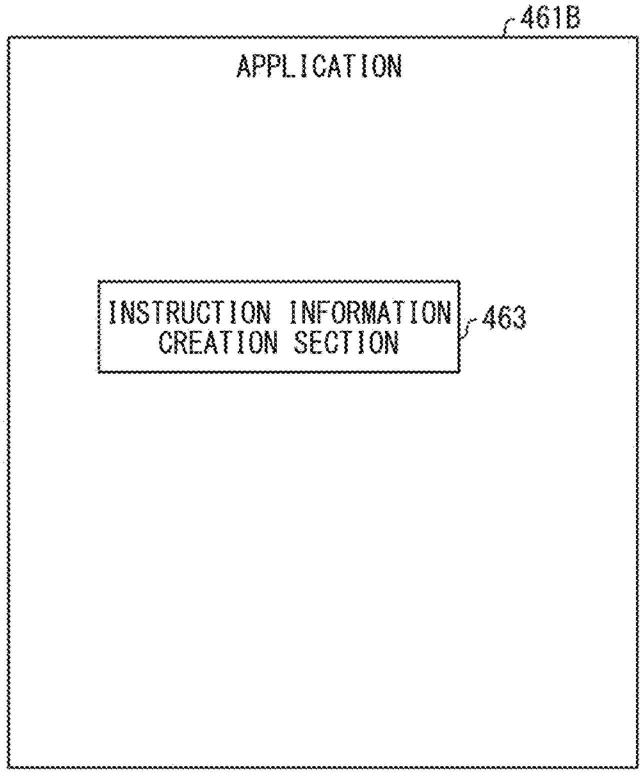
FIG. 42 shows a configuration example of an application that is operated in the management device.

FIG. 42 shows a configuration example of the application 461B. The application 461B includes, for example, an instruction information creation section 463.

Figure 43:
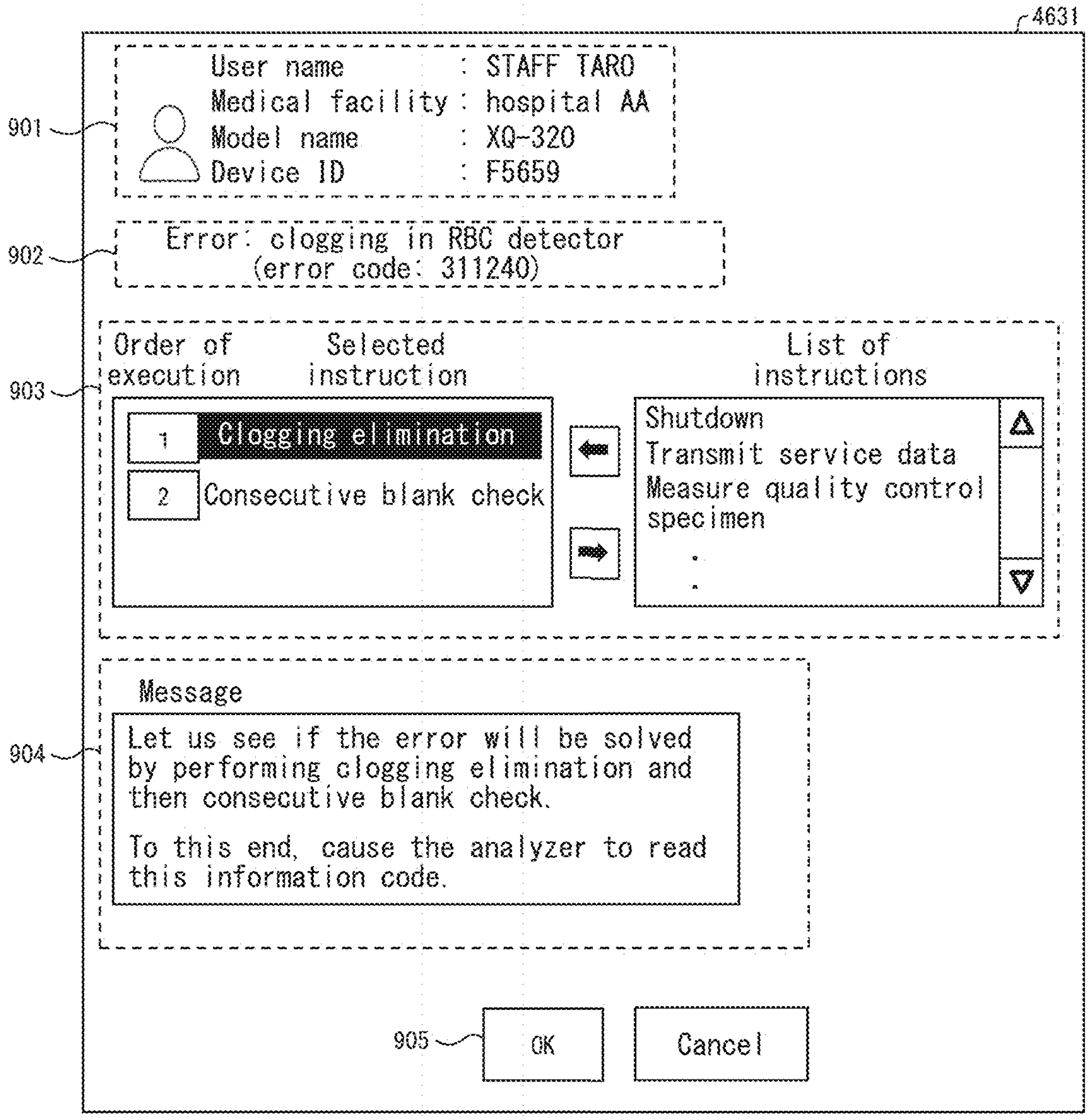
FIG. 43 shows an example of an instruction information creation screen.

The processor 46B generates an instruction information creation screen 4631 according to an instruction from the instruction information creation section 463 and causes the output device 44 to display the instruction information creation screen 4631. The instruction information creation screen 4631 is a screen for creating instruction information. FIG. 43 shows an example of the instruction information creation screen 4631. As shown in FIG. 43, the instruction information creation screen 4631 includes, for example, fields 901 to 904 and a button 905.

In the field 901, information about the user who has logged in to the management device 4 is displayed, for example. The information to be displayed in the field 901 is obtained from the user attribute database 453.

In the field 902, the status of the analyzer 2 is displayed, for example. In the example in the drawing, the text "clogging in RBC detector" is displayed as the status of the analyzer 2. The status to be displayed may be a status transmitted from the terminal 3 having read an information code in which the status of the analyzer 2 is recorded (see embodiment 3 described later), or may be a status that the service staff member has been told by the health professional and that the service staff member has inputted through the operation device 43.

The field 903 receives selection of instructions and the order of execution of the selected instructions. Instructions as selection candidates are obtained from the instruction information database 452. In the example shown in the drawing, two commands which are "clogging elimination" and "consecutive blank check" have been selected as instructions, with "clogging elimination" being the first command (being of the highest priority) in the order of execution and with "consecutive blank check" being the second command (being of the second highest priority) in the order of execution. In this manner, the service staff member can select desired instructions in the instruction information creation screen 4631. In addition, in a case where the service staff member desires to cause successive execution of a plurality of commands as instructions directed to the analyzer 2, the service staff member can collectively select the plurality of desired commands in the instruction information creation screen 4631 and specify the order of execution of these commands. Therefore, the service staff member can collectively give instructions to execute respective commands that the health professional would have to cause the analyzer 2 to sequentially execute one by one. Furthermore, effective troubleshooting and the like can be performed.

The field 904 receives input of a message regarding the selected instruction. The message is, for example, a message regarding a process to be executed by the analyzer 2, a message of which the health professional is to be informed, a message regarding an action to be taken by the health professional, etc. For each of the instructions, a predetermined message may be displayed in the field 904 in an editable manner.

When an operation is received through the button 905, the processor 46B creates, according to an instruction from the instruction information creation section 463, data (written as instruction data) including the information inputted in the fields 903 and 904 and transmits the created instruction data to the terminal 3. The transmission destination is obtained from the user attribute database 453.

An example of the information included in the instruction data is indicated as the following items (D101) to (D104). (D101) is an indispensable item, and (D102) to (D104) are optional items.

(D101) This is composed of: instruction IDs of the instructions selected in the field 903; and order information indicating the order of execution of these instructions. The arrangement order of the instruction IDs in the instruction data may be regarded as the order information, or data indicating the order information may be included.

(D102) This is the message inputted in the field 904.

(D103) This is the device ID and/or the model name of the analyzer 2 to which the instructions are directed. These pieces of information can be used for preventing failure to select the appropriate analyzer 2 to which the instructions are directed.

(D104) This is the date and the time of issuance and/or the expiration of validity period of the instruction data. The date and the time of issuance are the date and the time of creation of the instruction data, and the expiration of validity period is a timing at the end of a predetermined time period (e.g., 30 minutes) from the date and the time of issuance. These pieces of information can be used for preventing the instruction data from being used in a shared manner or in an unauthorized manner.

[Configuration Example of Terminal 3]

Figure 44:
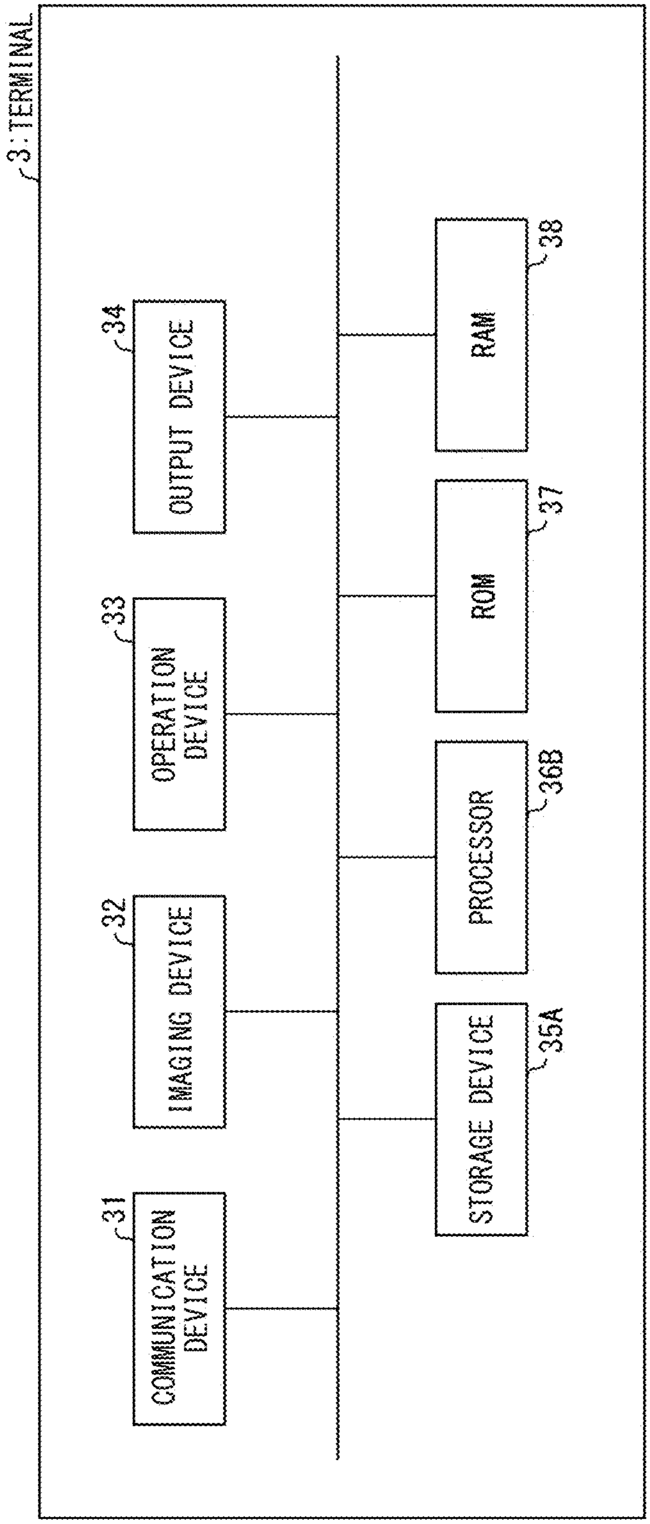
FIG. 44 shows a configuration example of a terminal.

As shown in FIG. 44, the terminal 3 according to the present embodiment has the same configuration as that of the terminal 3 in embodiment 1, except that a processor 36B is provided instead of the processor 36A.

The processor 36B is a controller that comprehensively controls the functions of the terminal 3. The processor 36B is, for example, a CPU. The processor 36B may be implemented by, for example, a logic circuit. The processor 36B reads out an application 361B from the storage device 35A, loads the application 361B to the RAM 37, and executes the application 361B. The application 361B is stored in, for example, the storage device 35A as a program for causing a computer to function as a controller for executing various processes.

[Configuration Example of Application 361B]

Figure 45:
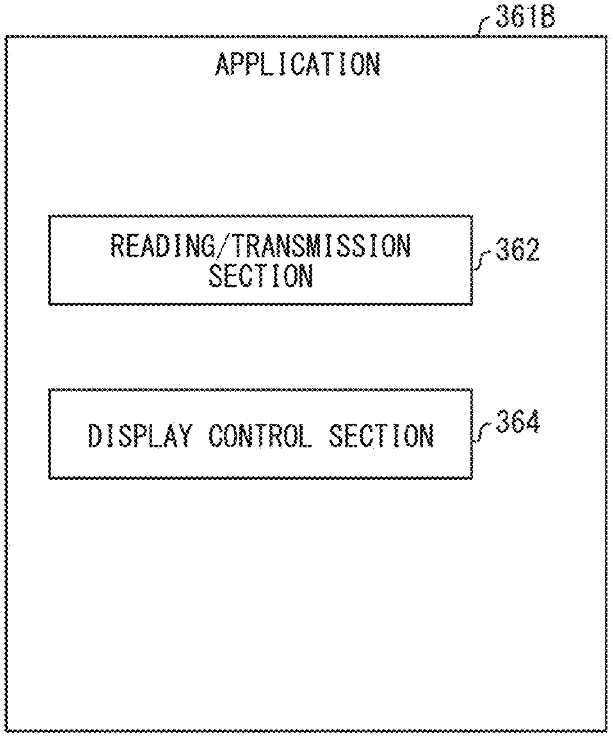
FIG. 45 shows a configuration example of an application that is operated in the terminal.

FIG. 45 shows a configuration example of the application 361B. The application 361B includes, for example, the reading/transmission section 362 and a display control section 364.

When the instruction data is received from the management device 4, the processor 36B executes a display control process according to an instruction from the display control section 364. In the display control process, the following "(Display control process 1)" and "(Display control process 2)" are executed.

(Display control process 1) This is a process of, in a case where an instruction ID included in the instruction data is an identifier of a command, creating an information code that allows the command to be read, and causing the output device 34 to display the created information code.

(Display control process 2) This is a process of, in a case where an instruction ID included in the instruction data is an identifier of an instruction directed to the health professional, causing the output device 34 to display a screen corresponding to the instruction ID.

[Example of Screen and Example of Information Code]

Figure 46:
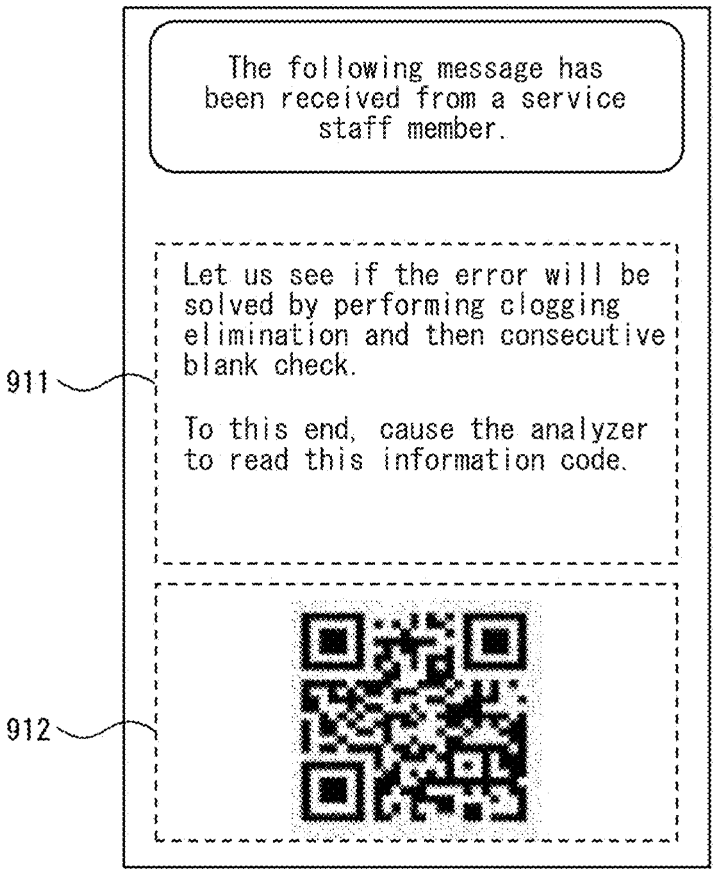
FIG. 46 shows an example of a screen displayed on the terminal, specifically, shows a screen displayed when instruction data including data for performing clogging elimination and consecutive blank check has been received.

FIG. 46 shows an example of a screen displayed through the display control process 1, specifically, shows a screen displayed when instruction data including instruction IDs "B1002" (for performing clogging elimination) and "B1003" (for performing consecutive blank check) has been received.

In a field 911, a message is displayed. This message is the message inputted in the instruction information creation screen 4631 shown in FIG. 43. By thus displaying the message, it becomes possible to, for example, notify the health professional of the content of the instruction and let the health professional know an action to be taken other than the action of causing the analyzer 2 to read an information code. Consequently, troubleshooting and the like can be assuredly performed.

In a field 912, an information code is displayed. This information code is an information code for causing "clogging elimination" and "consecutive blank check" selected in the instruction information creation screen 4631 shown in FIG. 43 to be executed in this order. Information recorded in the information code is as indicated by, for example, the following pieces of information (D111) to (D116). Data obtained by setting the format of these pieces of information to a CSV format is recorded in the information code.

(D111) First code type: An example thereof is "Instruction".

(D112) Second code type: This is unused. An example thereof is a NULL value.

(D113) Date-and-time information: This is the date-and-time information (the date and the time of issuance and/or the expiration of validity period) included in the instruction data.

(D114) Model name: This is the model name included in the instruction data.

(D115) Device ID: This is the identifier, of the analyzer 2, included in the instruction data.

(D116) Data body: This is the one or more instruction IDs included in the instruction data.

A specific example of data recorded in the information code is described as follows:

"Instruction,2023/04/11 17:59:22, XQ-320,F5659,B1002, B1003".

In this specific example, a first code type "Instruction", a second code type "NULL value", the date-and-time information "17:59:22 on Apr. 11, 2023", the model name "XQ-320", the device ID "F5659", and instruction IDs "B1002" and "B1003" are recorded in a CSV format. Since the character string "Instruction" is stored as a first code type, the analyzer 2 recognizes that the information code includes an instruction. The model name and the device ID are used for ascertaining that the instruction is directed to the analyzer 2. In a case where the model name and the device ID included in the read information code do not match the model name and the device ID stored in the analyzer 2, the analyzer 2 gives an indication that there is an error. The recording order of the instruction IDs indicates the order of execution. Since "B1002" (for performing clogging elimination) and "B1003" (for performing consecutive blank check) are recorded in this order, the analyzer 2 having read the information code executes the commands in this order. The analyzer 2 having read the information code shown in the example in FIG. 46 executes clogging elimination and then executes consecutive blank check. Even in a case where a plurality of processes are executed by the analyzer 2 in this manner, the information code has to be read only once. That is, the information code does not have to be read by the analyzer 2 many times, and thus the operation to be performed by the health professional is simplified.

Figure 47:
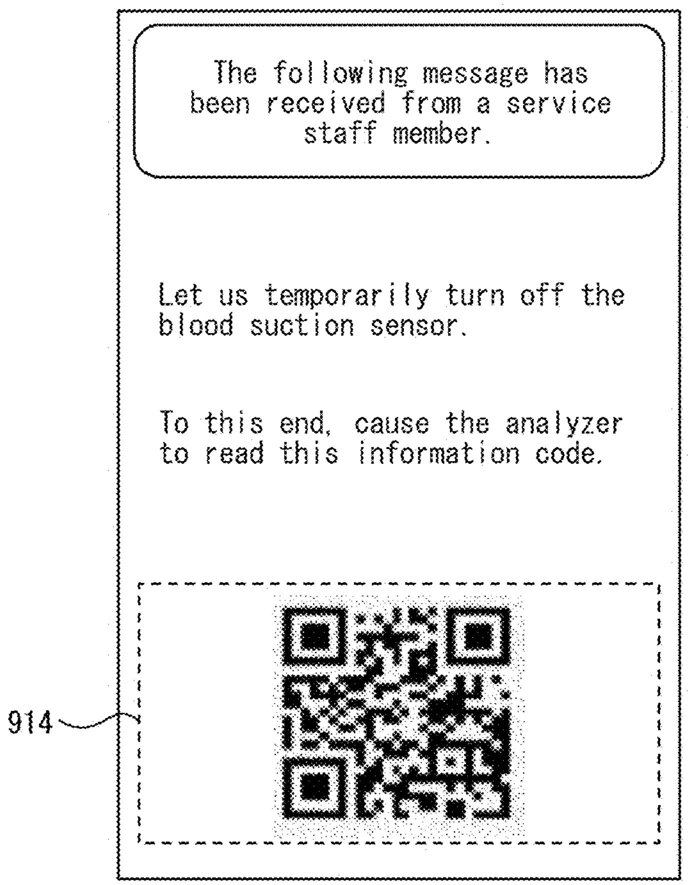
FIG. 47 shows another example of the screen displayed on the terminal, specifically, shows a screen displayed when instruction data including data for turning off a blood suction sensor has been received.

FIG. 47 shows another example of the screen displayed through the display control process 1, specifically, shows a screen displayed when instruction data including an instruction ID "S4099" (for turning off the blood suction sensor) has been received. In a field 914, an information code for executing a process of turning off the blood suction sensor of the analyzer 2 is displayed. A specific example of data recorded in the information code is described as follows:

"Instruction,2023/04/11 17:59:22, XQ-320,F5659, S4099".

In this specific example, the first code type "Instruction", the second code type "NULL value", the date-and-time information "17:59:22 on Apr. 11, 2023", the model name "XQ-320", the device ID "F5659", and an instruction ID "S4099" (for turning off the blood suction sensor) are recorded in a CSV format. When reading this information code, the analyzer 2 performs switching so as to turn off the blood suction sensor.

Figure 48:
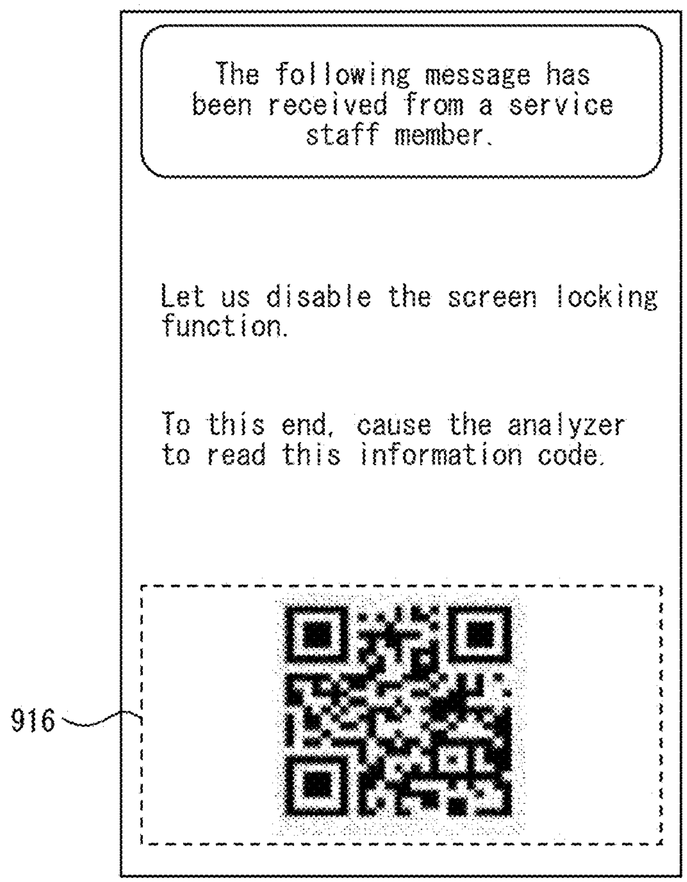
FIG. 48 shows another example of the screen displayed on the terminal, specifically, shows a screen displayed when instruction data including data for disabling screen locking has been received.

FIG. 48 shows another example of the screen displayed through the display control process 1, specifically, shows a screen displayed when instruction data including an instruction ID "S1181" (for disabling screen locking) has been received. In a field 916, an information code for executing a process of disabling screen locking of the analyzer 2 is displayed. A specific example of data recorded in the information code is described as follows:

"Instruction,2023/04/11 17:59:22, XQ-320,F5659, S1181".

In this specific example, the first code type "Instruction", the second code type "NULL value", the date-and-time information "17:59:22 on Apr. 11, 2023", the model name "XQ-320", the device ID "F5659", and an instruction ID "S1181" (for disabling screen locking) are recorded in a CSV format. When reading this information code, the analyzer 2 performs switching so as to disable the screen locking function.

Figure 49:
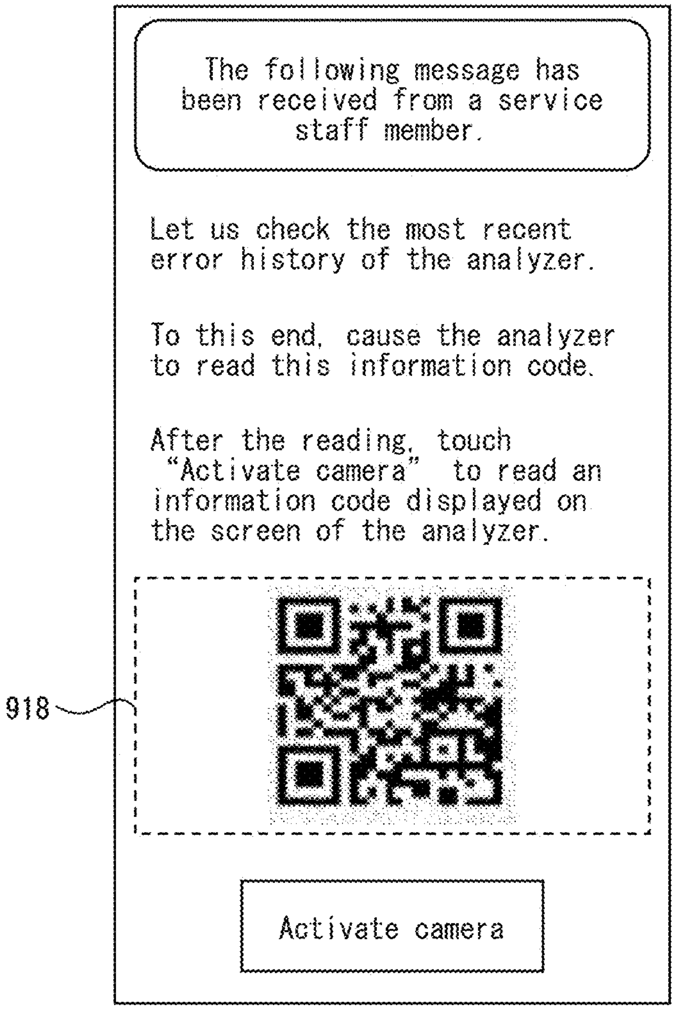
FIG. 49 shows another example of the screen displayed on the terminal, specifically, shows a screen displayed when instruction data including data for reading out error histories has been received.

FIG. 49 shows another example of the screen displayed through the display control process 1, specifically, shows a screen displayed when instruction data including an instruction ID "X882" (for reading out error histories) has been received. In a field 918, an information code for executing a process of extracting the most recent error history from the analyzer 2 is displayed. A specific example of data recorded in the information code is described as follows:

"Instruction,2023/04/11 17:59:22,XQ-320,F5659,X882".

In this specific example, the first code type "Instruction", the second code type "NULL value", the date-and-time information "17:59:22 on Apr. 11, 2023", the model name "XQ-320", the device ID "F5659", and an instruction ID "X882" (for reading out error histories) are recorded in a CSV format. When reading this information code, the analyzer 2 reads out the most recent error history stored in the analyzer 2, creates an information code on the basis of information about the error history having been read out, and displays the information code (see FIG. 60 described later in relation to an example of a screen). After causing the analyzer 2 to read the information code in FIG. 49, the user operates a button having the text "Activate camera" displayed in the screen of the terminal 3. When the camera is activated, the user can cause the terminal 3 to: photograph the information code based on the information about the error history; and transmit the information to the management device 4.

Figure 50:
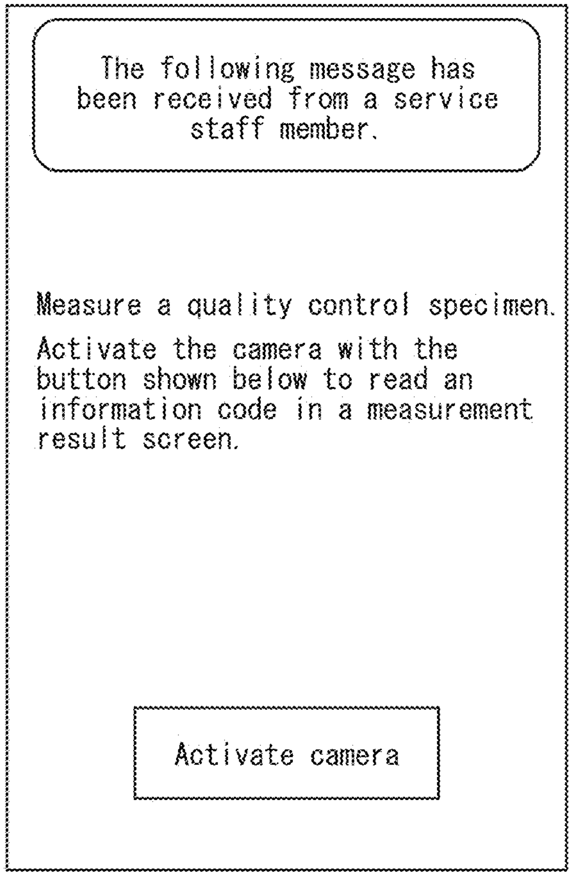
FIG. 50 shows another example of the screen displayed on the terminal, specifically, shows a screen displayed when instruction data including data for performing quality control measurement has been received.
Figure 51:
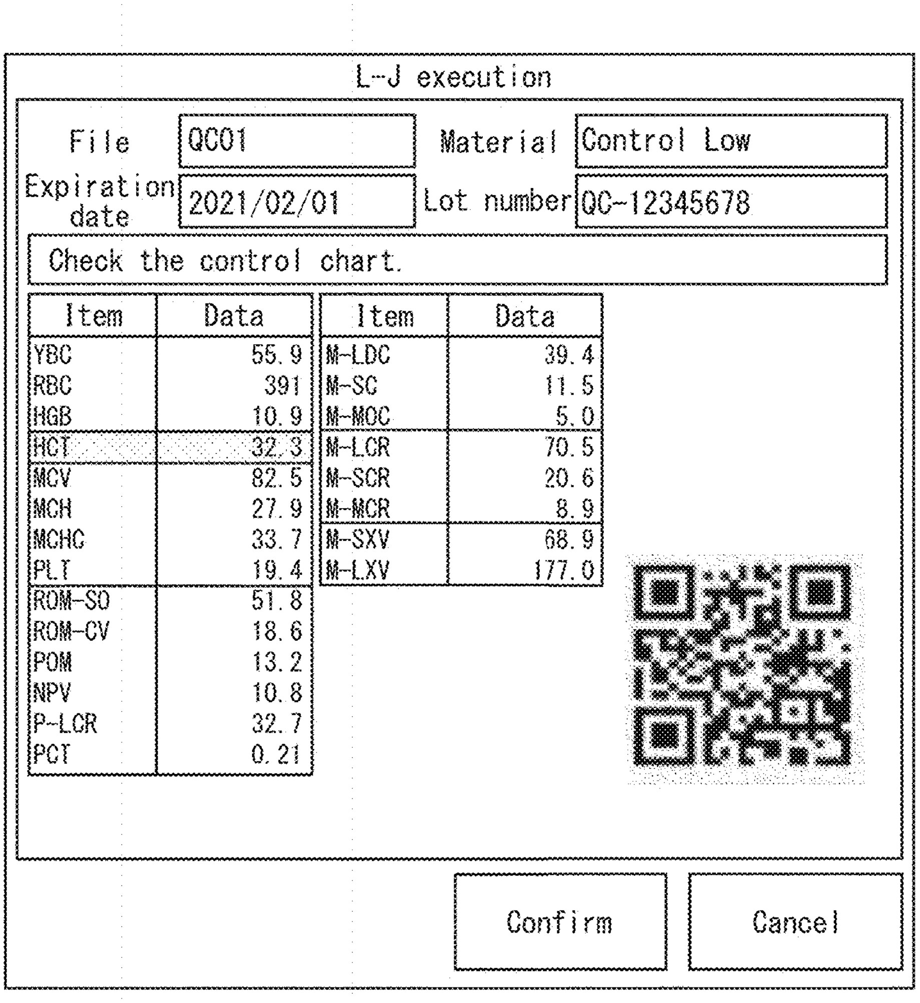
FIG. 51 shows an example of a screen, of an analyzer, in which an information code with a quality control result recorded therein is displayed.

FIG. 50 shows an example of a screen displayed through the display control process 2 when instruction data including an instruction ID "Q220" (for performing quality control measurement) has been received. In this example of the screen, an instruction to perform quality control measurement and an instruction to read an information code displayed on the analyzer 2 as a quality control result, are displayed as instructions directed to the health professional. The health professional operates the analyzer 2 according to these instructions. FIG. 51 shows an example of a screen, of the analyzer 2, in which an information code with a quality control result recorded therein is displayed after the analyzer 2 performs quality control measurement. The health professional causes the imaging device 32 of the terminal 3 to read the information code.

[Configuration Example of Analyzer 2]

Figure 52:
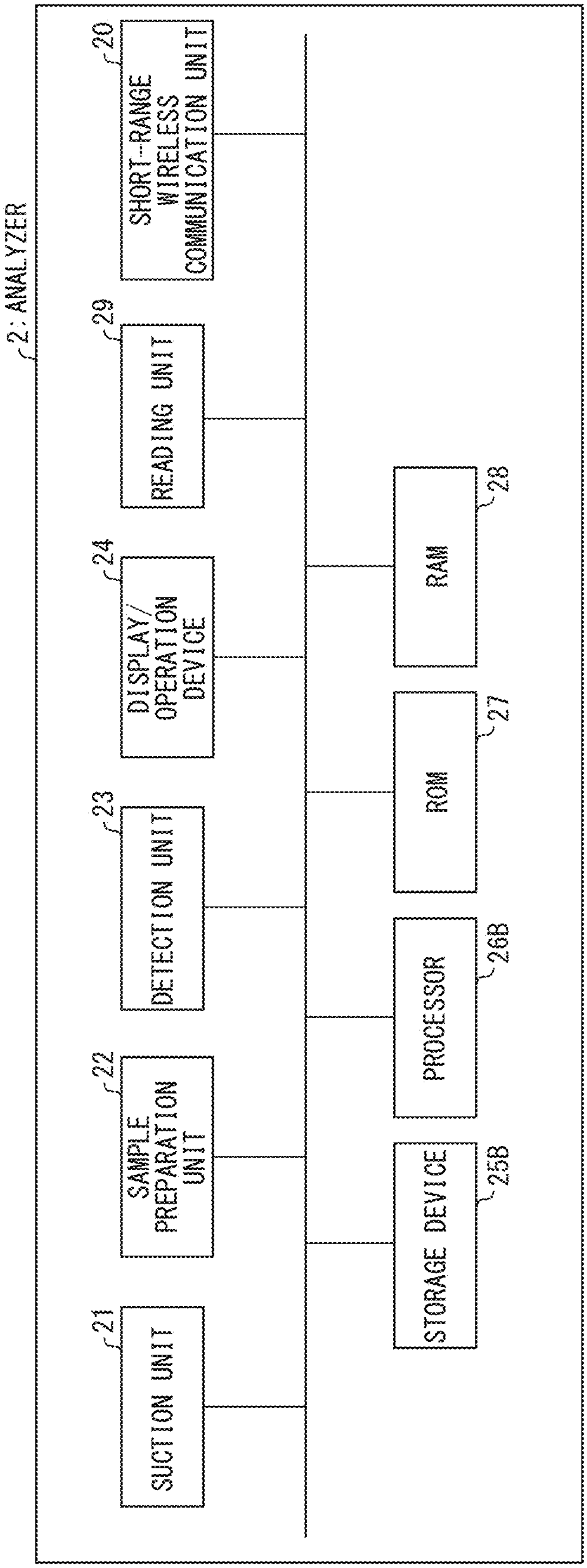
FIG. 52 shows a configuration example of the analyzer.

As shown in FIG. 52, the analyzer 2 according to the present embodiment has the same configuration as that of the analyzer 2 in embodiment 1, except that: a storage device 25B (storage unit) and a processor 26B are provided instead of the storage device 25A and the processor 26A; and a reading unit 29 is further provided or can be attached.

The reading unit 29 is a reader for optically reading the information code displayed on the output device 34 of the terminal 3. The reading unit 29 may be a reading unit usable with one hand in order to facilitate reading work to be performed by the health professional.

Figure 53:
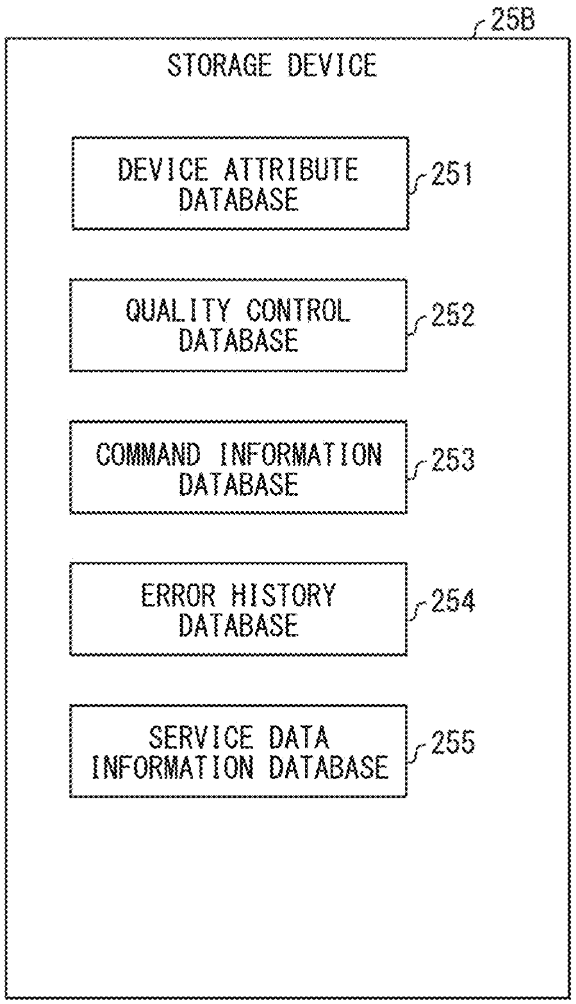
FIG. 53 shows a configuration example of a storage device of the analyzer.

The storage device 25B is for storing therein various data and various programs to be used by the analyzer 2 and is, for example, a semiconductor drive such as a solid-state drive or a magnetic disk such as a hard disk. As shown in FIG. 53, the storage device 25B stores therein, for example, a command information database 253, an error history database 254, and a service data information database 255 in addition to the device attribute database 251 and the quality control database 252.

Figure 54:
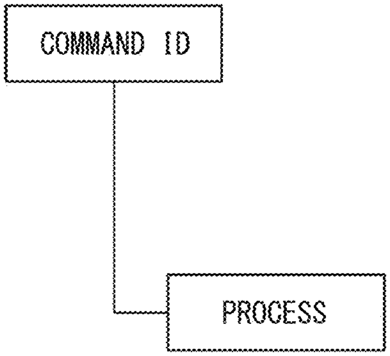
FIG. 54 shows an example of the data structure of a command information database.

The command information database 253 is a database for storing therein a command capable of being executed by the analyzer 2 and is, for example, an RDB. FIG. 54 shows an example of a data structure in a case where the command information database 253 is an RDB. As shown in the drawing, the command information database 253 stores therein, for example, the following pieces of information (D121) and (D122) such that these pieces of information are associated with each other.

(D121) Command ID: This is an identifier of the command. This identifier corresponds to the identifier of the command among the instruction IDs stored in the instruction information database 452 of the management device 4.

(D122) Process: This is one process or a set composed of a plurality of processes corresponding to the command ID.

Figures 55, 56:
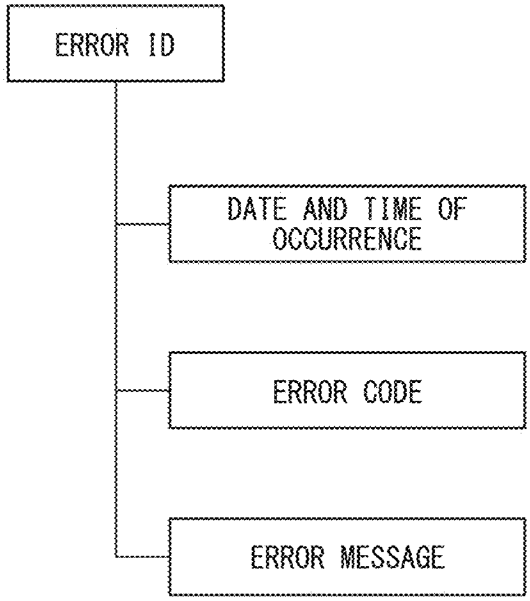
FIG. 55 shows a specific example of records in the command information database.
FIG. 56 shows an example of the data structure of an error history database.

FIG. 55 shows a specific example of records in the command information database 253.

The error history database 254 is a database for storing therein a history regarding an error having occurred in the analyzer 2 and is, for example, an RDB. The error is, for example, an abnormality, a warning, or the like regarding a pressure, a temperature, a reagent, a motor, specimen measurement, a cover, maintenance, a sampler measurement operation, or the like. Specific examples of the error are clogging in the RBC detector, abnormal decrease in pressure, and the like. FIG. 56 shows an example of a data structure in a case where the error history database 254 is an RDB. As shown in the drawing, the error history database 254 stores therein, for example, the following pieces of information (D31) to (D134) such that these pieces of information are associated with one another.

(D131) Error ID: This is an identifier designated to each error.

(D132) Date and time of occurrence: This is the date and the time of occurrence of the error.

(D133) Error code: This is an identifier indicating the type of the error. The error code is displayed on the display/operation device 24 when the error occurs, for example.

(D134) Error message: This is a message indicating a summary of the error. The error message is displayed on the display/operation device 24 when the error occurs, for example.

Figures 57, 58:
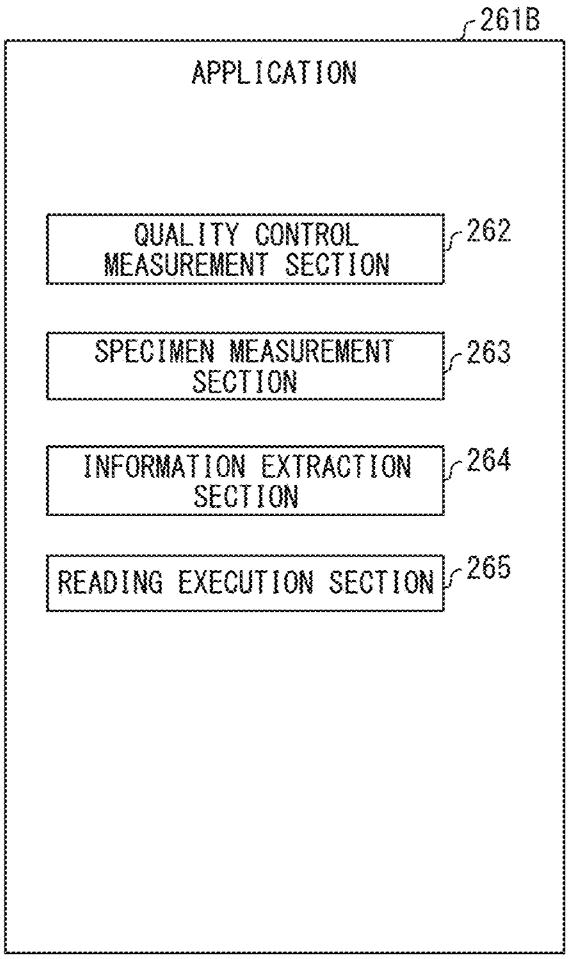
FIG. 57 shows a specific example of records in the error history database.
FIG. 58 shows a configuration example of an application that is operated in the analyzer.

FIG. 57 shows a specific example of records in the error history database 254. The drawing shows two records. The record on the upper side of the drawing is a history indicating that "clogging in the RBC detector" has occurred. The record on the lower side of the drawing is a history indicating that "abnormal decrease in pressure" has occurred.

The service data information database 255 is a database for storing therein various information collected in the analyzer 2 or various parameters set in the analyzer 2 (hereinafter, these pieces of data are referred to as "service data") and is, for example, an RDB. Examples of service data, regarding hardware, stored in the service data information database 255 are described as follows:

the numbers of times of operations performed by units (e.g., the total number of times of operations, the number of times of regular cleaning, and the numbers of times of operations performed by a piercer, a whole blood suction motor, an air pump, a pinch valve, and the like);

various pressure data (positive pressures and negative pressures);

environmental temperatures; and data of sensors used for monitoring respective parts (e.g., the blood suction sensor, a WBC/HGB detection sensor, an RBC detection sensor, and a mixing chamber detection sensor).

Examples of service data, regarding measurement of the number of blood cells, stored in the service data information database 255 are described as follows:

sampling data for monitoring noise (e.g., the number of particles in an RBC/PLT channel measured at fixed intervals)

reference data (e.g., the mode of red blood cell volumes, the mode of platelet volumes, the average large-sized red blood cell volume in an RBC bimodal particle size distribution, the average small-sized red blood cell volume in the RBC bimodal particle size distribution, the number of large-sized red blood cells in the RBC bimodal particle size distribution, and the number of small-sized red blood cells in the RBC bimodal particle size distribution);

the positions of discriminators in an RBC particle size distribution (e.g., the lower limit position of a red blood cell region in the RBC particle size distribution, the position of the bottom between the two modes of the RBC particle size distribution, and the upper limit position of the red blood cell region in the RBC particle size distribution);

the positions of discriminators in a PLT particle size distribution (e.g., the lower limit position of a red blood cell region in the PLT particle size distribution and the upper limit position of the red blood cell region in the RBC particle size distribution);

measurement values regarding hemoglobin (e.g., the optical concentration of a sample having been subjected to A/D conversion and the optical concentration of a blank sample having been subjected to A/D conversion);

particle size distribution abnormality flags; and values regarding RBC measurement (e.g., numerical values obtained by electrically detecting the extent of clogging in the RBC detector and the number of bubbles in the RBC detector).

With reference back to FIG. 52, the processor 26B is a controller that comprehensively controls the functions of the analyzer 2. The processor 26B is, for example, a CPU. The processor 26B may be implemented by, for example, a logic circuit. The processor 26B reads out an application 261B from the storage device 25B, loads the application 261B to the RAM 27, and executes the application 261B. The application 261B is stored in, for example, the storage device 25B as a program for causing a computer to function as a controller for executing various processes.

[Configuration Example of Application 261B]

FIG. 58 shows a configuration example of the application 261B. The application 261B includes, for example, a reading execution section 265 in addition to the quality control measurement section 262, the specimen measurement section 263, and the information extraction section 264.

The processor 26B executes the following "(Process P1)" on the basis of information read from the information code by the reading unit 29, according to an instruction from the reading execution section 265. Before the "(Process P1)" is executed, "(Process P2)" and/or "(Process P3)" may be executed.

(Process P1) The processor 26B determines, on the basis of the "first code type" and the "second code type" included in the read information, a type of the information recorded in the information code. In a case where the first code type is "Instruction", the processor 26B identifies, with reference to the command information database 253, a process corresponding to an instruction ID included in the read information and controls each unit of the analyzer 2 to execute the identified process.

In a case where the identified process is a process of reading out quality control histories, the processor 26B executes a quality control information extraction process according to an instruction from the information extraction section 264. In the quality control information extraction process, quality control results satisfying a predetermined extraction condition (e.g., quality control results obtained over the last one week) are obtained from the quality control database 252, an information code that allows reading of each of the obtained quality control results or a value (a statistical value or the like) calculated on the basis of these quality control results is created, and the display/operation device 24 is caused to display the created information code. An example of a screen displayed in this case is shown in FIG. 59. The quality control results satisfying the predetermined extraction condition are one kind of management information to be obtained by the management device 4.

In a case where the identified process is a process of reading out error histories, the processor 26B executes an error history extraction process according to an instruction from the information extraction section 264. In the error history extraction process, error histories satisfying a predetermined extraction condition (e.g., error histories obtained over the last one week, error histories that are allowed, through user setting or the like, to be outputted, or the like) are obtained from the error history database 254, an information code that allows reading of each of the obtained error histories is created, and the display/operation device 24 is caused to display the created information code. An example of a screen displayed in this case is shown in FIG. 60. The error histories satisfying the predetermined extraction condition are one kind of management information to be obtained by the management device 4.

Figure 61:
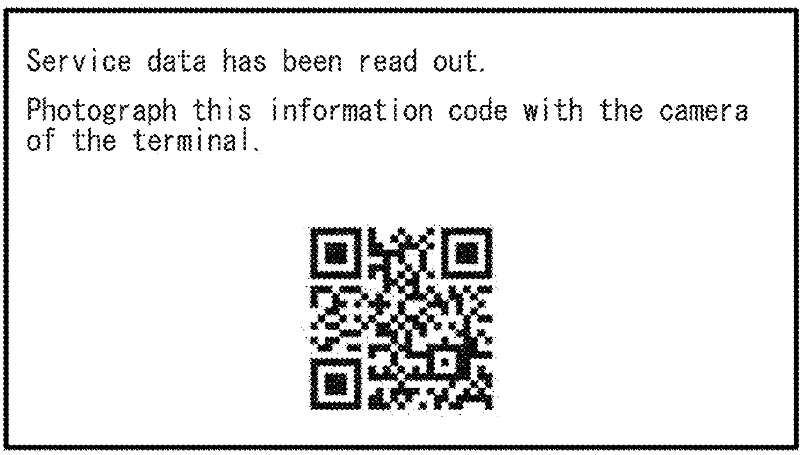
FIG. 61 shows an example of a screen, of the analyzer, in which an information code regarding service data is displayed.

In a case where the identified process is a process of reading out service data, the processor 26B executes a service data extraction process according to an instruction from the information extraction section 264. In the service data extraction process, pieces of service data satisfying a predetermined extraction condition (e.g., predetermined service data, service data that is allowed, through user setting or the like, to be outputted, or the like) are obtained from the service data information database 255, an information code that allows reading of each of the obtained pieces of service data is created, and the display/operation device 24 is caused to display the created information code. An example of a screen displayed in this case is shown in FIG. 61. The pieces of service data satisfying the predetermined extraction condition are one kind of management information to be obtained by the management device 4.

(Process P2) The processor 26B may determine whether or not the device ID included in the read information and the device ID stored in the device attribute database 251 match. When the device IDs match, the processor 26B may execute the reading process. Meanwhile, when the device IDs do not match, the processor 26B may stop the reading process. Consequently, in a case where, for example, a plurality of the analyzers 2 are installed in the medical facility, it is possible to avoid a situation in which an information code to be read by an intended one of the analyzers is erroneously read by another one of the analyzers so that a process that should not to be executed is executed by the other analyzer. That is, it is possible to prevent failure to select the appropriate analyzer 2 that is to execute the process. Consequently, for example, troubleshooting and the like can be assuredly performed. In the case of stopping the reading process, the processor 26B may cause the display/operation device 24 to display a message indicating that the device IDs do not match.

(Process P3) The processor 26B may determine whether or not the information code is valid, on the basis of the date-and-time information (the date and the time of issuance and/or the expiration of validity period) included in the read information. In one example, the processor 26B may determine that the information code is not valid, in a case where the difference between the present time and the date and the time of issuance included in the read information is equal to or larger than a predetermined time period (e.g., 30 minutes). In another example, the processor 26B may determine that the information code is not valid, in a case where the validity period included in the read information has expired. When determining that the information code is valid, the processor 26B may execute the reading process. Meanwhile, when determining that the information code is not valid, the processor 26B may stop the reading process. Consequently, an information code having been previously used can be prevented from being used in a shared manner. Therefore, for example, information that can be obtained only in the service mode can be prevented from being obtained by a user for the purpose of unauthorized use thereof, and a process that can be executed only in the service mode can be prevented from being executed by the analyzer 2 without any permission of the service staff member. In the case of stopping the reading process, the processor 26B may cause the display/operation device 24 to display a message indicating that the information code is not valid.

[Example of Flow of Processing]

Figure 62:
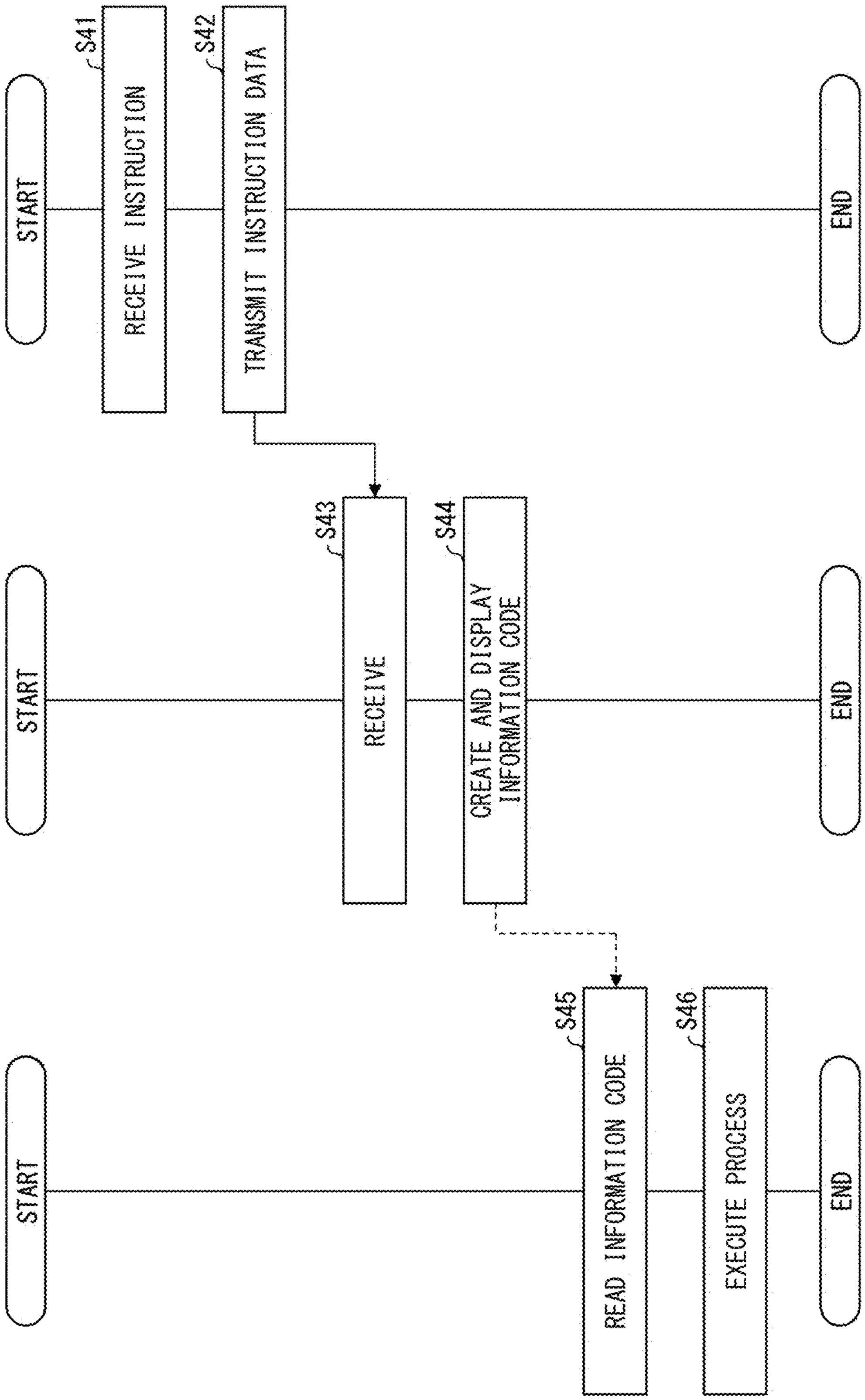
FIG. 62 is a flowchart showing an example of the flow of processing according to which processes are executed from the management device via the terminal by the analyzer.

FIG. 62 is a flowchart showing an example of the flow of processing according to which processes are executed from the management device 4 via the terminal 3 by the analyzer 2. The processor 46A of the management device 4 receives an instruction in, for example, the instruction information creation screen 4631 (S41) and transmits the instruction data to the terminal 3 (S42). The processor 36A of the terminal 3 receives the instruction data (S43), creates an information code that, for example, allows reading of the instruction data, and causes the output device 34 to display the information code (S44, displaying step). In other words, in step S44, the processor 36A presents, to the output device 34, information about a process to be executed by the analyzer 2 (presenting step). The processor 26A of the analyzer 2 causes the information code to be read (S45, reading step) and executes a process based on the instruction included in the read information (S46, execution step). In this manner, the health professional can cause the analyzer 2 to execute the process based on the instruction from the service staff member, just by performing a simple operation of causing the analyzer 2 to read the information code displayed on the terminal 3. In addition, the service staff member allows the analyzer 2 to execute the process without performing communication with the health professional by telephone or the like and without visiting the medical facility. Consequently, the service staff member can efficiently and swiftly perform maintenance/running and the like.

Figure 63:
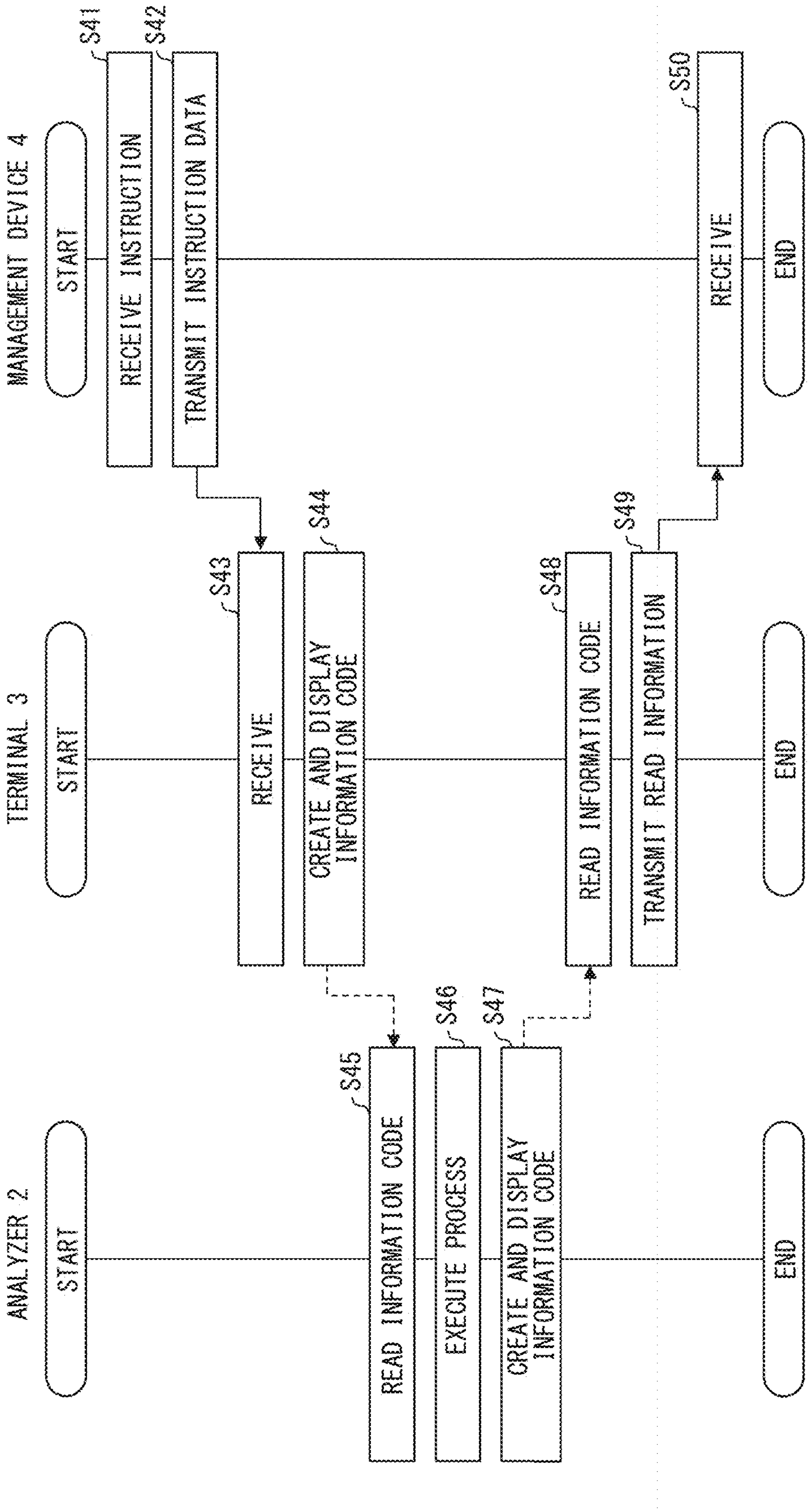
FIG. 63 is a flowchart showing a modification of the flowchart shown in FIG. 62.

FIG. 63 shows a modification of the flowchart shown in FIG. 62. In the present modification, steps S47 to S50 are added. After executing the process in step S46, the processor 26A of the analyzer 2 causes the display/operation device 24 to display an information code that allows reading of quality control results, for example (S47, preparation step). The processor 36A of the terminal 3 causes the imaging device 32 to read the information code (S48) and transmits the read information to the management device 4 (S49). The processor 46A of the management device 4 receives the information (S50). Thus, the service staff member can receive, for example, the quality control results in step S50 as a result of giving the instruction in step S41. Consequently, the service staff member can flexibly perform maintenance/running by, for example, further giving another instruction while checking the post-instruction state of the analyzer 2. In a case where the amount of data to be transmitted from the analyzer 2 to the terminal 3 is large, it is also possible to, instead of reading the information code in steps S47 and S48, transmit the information from the analyzer 2 to the terminal 3 through short-range wireless communication such as Bluetooth as described in embodiment 1.

Embodiment 3

The same constituents and steps as those described in the above embodiments are denoted by the same reference characters, and descriptions thereof are omitted.

The present embodiment will be described as an embodiment in which information about an error (hereinafter, referred to as "error information") having occurred in an analyzer 2 is transmitted via the terminal 3 to the management device 4. As described in embodiment 2, the error is, for example, an abnormality, a warning, or the like regarding a pressure, a temperature, a reagent, a motor, specimen measurement, a cover, maintenance, a sampler measurement operation, or the like. Specific examples of the error are clogging in the RBC detector, abnormal decrease in pressure, and the like. According to the present embodiment, the error information stored in the analyzer 2 being operated in an environment that does not allow communication with any devices outside the medical facility can be transmitted to the management device 4. Moreover, this transmission can be performed without any erroneous operation through only a simple operation of reading an information code, whereby even a health professional who is not proficient in handling of the analyzer 2 can easily perform the transmission. In addition, even though the health professional does not inform the service staff member of the error information about the analyzer 2 by telephone or the like, the service staff member can accurately ascertain the error information and can assuredly perform troubleshooting and the like.

[Configuration Example of Analyzer 2]

Figure 64:
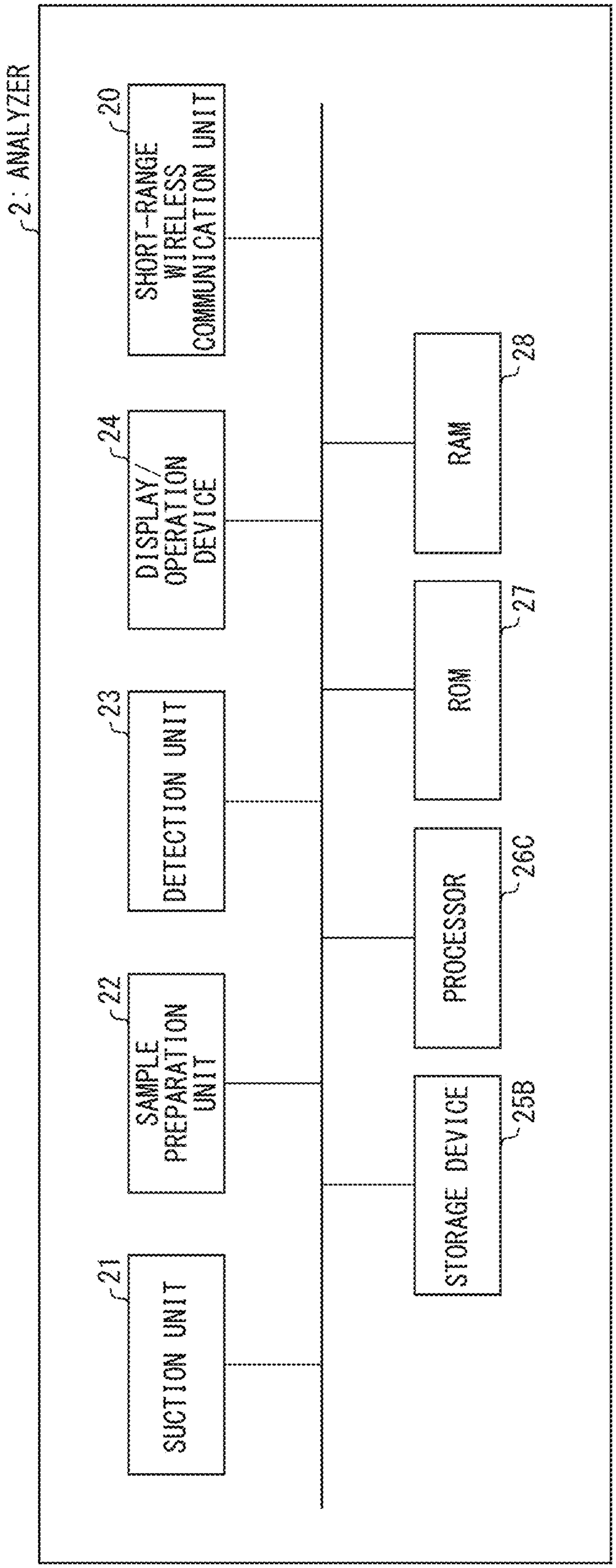
FIG. 64 shows a configuration example of an analyzer.

As shown in FIG. 64, the analyzer 2 according to the present embodiment has the same configuration as that of the analyzer 2 in embodiment 2, except that a processor 26C is provided instead of the processor 26B.

The processor 26C is a controller that comprehensively controls the functions of the analyzer 2. The processor 26C is, for example, a CPU. The processor 26C may be implemented by, for example, a logic circuit. The processor 26C reads out an application 261C from the storage device 25B, loads the application 261C to the RAM 27, and executes the application 261C. The application 261C is stored in, for example, the storage device 25B as a program for causing a computer to function as a controller for executing various processes.

[Configuration Example of Application 261C]

Figure 65:
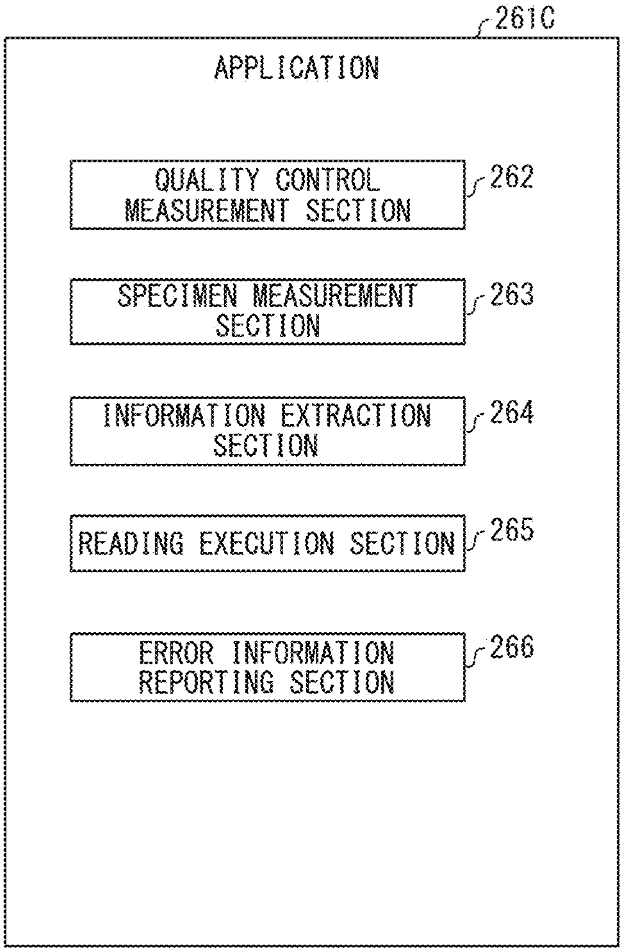
FIG. 65 shows a configuration example of an application that is operated in the analyzer.

FIG. 65 shows a configuration example of the application 261C. The application 261C includes, for example, an error information reporting section 266 in addition to the quality control measurement section 262, the specimen measurement section 263, the information extraction section 264, and the reading execution section 265.

The processor 26C executes an error information extraction process according to an instruction from the error information reporting section 266. A typical example of the trigger for execution of the error information extraction process is occurrence of an error, but the trigger may be reception, of a predetermined input operation, by the display/operation device 24.

In a typical example of the error information extraction process, an error history satisfying a predetermined extraction condition (e.g., one or more errors having occurred most recently) is obtained from the error history database 254, an information code that allows reading of the obtained error history is created, and the display/operation device 24 is caused to display the created information code. Information recorded in the information code created through the error information extraction process is, for example, as indicated by the following pieces of information (D141) to (D146). Data obtained by setting the format of these pieces of information to a CSV format is recorded in the information code.

(D141) First code type: An example thereof is "Error".

(D142) Second code type: This is unused. An example thereof is a NULL value.

(D143) Date-and-time information: This is the date and the time of creation of the information code.

(D144) Model name: This is the model name of the analyzer 2 having created the information code. The model name is obtained from the device attribute database 251.

(D145) Device ID: This is the identifier of the analyzer 2 having created the information code. The device ID is obtained from the device attribute database 251.

(D146) Data body: This is information about the error. Specifically, the information includes the date and the time of occurrence of the error, an error code, and an error message. The data body is obtained from the error history database 254.

[Example of Screen]

Figure 66:
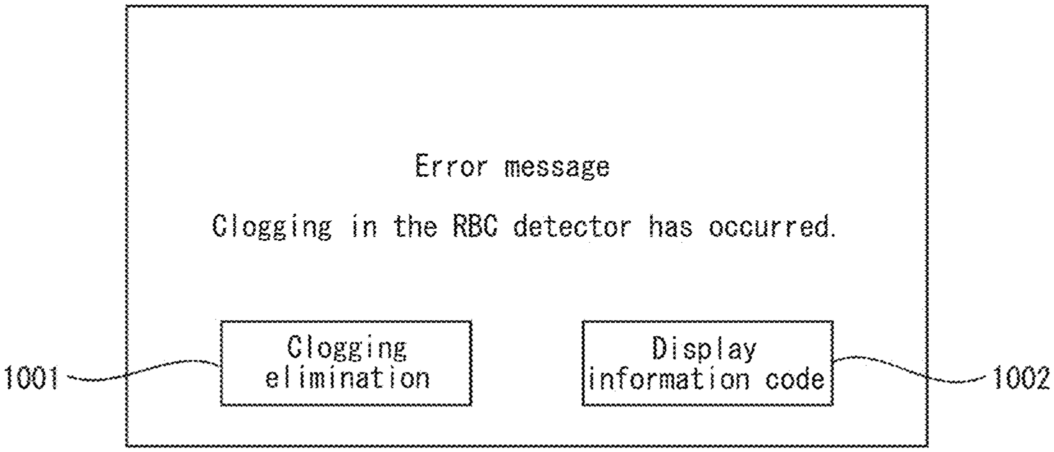
FIG. 66 shows an example of a screen displayed on the analyzer when clogging in an RBC detector has occurred.

FIG. 66 shows an example of a screen that the error information reporting section 266 causes the display/operation device 24 to display when "clogging in the RBC detector" has occurred.

When an operation is received through a button 1001, the processor 26C controls each unit of the analyzer 2 to execute a preset operation for unclogging the RBC detector. Consequently, when, for example, clogging in the RBC detector occurs for the first time in the present day, the health professional can attempt to solve the error by himself/herself first without receiving assistance from the service staff member, for example.

Figure 67:
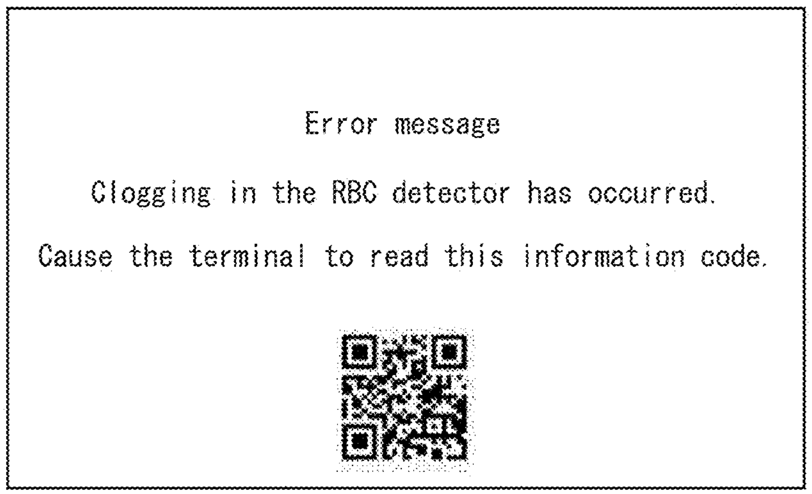
FIG. 67 shows an example of a screen, of the analyzer, in which an information code regarding clogging in the RBC detector is displayed.

When an operation is received through a button 1002, the processor 26C executes the error information extraction process according to an instruction from the error information reporting section 266 and causes the display/operation device 24 to display a created information code. FIG. 67 shows an example of a screen in which this created information code is displayed. Consequently, in cases where it is necessary to receive assistance from the service staff member such as a case where the health professional cannot solve clogging in the RBC detector by himself/herself, the service staff member can be notified of the error information via the terminal 3.

A specific example of data recorded in the information code is described as follows:

"Error,2023/04/11 17:59:22,XQ-320,F5659,2023/03/30 16:28:00,311240".

In this specific example, a first code type "Error", the second code type "NULL value", the date-and-time information "17:59:22 on Apr. 11, 2023", the model name "XQ-320", the device ID "F5659", the date and the time of occurrence of the error "16:28:00 on Mar. 30, 2023", and an error code "311240" (clogging in the RBC detector) are recorded in a CSV format.

Figure 68:
FIG. 68 shows an example of a screen displayed on the terminal when a reception notification has been received from the management device.

After the terminal 3 reads the information code and transmits the read information to the management device 4, the terminal 3 desirably receives, in response to the transmission, a reception notification from the management device 4. Consequently, the health professional can be made aware that the service staff member has been notified of the error information. FIG. 68 shows an example of a screen in which such a reception notification is displayed on the terminal 3.

Figure 69:
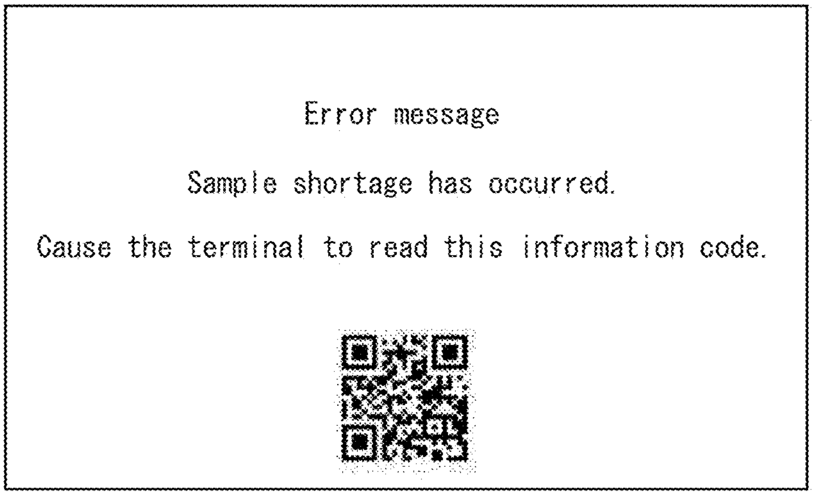
FIG. 69 shows an example of a screen, of the analyzer, in which an information code regarding sample shortage is displayed.

FIG. 69 shows an example of a screen in which an information code created at the time of occurrence of "sample shortage (insufficiency in the amount of blood)" is displayed. A specific example of data recorded in the information code is described as follows:

"Error,2023/04/11 17:59:22,XQ-320,F5659,2023/03/30 16:28:00,228239".

In this specific example, the first code type "Error", the second code type "NULL value", the date-and-time information "17:59:22 on Apr. 11, 2023", the model name "XQ-320", the device ID "F5659", the date and the time of occurrence of the error "16:28:00 on Mar. 30, 2023", and an error code "228239" (sample shortage) are recorded in a CSV format.

[Flow of Processing]

Figure 70:
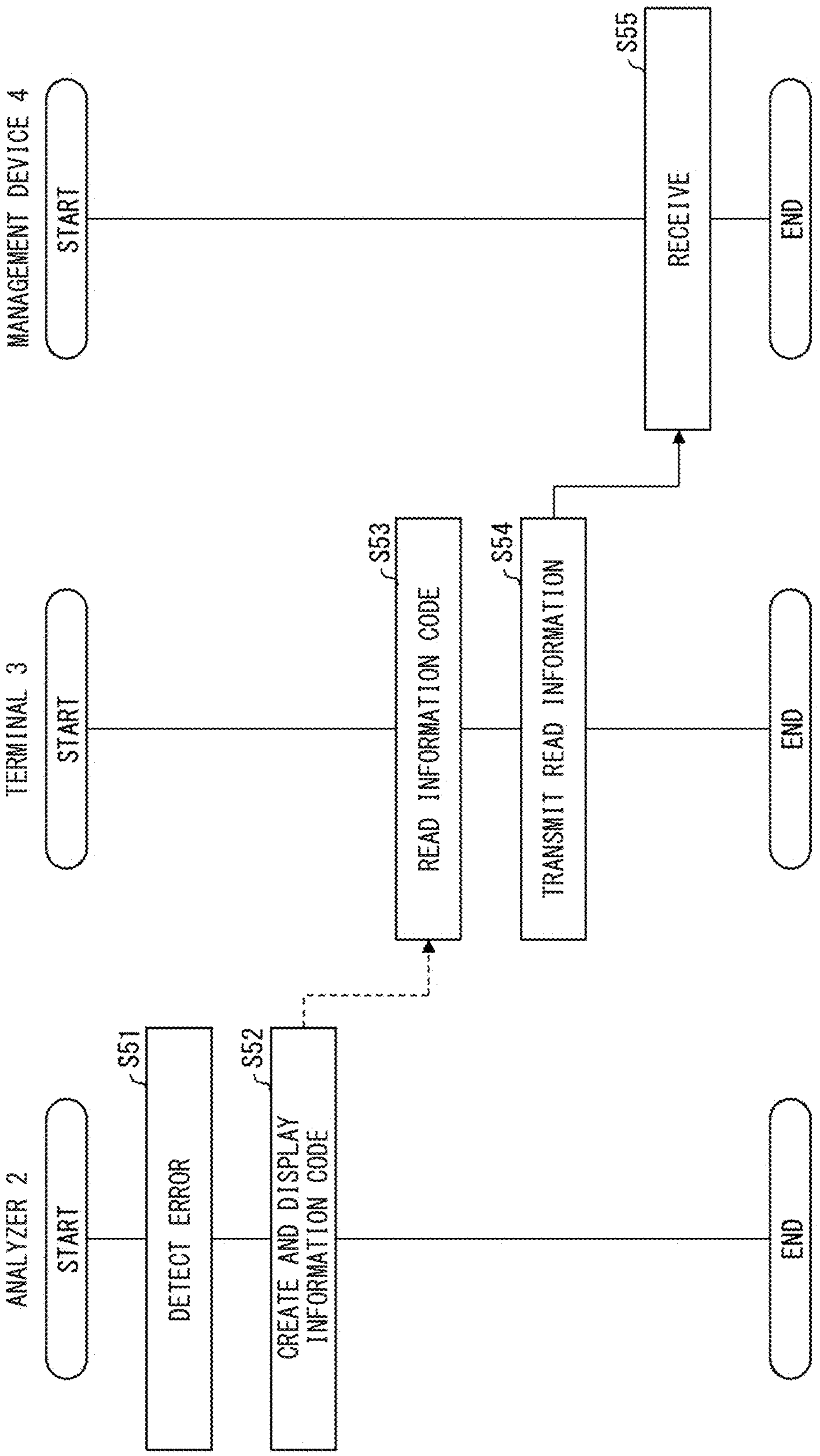
FIG. 70 is a flowchart showing an example of the flow of processing according to which information about an error having occurred in the analyzer is transmitted via the terminal to the management device.

FIG. 70 is a flowchart showing an example of the flow of processing according to which information about an error having occurred in the analyzer 2 is transmitted via the terminal 3 to the management device 4. When an error is detected (S51), the processor 26C of the analyzer 2 executes the error information extraction process and causes the display/operation device 24 to display an information code that allows reading of the error information (S52, preparation step). The terminal 3 causes the imaging device 32 to read the information code (S53) and transmits the read information to the management device 4 (S54). The management device 4 receives the information (S55), and the service staff member takes action on the basis of the information.

Figure 71:
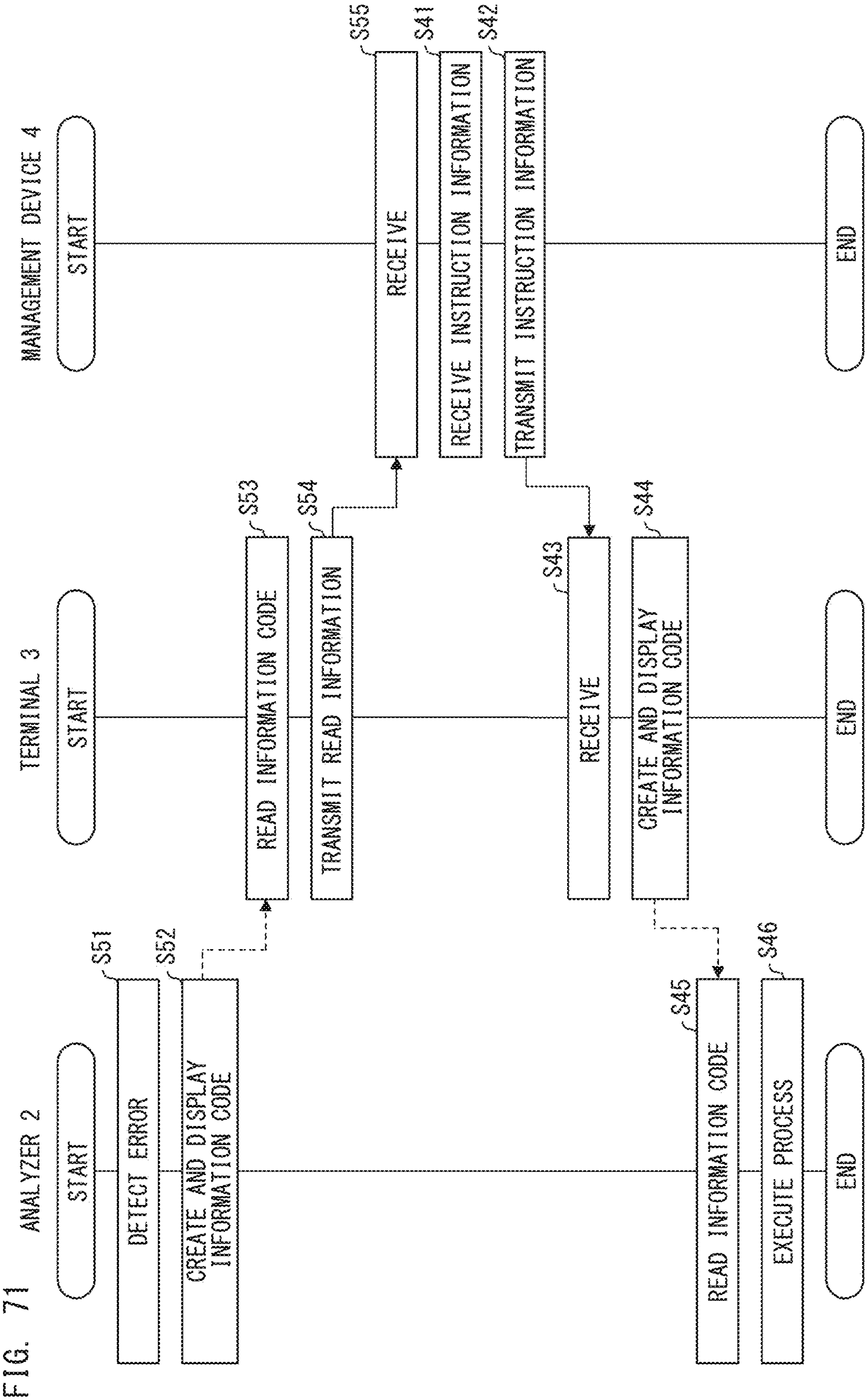
FIG. 71 is a flowchart showing an example obtained by extending the flowchart shown in FIG. 70.

FIG. 71 shows an example obtained by extending the flowchart shown in FIG. 70. In this example, steps S41 to S46 shown in FIG. 62 described in embodiment 2 are performed after step S55. In an example of the action taken by the service staff member, the management device 4 receives an instruction for dealing with the error on, for example, the instruction information creation screen 4631 shown in FIG. 43 (S41), and transmits instruction data to the terminal 3 (S42).

As an example of the action, an action taken when error information about clogging in the RBC detector is received in step S55 is described as follows. That is, in step S41, input of instructions according to which the analyzer 2 executes "clogging elimination" and "consecutive blank check" is received by using the instruction information creation screen 4631. In this case, the text "Clogging in RBC detector" is desirably displayed as the status of the analyzer 2 in the field 902 of the instruction information creation screen 4631, as shown in FIG. 43.

As another example of the action, an action taken when error information about sample shortage is received in step S55 is described as follows. That is, in step S41, input of an instruction according to which the analyzer 2 "turns off the blood suction sensor" is received by using the instruction information creation screen 4631. In this case, the text "Sample shortage" is desirably displayed as the status of the analyzer 2 in the field 902 of the instruction information creation screen 4631.

The terminal 3 receives the instruction data (S43) and causes the output device 34 to display an information code that allows reading of the instruction data (S44). The processor 26C of the analyzer 2 causes the information code to be read (S45) and executes a process based on the read information (S46). Through the above flow, the service staff member having received the error information allows the analyzer 2 to execute a command for dealing with the error.

[Modification 1]

In step S41 shown in FIG. 71, the management device 4 may, instead of receiving an instruction for dealing with the error from the service staff member, automatically determine the instruction. Specifically, the management device 4 may store, in the storage device 25B, a database in which pieces of error information and instructions are associated with each other and may automatically determine, with reference to the database, an instruction corresponding to the information received in step S55.

[Modification 2]

In the case of performing automation described in the above modification 1, the constituent that performs the operation of determining an instruction may be the terminal 3. Specifically, the terminal 3 may store, in the storage device 35A of the terminal 3, a database in which pieces of error information and instructions are associated with each other, and may determine, with reference to the database, an instruction corresponding to the information read in step S53.

Embodiment 4

The same constituents and steps as those described in the above embodiments are denoted by the same reference characters, and descriptions thereof are omitted.

The present embodiment is an embodiment in which information stored in the analyzer 2 is extracted and transmitted via the terminal 3 to the management device 4. The trigger for execution of a process of extracting the information stored in the analyzer 2 may be reception, of an input operation, by the display/operation device 24 of the analyzer 2, for example. Consequently, the health professional can cause the analyzer 2 to execute an information extraction process spontaneously or upon reception of a request from the service staff member by telephone or the like.

Figure 72:
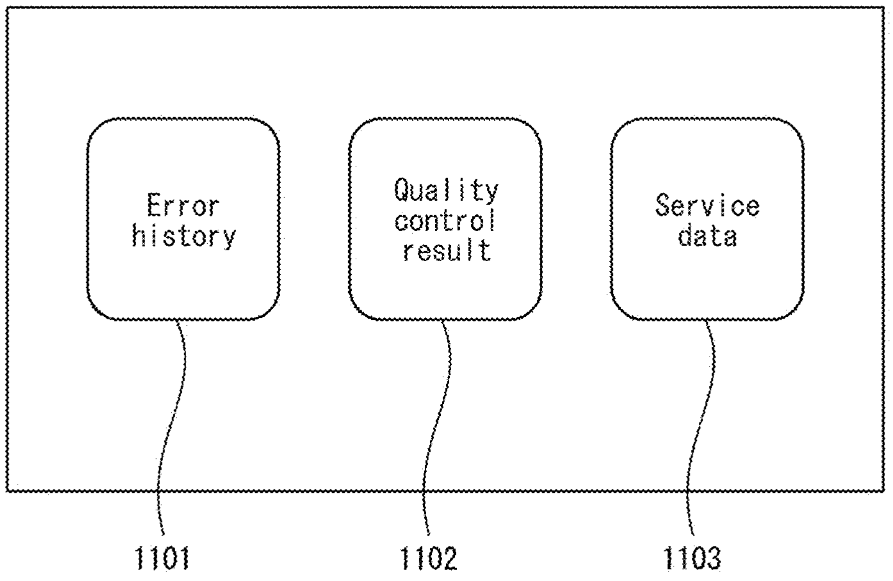
FIG. 72 shows an example of a screen for selecting information to be extracted from the analyzer.

For example, when the display/operation device 24 receives a predetermined input operation, the processor 26B executes the information extraction process according to an instruction from the information extraction section 264 and causes the display/operation device 24 to display a created information code. FIG. 72 shows an example of a screen for selecting information to be extracted. This screen may be capable of being displayed as a result of transition from the menu screen. In the example shown in the drawing, buttons 1101 to 1103 are provided as menu items for selecting any of quality control history, error history, and service data.

When an operation is received through the button 1101, the processor 26B obtains, from the quality control database 252, quality control results satisfying a predetermined extraction condition. Then, the processor 26B creates an information code that allows reading of each of the obtained quality control results or a value (a statistical value or the like) calculated on the basis of these quality control results. Then, the processor 26B causes the display/operation device 24 to display the created information code. A screen displayed in this case is, for example, the same as that in FIG. 59.

When an operation is received through the button 1102, the processor 26B obtains, from the error history database 254, error histories satisfying a predetermined extraction condition. Then, the processor 26B creates an information code that allows reading of each of the obtained error histories. Then, the processor 26B causes the display/operation device 24 to display the created information code. A screen displayed in this case is, for example, the same as that in FIG. 60.

When an operation is received through the button 1103, the processor 26B obtains, from the service data information database 255, pieces of service data satisfying a predetermined extraction condition. Then, the processor 26B creates an information code that allows reading of each of the obtained pieces of service data. Then, the processor 26B causes the display/operation device 24 to display the created information code. A screen displayed in this case is, for example, the same as that in FIG. 61.

Figure 73:
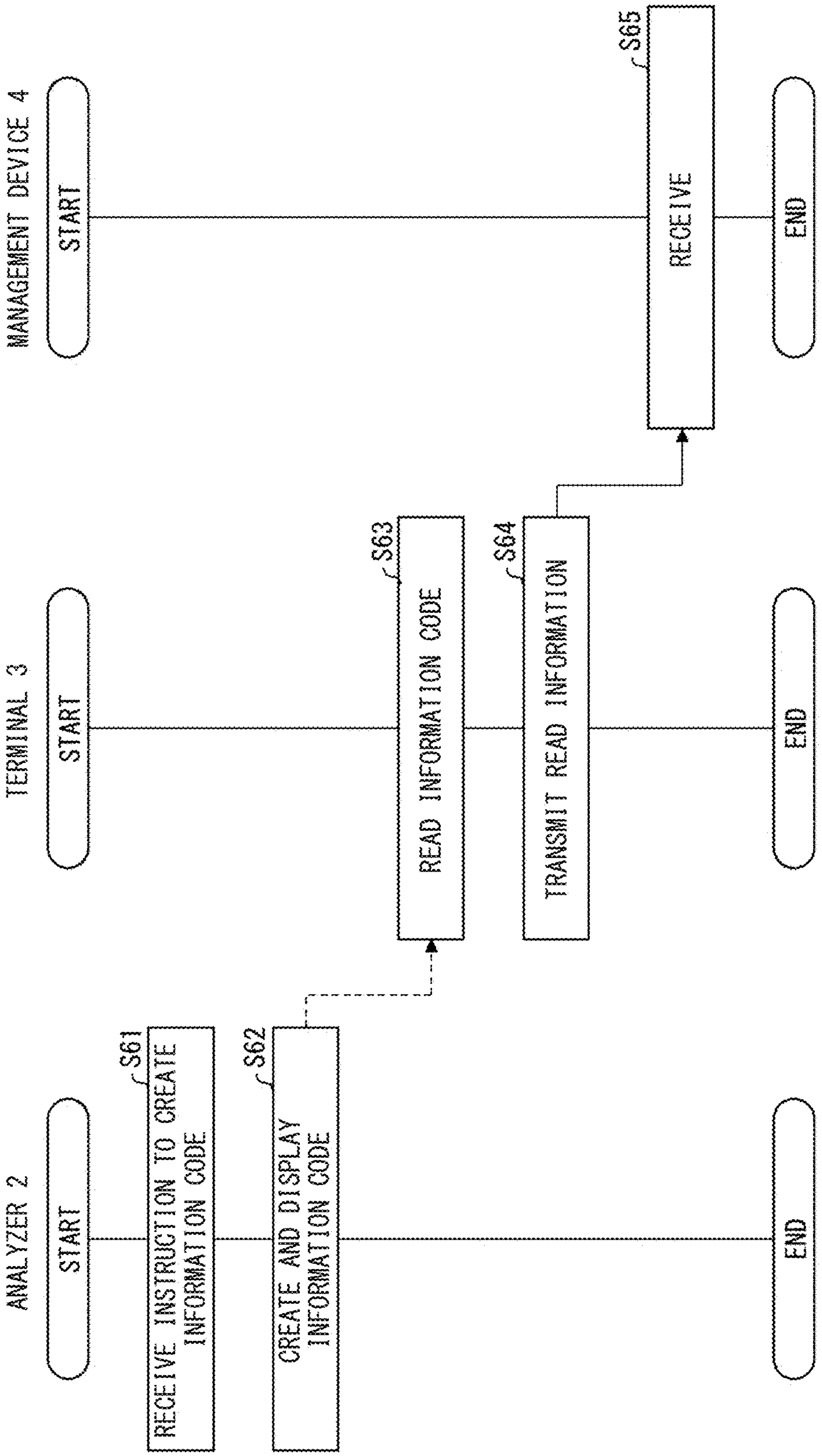
FIG. 73 is a flowchart showing an example of the flow of an information extraction process.

FIG. 73 is a flowchart showing an example of the flow of the information extraction process. When an input operation for creating an information code is received (S61), the processor 26B of the analyzer 2 causes the display/operation device 24 to display an information code that allows reading of information based on the input operation (S62, preparation step). The terminal 3 causes the imaging device 32 to read the information code (S63) and transmits the read information to the management device 4 (S64). The management device 4 receives the information (S65), and the service staff member performs maintenance/running and the like on the basis of the information. In a case where the amount of data to be transmitted from the analyzer 2 to the terminal 3 is large, it is also possible to, instead of reading the information code in steps S62 and S63, transmit the information from the analyzer 2 to the terminal 3 through short-range wireless communication such as Bluetooth as described in embodiment 1.

The present disclosure is not limited to the embodiments described above, and various modifications can be made within the scope of the claims. Embodiments obtained by combining, as appropriate, technological means disclosed in different embodiments are also included in the technological scope of the present disclosure.

Remarks

The present disclosure includes following items 1-15.

Item 1: A maintenance method for an analyzer that is not communicably connected to a network outside of a facility, the maintenance method comprising:

presenting, by a terminal that is communicably connected to the network outside of the facility, information about a process to be executed by the analyzer;

reading, by the analyzer, the information having been presented by the terminal; and executing, by the analyzer, the process indicated by the information having been read.

Item 2: The maintenance method of item 1, wherein the presenting includes displaying an optically readable information code including the information.

Item 3: The maintenance method of item 1, wherein the information includes a set composed of a plurality of the processes.

Item 4: The maintenance method of item 1, wherein the information includes order information indicating an order of execution of a plurality of the processes, and the executing includes executing, by the analyzer, the plurality of the processes according to the order of execution indicated by the order information having been read.

Item 5: The maintenance method of item 1, wherein the process includes a process that cannot be executed in a user mode of the analyzer and that can be executed in a service mode.

Item 6: The maintenance method of item 1, wherein the information includes an ID for identifying a command corresponding to the process, and the executing includes executing, by the analyzer, the process corresponding to the ID having been read.

Item 7: The maintenance method of item 1, wherein the information includes an ID of the analyzer, and the executing includes determining, by the analyzer, whether or not the ID having been read and an ID stored in the analyzer match, and executing, by the analyzer, the process when the IDs match.

Item 8: The maintenance method of item 2, wherein the information code includes date-and-time information indicating a date and a time of issuance and/or an expiration of validity period of the information code, and the executing includes determining, by the analyzer, whether or not the information code is valid, on the basis of the date-and-time information having been read from the information code, and executing, by the analyzer, the process when the information code is valid.

Item 9: The maintenance method of item 8, wherein the executing includes displaying, when the information code is not valid, a message by the analyzer without executing the process by the analyzer, the message indicating that the information code is not valid.

Item 10: The maintenance method of item 1, further comprising:

displaying, by the analyzer, an information code that allows reading of information stored in the analyzer;

reading said information code by the terminal;

transmitting the information from the terminal to a management device that is not communicably connected to the analyzer and that is communicably connected to the terminal, the information having been read from said information code; and receiving, by the management device, input of one or more of the processes corresponding to the information having been transmitted.

Item 11: The maintenance method of item 10, further comprising transmitting information from the management device to the terminal, the information indicating the processes the input of which has been received, wherein the presenting includes displaying, by the terminal, the information code that allows reading of the information indicating the processes the input of which has been received.

Item 12: The maintenance method of item 10, wherein the executing includes displaying, by the analyzer, the information code that allows reading of quality control-related information obtained by the analyzer after the process is executed by the analyzer, the maintenance method further comprising:

reading said information code by the terminal; and transmitting, to the management device, the information having been read from said information code.

Item 13: The maintenance method of item 1, wherein the analyzer is not connected to the Internet.

Item 14: The maintenance method of item 1, wherein the terminal is connected via a mobile communication network to the Internet.

Item 15: The maintenance method of item 1, wherein the terminal is a smartphone or a tablet terminal.

Item 16: A system comprising:

an analyzer that is not communicably connected to a network outside of a facility, and a terminal that is communicably connected to the network outside of the facility, wherein the terminal is configured to present information about a process to be executed by the analyzer;

the analyzer is configured to read the information presented by the terminal and execute the process indicated by the information read by the analyzer.

Item 17: The system of item 16, wherein the terminal is communicably connected to a management device via the network, the terminal is configured to obtain the information about the process to be executed by the analyzer.

Item 18: The system of item 17, wherein the analyzer is configured to display an information code that allows reading of information stored in the analyzer, and the terminal is configured to transmit, in response to reading the information code, the information from the terminal to the management device.

Item 19: The system of item 18, wherein the terminal is configured to receive from the management device the information indicating the processes, and to present the information code corresponding to the information received.

Item 20: The system of item 16, wherein the terminal is connected via a mobile communication network to the Internet.

What is claimed is:

1. A maintenance method for performing a troubleshooting of an analyzer that is not communicably connected to a network outside of a facility, wherein the analyzer comprises:

a suction unit configured to suction a specimen from a specimen container;

a sample preparation unit configured to prepare a measurement sample from the suctioned specimen;

a detector configured to measure components in the measurement sample;

a display configured to display a measurement result obtained by measurement by the detector; and a reader configured to optically read an information code;

the maintenance method comprising:

presenting, by a terminal that is communicably connected to the network outside of the facility, the information code encoding information about a process to be executed for troubleshooting of the analyzer;

reading, by the reader of the analyzer, the information code presented by the terminal, thereby causing the analyzer to determine a troubleshooting operation; and executing, by the analyzer, the determined troubleshooting operation.

2. The maintenance method of claim 1, wherein the presenting includes displaying an optically readable information code including the information.

3. The maintenance method of claim 1, wherein the information includes a set of a plurality of the processes.

4. The maintenance method of claim 1, wherein the information includes order information indicating an order of execution of a plurality of the processes, and the executing includes executing, by the analyzer, the plurality of the processes according to the order of execution indicated by the order information read by the analyzer.

5. The maintenance method of claim 1, wherein the process includes a process that cannot be executed in a user mode of the analyzer and that can be executed in a service mode.

6. The maintenance method of claim 1, wherein the information includes an ID for identifying a command corresponding to the process, and the executing includes executing, by the analyzer, the process corresponding to the ID included in the information read by the analyzer.

7. The maintenance method of claim 1, wherein the information includes an ID of the analyzer, and the executing includes determining, by the analyzer, whether or not the ID included in the information read by the analyzer and an ID stored in the analyzer match, and executing, by the analyzer, the process when the IDs match.

8. The maintenance method of claim 2, wherein the information code includes date-and-time information indicating a date and a time of issuance and/or an expiration of validity period of the information code, and the executing includes determining, by the analyzer, whether or not the information code is valid, on the basis of the date-and-time information included in the information code, and executing, by the analyzer, the process when the information code is valid.

9. The maintenance method of claim 8, wherein the executing includes displaying, when the information code is not valid, a message by the analyzer without executing the process by the analyzer, the message indicating that the information code is not valid.

10. The maintenance method of claim 1, further comprising:

displaying, by the analyzer, an information code that allows reading of information stored in the analyzer;

reading said information code by the terminal;

transmitting the information from the terminal to a management device that is not communicably connected to the analyzer and that is communicably connected to the terminal, the information having been read from said information code; and receiving, by the management device, input of one or more of the processes corresponding to the information having been transmitted.

11. The maintenance method of claim 10, further comprising transmitting information from the management device to the terminal, the information indicating the processes the input of which has been received, wherein the presenting includes displaying, by the terminal, the information code that allows reading of the information indicating the processes the input of which has been received.

12. The maintenance method of claim 10, wherein the executing includes displaying, by the analyzer, the information code that allows reading of quality control-related information obtained by the analyzer after the process is executed by the analyzer, the maintenance method further comprising:

reading said information code by the terminal; and transmitting, to the management device, the information having been read from said information code.

13. The maintenance method of claim 1, wherein the analyzer is not connected to the Internet.

14. The maintenance method of claim 1, wherein the terminal is connected via a mobile communication network to the Internet.

15. The maintenance method of claim 1, wherein the terminal is a smartphone or a tablet terminal.

16. A system for performing a troubleshooting of an analyzer comprising:

an analyzer that is not communicably connected to a network outside of a facility, wherein the analyzer comprises:

a suction unit configured to suction a specimen from a specimen container;

a sample preparation unit configured to prepare a measurement sample from the suctioned specimen;

a detector configured to measure components in the measurement sample;

a display configured to display a measurement result obtained by measurement by the detector; and a reader configured to optically read an information code; and a terminal that is communicably connected to the network outside of the facility, wherein the terminal is configured to present the information code encoding information about a process to be executed for troubleshooting of the analyzer;

wherein the reader of the analyzer is configured to read the information code presented by the terminal to cause the analyzer to determine a troubleshooting operation and execute the determined troubleshooting operation process.

17. The system of claim 16, wherein the terminal is communicably connected to a management device via the network, the terminal is configured to obtain the information about the process to be executed by the analyzer.

18. The system of claim 17, wherein the analyzer is configured to display an information code that allows reading of information stored in the analyzer, and the terminal is configured to transmit, in response to reading the information code, the information from the terminal to the management device.

19. The system of claim 18, wherein the terminal is configured to receive from the management device the information indicating the processes, and to present the information code corresponding to the information received.

20. The system of claim 16, wherein the terminal is connected via a mobile communication network to the Internet.

* * * * *